US010472680B2

(12) United States Patent
Mitchell et al.

(10) Patent No.: US 10,472,680 B2
(45) Date of Patent: Nov. 12, 2019

(54) HIGHLY SENSITIVE TRANSPLANT REJECTION SURVEILLANCE USING TARGETED DETECTION OF DONOR SPECIFIC CELL FREE DNA

(71) Applicant: Medical College of Wisconsin, Inc., Milwaukee, WI (US)

(72) Inventors: Aoy Tomita Mitchell, Elm Grove, WI (US); Michael Mitchell, Elm Grove, WI (US)

(73) Assignee: Medical College of Wisconsin, Inc., Milwaukee, WI (US)

( * ) Notice: Subject to any disclaimer, the term of this patent is extended or adjusted under 35 U.S.C. 154(b) by 0 days.

(21) Appl. No.: 15/376,621

(22) Filed: Dec. 12, 2016

(65) Prior Publication Data

US 2017/0114411 A1 Apr. 27, 2017

Related U.S. Application Data

(63) Continuation of application No. 14/395,671, filed as application No. PCT/US2013/037439 on Apr. 19, 2013.

(60) Provisional application No. 61/798,421, filed on Mar. 15, 2013, provisional application No. 61/700,873, filed on Sep. 13, 2012, provisional application No. 61/635,723, filed on Apr. 19, 2012.

(51) Int. Cl.
*G01N 33/48* (2006.01)
*C12Q 1/6883* (2018.01)
*C12Q 1/6827* (2018.01)
*C12Q 1/6886* (2018.01)

(52) U.S. Cl.
CPC ........ *C12Q 1/6883* (2013.01); *C12Q 1/6827* (2013.01); *C12Q 1/6886* (2013.01); *C12Q 2600/118* (2013.01); *C12Q 2600/158* (2013.01)

(58) Field of Classification Search
None
See application file for complete search history.

(56) References Cited

U.S. PATENT DOCUMENTS

| 5,569,582 | A | 10/1996 | Tavernarakis et al. |
| 5,595,890 | A | 1/1997 | Newton et al. |
| 5,645,988 | A | 7/1997 | Vande et al. |
| 7,718,370 | B2 | 5/2010 | Dhallan |
| 2003/0148301 | A1 | 8/2003 | Aono et al. |
| 2006/0014179 | A1 | 1/2006 | Roberts |
| 2009/0087847 | A1 | 4/2009 | Lo et al. |
| 2010/0326218 | A1 | 12/2010 | Boeckh et al. |

(Continued)

FOREIGN PATENT DOCUMENTS

| EP | 1325963 A1 | 7/2003 |
| EP | 2551356 A1 | 1/2013 |

(Continued)

OTHER PUBLICATIONS

PCT/US2013/037439, Feb. 4, 2014, International Search Report and Written Opinion.

(Continued)

*Primary Examiner* — Larry D Riggs, II
(74) *Attorney, Agent, or Firm* — Wolf, Greenfield & Sacks, P.C.

(57) ABSTRACT

Provided herein are methods and computer-readable storage media related to cell-free DNA and uses thereof to determine risk of a condition, such as transplant rejection or cancer, in a subject.

12 Claims, 28 Drawing Sheets

(56) References Cited

U.S. PATENT DOCUMENTS

| | | | |
|---|---|---|---|
| 2012/0021442 | A1 | 1/2012 | Buhimschi et al. |
| 2012/0034685 | A1 | 2/2012 | Sparks et al. |
| 2012/0270212 | A1 | 10/2012 | Rabinowitz et al. |
| 2013/0071844 | A1 | 3/2013 | Makin et al. |
| 2013/0143219 | A1 | 6/2013 | Mitchell et al. |
| 2013/0231252 | A1 | 9/2013 | Mitchell et al. |
| 2013/0323727 | A1 | 12/2013 | Huang et al. |
| 2015/0056617 | A1 | 2/2015 | Whitt et al. |
| 2015/0086477 | A1 | 3/2015 | Mitchell et al. |
| 2016/0115541 | A1 | 4/2016 | Schutz et al. |
| 2018/0142296 | A1 | 5/2018 | Mitchell et al. |

FOREIGN PATENT DOCUMENTS

| | | | |
|---|---|---|---|
| JP | 2004-121087 A | | 4/2004 |
| WO | WO 2011/015944 A2 | | 2/2011 |
| WO | WO 2011/057061 | | 5/2011 |
| WO | WO 2011/094646 A1 | | 8/2011 |
| WO | WO 2012/122374 | | 9/2012 |
| WO | WO 2013/159035 A2 | | 10/2013 |
| WO | WO 2014/194113 A2 | | 12/2014 |
| WO | WO 2015/035177 A1 | | 3/2015 |
| WO | WO 2015/069933 A1 | | 5/2015 |
| WO | WO 2015/178978 A2 | | 11/2015 |
| WO | WO 2016/063122 A1 | | 4/2016 |
| WO | WO 2016/123698 A1 | | 8/2016 |
| WO | WO 2016/176662 A1 | | 11/2016 |

OTHER PUBLICATIONS

PCT/US2013/037439, Oct. 30, 2014, International Preliminary Report on Patentability.
PCT/US2013/037439, Dec. 10, 2013, Invitation to Pay Additional Fees.
PCT/US2014/028205, Jul. 10, 2014, International Search Report and Written Opinion.
EP 13778797.4, Oct. 23, 2015, Partial Supplementary European Search Report.
EP 13778797.4, Feb. 11, 2016, Extended European Search Report.
[No Author Listed], Google search results for "The Journal of Heart and Lung Transplantation vol. 31, Issue 4, Supplement, pp. A1-A4, S1-S310."
Chu et al., A novel approach toward the challenge of accurately quantifying fetal DNA in maternal plasma. Prenat Diagn. Dec. 2010;30(12-13):1226-9. doi: 10.1002/pd.2656.
Ghanta et al., Non-invasive prenatal detection of trisomy 21 using tandem single nucleotide polymorphisms. PLoS One. Oct. 8, 2010;5(10):e13184.
Hidestrand et al., 254 Highly Sensitive Transplant Rejection Surveillance Using Targeted Detection of Donor Specific Cell Free DNA. J Heart Lung Transplant. Apr. 2012; 31(4):591-2.
Mehra et al., Gene expression profiles and B-type natriuretic peptide elevation in heart transplantation: more than a hemodynamic marker. Circulation. Jul. 4, 2006;114(1 Suppl):I21-6.
Moreira et al., Cell-Free DNA as a Noninvasive Acute Rejection Marker in Renal Transplantation. Clinical Chem vol. 55, No. 11 pp. 1958-1966 (2009).
Roedder et al., Biomarkers in solid organ transplantation: establishing personalized transplantation medicine. Genome Med. Jun. 8, 2011;3(6):37.
Singh et al., Aspergillus infections in transplant recipients. Clin Microbiol Rev. Jan. 2005;18(1):44-69.
Snyder et al., Universal noninvasive detection of solid organ transplant rejection. Proc Natl Acad Sci U S A. Apr. 12, 2011;108(15):6229-34. Epub Mar. 28, 2011.
Sparks et al., Selective analysis of cell-free DNA in maternal blood for evaluation of fetal trisomy. Prenat Diagn. Jan. 2012;32(1):3-9. Epub Jan. 6, 2012.
Sparks et al., Noninvasive prenatal detection and selective analysis of cell-free DNA obtained from maternal blood: evaluation for trisomy 21 and trisomy 18. Am J Obstet Gynecol. Apr. 2012;206(4):319. e1-9. doi: 10.1016/j.ajog.2012.01.030. Epub Jan. 26, 2012.
Invitation to Pay Additional Fees for International Application No. PCT/US2011/023067 dated Apr. 18, 2011.
International Search Report and Written Opinion for International Application No. PCT/US2011/023067 dated Jul. 5, 2011.
International Preliminary Report on Patentability for International Application No. PCT/US2011/023067 dated Aug. 9, 2012.
International Preliminary Report on Patentability for International Application No. PCT/US2014/028205 dated Sep. 15, 2015.
International Search Report and Written Opinion for International Application No. PCT/US2016/030313 dated Aug. 4, 2016.
International Preliminary Report on Patentability for International Application No. PCT/US2016/030313 dated Nov. 9, 2017.
International Search Report and Written Opinion for International Application No. PCT/US2017/030291 dated Jun. 29, 2017.
International Preliminary Report on Patentability for International Application No. PCT/US2017/030291 dated Nov. 8, 2018.
International Search Report and Written Opinion for International Application No. PCT/US2017/030292 dated Aug. 3, 2017.
International Preliminary Report on Patentability for International Application No. PCT/US2017/030292 dated Nov. 8, 2018.
International Search Report and Written Opinion for International Application No. PCT/US2017/030293 dated Aug. 3, 2017.
International Preliminary Report on Patentability for International Application No. PCT/US2017/030293 dated Nov. 8, 2018.
International Search Report and Written Opinion for International Application No. PCT/US2017/059808 dated Jan. 25, 2018.
International Search Report and Written Opinion for International Application No. PCT/US2017/059802 dated Jan. 19, 2018.
International Search Report and Written Opinion for International Application No. PCT/US2018/038598 dated Sep. 7, 2018.
International Search Report and Written Opinion for International Application No. PCT/US2018/038604 dated Sep. 3, 2018.
International Search Report and Written Opinion for International Application No. PCT/US2018/038609 dated Sep. 10, 2018.
[No Author Listed], Nucleic acid sequence search reports AC: 151794. Oct. 7, 1997. Sequence 6 from U.S. Pat. No. 5645988, Accession 151796.
Adamek et al., A fast and simple method for detecting and quantifying donor-derived cell-free DNA in sera of solid organ transplant recipients as a biomarker for graft function. Clin Chem Lab Med. Jul. 1, 2016;54(7): 1147-55. doi: 10.1515/cclm-2015-0622.
Bai et al., Detection and quantification of heteroplasmic mutant mitochondrial DNA by real-time amplification refractory mutation system quantitative PCR analysis: a single-step approach. Clin Chem. Jun. 2004;50(6):996-1001. Epub Apr. 8, 2004.
Bergallo et al., A novel TaqMAMA assay for allelic discrimination of TLR9 rs352140 polymorphism. J Virol Methods. May 2017;243:25-30. doi: 10.1016/j.jviromet.2017.01.015. Epub Jan. 28, 2017.
Board et al., Detection of PIK3CA mutations in circulating free DNA in patients with breast cancer. Breast Cancer Res Treat. Apr. 2010;120(2):461-7. doi: 10.1007/s10549-010-0747-9. Epub Jan. 28, 2010.
Chiu et al., Effects of blood-processing protocols on fetal and total DNA quantification in maternal plasma. Clin Chem. Sep. 2001;47(9):1607-13. PubMed PMID: 11514393.
Daly, Circulating donor-derived cell-free DNA: a true biomarker for cardiac allograft rejection? Ann Transl Med. Mar. 2015;3(4):47. doi:10.3978/j.issn.2305-5839.2015.01.35.
De Vlaminck et al., Circulating cell-free DNA enables noninvasive diagnosis of heart transplant rejection. Sci Transl Med. Jun. 18, 2014;6(241):241ra77. doi: 10.1126/scitranslmed.3007803.
Gordon et al., an Algorithm Measuring Donor Cell-Free DNA in Plasma of Cellular and Solid Organ Transplant Recipients That Does Not Require Donor or Recipient Genotyping. Front Cardiovasc Med. Sep. 22, 2016;3:33. eCollection 2016.
Gotoh et al., Prediction of MYCN amplification in neuroblastoma using serum DNA and real-time quantitative polymerase chain reaction. J Clin Oncol. Aug. 1, 2005;23(22):5205-10. PubMed PMID: 16051962.

(56) References Cited

OTHER PUBLICATIONS

Grskovic et al., Validation of a Clinical-Grade Assay to Measure Donor-Derived Cell-Free DNA in Solid Organ Transplant Recipients. J Mol Diagn. Nov. 2016;18(6):890-902. doi: 10.1016/j.jmoldx.2016.07.003. Epub Oct. 7, 2016.
Guedj et al., A refined molecular taxonomy of breast cancer. Oncogene. Mar. 1, 2012;31(9):1196-206. doi: 10.1038/onc.2011.301. Epub Jul. 25, 2011.
Hidestrand et al., Highly sensitive noninvasive cardiac transplant rejection monitoring using targeted quantification of donor-specific cell-free deoxyribonucleic acid. J Am Coll Cardiol. Apr. 1, 2014;63(12):1224-1226. doi:10.1016/j.jacc.2013.09.029. Epub Oct. 16, 2013.
Khush et al., Circulating cell-free DNA as a non-invasive marker of pediatric heart transplant rejection and immunosuppressive treatment. J Heart Lung Transplantation. Apr. 2016. 35(4):Abstract 181. S75.
Lang et al., Optimized allele-specific real-time PCR assays for the detection of common mutations in KRAS and BRAF. J Mol Diagn. Jan. 2011;13(1):23-8. doi: 10.1016/j.jmoldx.2010.11.007. Epub Dec. 23, 2010.
Li et al., Multiplex co-amplification of 24 retinoblastoma gene exons after pre-amplification by long-distance PCR. Nucleic Acids Res. Feb. 1, 1996;24(3):538-9.
Lo, Transplantation monitoring by plasma DNA sequencing. Clin Chem. Jul. 2011;57(7):941-2. doi: 10.1373/clinchem.2011.166686. PubMed PMID: 21566070.
Manage et al., Genotyping single nucleotide polymorphisms in human genomic DNA with an automated and self-contained PCR cassette. J Mol Diagn. Sep. 2014;16(5):550-557. doi:10.1016/j.jmoldx.2014.04.004. Epub Jul. 2, 2014.
Myers et al., ACB-PCR quantification of somatic oncomutation. Methods Mol Biol. 2014;1105:345-63. doi:10.1007/978-1-62703-739-6_27.
Parsons et al., Allele-specific competitive blocker-PCR detection of rare base substitution. Methods Mol Biol. 2005;291:235-45.
Ragalie et al., Noninvasive Assay for Donor Fraction of Cell-Free DNA in Pediatric Heart Transplant Recipients. J Am Coll Cardiol. Jun. 26, 2018;71(25):2982-2983. doi: 10.1016/j.jacc.2018.04.026.
Saukkonen et al., Cell-free plasma DNA as a predictor of outcome in severe sepsis and septic shock. Clin Chem. Jun. 2008;54(6):1000-7. doi: 10.1373/clinchem.2007.101030. Epub Apr. 17, 2008. PubMed PMID: 18420731.
Schnittger et al., Development and validation of a real-time quantification assay to detect and monitor BRAFV600E mutations in hairy cell leukemia. Blood. Mar. 29, 2012;119(13):3151-4. doi: 10.1182/blood-2011-10-383323. Epub Feb. 13, 2012.
Sheffield et al., Attachment of a 40-base-pair G + C-rich sequence (GC-clamp) to genomic DNA fragments by the polymerase chain reaction results in improved detection of single-base changes. Proc Natl Acad Sci U S A. Jan. 1989;86(1):232-6.
Sigdel et al., A rapid noninvasive assay for the detection of renal transplant injury. Transplantation. Jul. 15, 2013;96(1):97-101. doi: 10.1097/TP.0b013e318295ee5a.
Snyder et al., Universal noninvasive detection of solid organ transplant rejection. Proc Natl Acad Sci U S A. Apr. 12, 2011;108(15):6229-34. doi: 10.1073/pnas.1013924108. Epub Mar. 28, 2011. PubMed PMID: 21444804; PubMed Central PMCID: PMC3076856.
Stemmer et al., Use of magnetic beads for plasma cell-free DNA extraction: toward automation of plasma DNA analysis for molecular diagnostics. Clin Chem. Nov. 2003;49(11):1953-5. PubMed PMID: 14578335.
Swinkels et al., Effects of blood-processing protocols on cell-free DNA quantification in plasma. Clin Chem. Mar. 2003;49(3):525-6. PubMed PMID: 12600978.
Takai et al., Clinical utility of circulating tumor DNA for molecular assessment in pancreatic cancer. Sci Rep. Dec. 16, 2015;5:18425. doi: 10.1038/srep18425.
Tamkovich et al., Circulating nucleic acids in blood of healthy male and female donors. Clin Chem. Jul. 2005;51(7):1317-9. PubMed PMID: 15976134.
Tong et al., Diagnostic developments involving cell-free (circulating) nucleic acids. Clin Chim Acta. Jan. 2006;363(1-2):187-96. Epub Aug. 26, 2005. Review. PubMed PMID: 16126188.
Van Orsouw et al., Rapid design of denaturing gradient-based two-dimensional electrophoretic gene mutational scanning tests. Nucleic Acids Res. May 15, 1998;26(10):2398-406.
Vannucchi et al., A quantitative assay for JAK2(V617F) mutation in myeloproliferative disorders by ARMS-PCR and capillary electrophoresis. Leukemia. Jun. 2006;20(6):1055-60.
Wilkins et al., IMP PCR primers detect single nucleotide polymorphisms for *Anopheles gambiae* species identification, Mopti and Savanna rDNA types, and resistance to dieldrin in *Anopheles arabiensis*. Malar J. Dec. 19, 2006;5:125.
Zhang et al., A novel multiplex tetra-primer ARMS-PCR for the simultaneous genotyping of six single nucleotide polymorphisms associated with female cancers. PLoS One. Apr. 17, 2013;8(4):e62126. doi: 10.1371/journal.pone.0062126. Print 2013.
U.S. Appl. No. 14/395,671, filed Oct. 20, 2014, Mitchell et al.
U.S. Appl. No. 15/570,560, filed Oct. 30, 2017, Mitchell et al.
U.S. Appl. No. 16/097,404, filed Oct. 29, 2018, Mitchell et al.
U.S. Appl. No. 16/097,422, filed Oct. 29, 2018, Mitchell et al.
U.S. Appl. No. 16/097,443, filed Oct. 29, 2018, Mitchell et al.
PCT/US2011/023067, Apr. 18, 2011, Invitation to Pay Additional Fees.
PCT/US2011/023067, Jul. 5, 2011, International Search Report and Written Opinion.
PCT/US2011/023067, Aug. 9, 2012, International Preliminary Report on Patentability.
PCT/US2014/028205, Sep. 15, 2015, International Preliminary Report on Patentability.
PCT/US2016/030313, Aug. 4, 2016, International Search Report and Written Opinion.
PCT/US2016/030313, Nov. 9, 2017, International Preliminary Report on Patentability.
PCT/US2017/030291, Jun. 29, 2017, International Search Report and Written Opinion.
PCT/US2017/030291, Nov. 8, 2018, International Preliminary Report on Patentability.
PCT/US2017/030292, Aug. 3, 2017, International Search Report and Written Opinion.
PCT/US2017/030292, Nov. 8, 2018, International Preliminary Report on Patentability.
PCT/US2017/030293, Aug. 3, 2017, International Search Report and Written Opinion.
PCT/US2017/030293, Nov. 8, 2018, International Preliminary Report on Patentability.
PCT/US2017/059808, Jan. 25, 2018, International Search Report and Written Opinion.
PCT/US2017/059802, Jan. 19, 2018, International Search Report and Written Opinion.
PCT/US2018/038598, Sep. 7, 2018, International Search Report and Written Opinion.
PCT/US2018/038604, Sep. 3, 2018, International Search Report and Written Opinion.
PCT/US2018/038609, Sep. 10, 2018, International Search Report and Written Opinion.

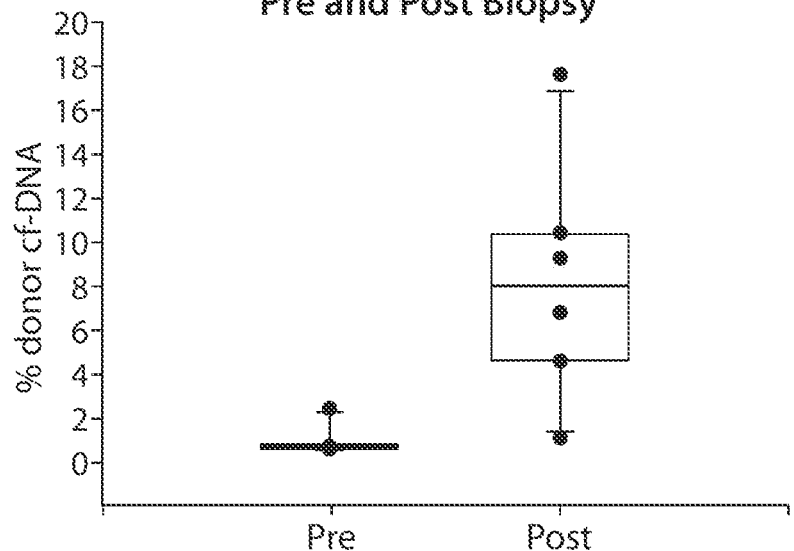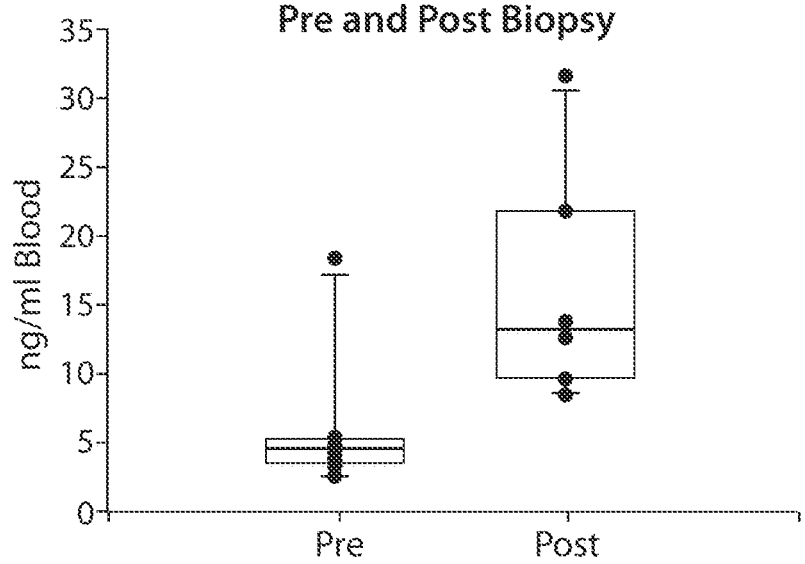
Fig. 15

Methods

* 130 Plasma samples (1.5 ml) were collected from 38 pediatric heart transplant recipients blinded and coded:

* 64 at routine surveillance biopsy (SB: 34 patients)
* 19 during admission for biopsy proven rejection (Rj: 5 patients)
  * Each suspected rejection episode included 3 samples (Day 1,4,8)
* 47 following heart transplantation (POD: 13 patients)
  * Each with at least 3 samples (Day 1,4,8)

* Total cell free DNA was prepared from plasma[1]. The fraction of donor specific cell free DNA in the sample was determined using targeted next-gen sequencing[2]

192 Loci/ patient
All samples were informative

Results unblinded and compared to clinical data

[1] Hidestrand *et al* 2012, Fetal Diagnosis and Therapy
[2] Sparks *et al* 2012, Journal of Prenatal Diagnosis

Fig. 16

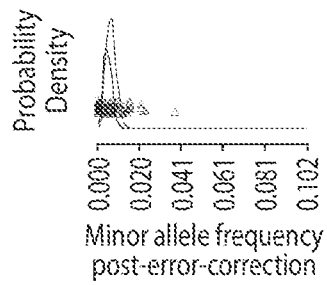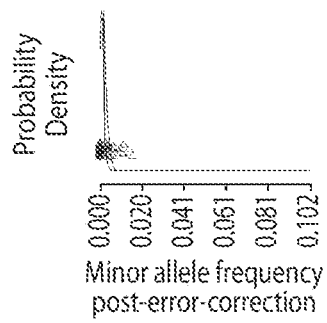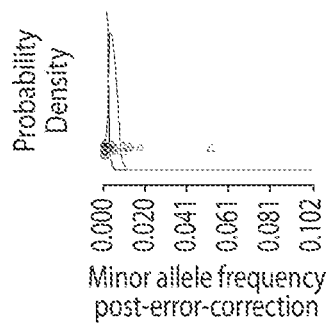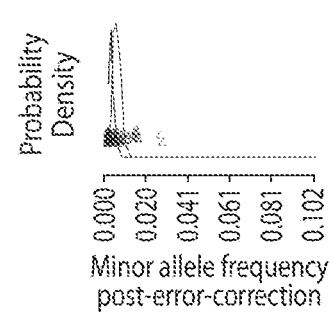
Fig. 18 cont.

HIGHLY SENSITIVE TRANSPLANT REJECTION SURVEILLANCE USING TARGETED DETECTION OF DONOR SPECIFIC CELL FREE DNA

RELATED APPLICATIONS

This application is a continuation of U.S. patent application Ser. No. 14/395,671, filed Oct. 24, 2014, pending, which claims the benefit under 35 U.S.C. 119(e) of the filing date of U.S. Provisional Application 61/635,723, filed Apr. 19, 2012; the filing date of U.S. Provisional Application 61/700,873, filed Sep. 13, 2012; and the filing date of U.S. Provisional Application 61/798,421, filed Mar. 15, 2013; the contents of each which are incorporated herein by reference in their entirety.

SUMMARY OF THE INVENTION

In one aspect, a method of assessing a risk in a subject is provided. The method may comprise any of the steps provided herein. In one embodiment, the method comprises analyzing nucleic acids from cell-free DNA extracted from a biological sample obtained from the subject to identify a plurality of loci, the nucleic acids comprising first nucleic acids of the subject and second nucleic acids not native to the subject; determining an allele of each of the plurality of loci; selecting at least one informative locus from the plurality of loci based on the determining of the allele; calculating an estimated allele frequency of a first allele at the at least one informative locus using a statistical distribution; determining an amount of cell-free DNA not native to the subject in the cell-free DNA based on the estimated allele frequency; and determining a risk in the subject based on the determined amount of the cell-free DNA not native to the subject in the cell-free DNA.

In another aspect, a method of treatment of a subject is provided. In one embodiment, the method comprises determining an amount of cell-free DNA not native to the subject in cell-free DNA extracted from a biological sample from the subject; determining a risk in the subject based on the determined amount of the cell-free DNA not native to the subject; and administering a therapy, or providing information about a therapy, to the subject based on the determined risk. In one embodiment, the determining an amount of cell-free DNA not native to the subject comprises analyzing nucleic acids from the extracted cell-free DNA to identify a plurality of loci, the nucleic acids comprising first nucleic acids of the subject and second nucleic acids not native to the subject; determining an allele of each of the plurality of loci; selecting at least one informative locus from the plurality of loci based on the determining of the allele; and calculating an estimated allele frequency of a first allele at the at least one informative locus using a statistical distribution, wherein the amount of cell-free DNA not native to the subject is based on the estimated allele frequency.

In another aspect, a method of assessing a risk of a systemic disease in a recipient of a transplant is provided. In one embodiment, the method comprises quantifying the amount of cell-free DNA extracted from a biological sample obtained from the recipient of a transplant; and determining a risk of a systemic disease in the recipient of a transplant based on the determined amount of the cell-free DNA. In one embodiment, the risk is indicative of the presence or absence of a systemic disease. In one embodiment, the method further comprises in a case where the amount of the cell-free DNA is greater than a threshold value, determining that the risk is increased. In another embodiment, the method further comprises based on the determined amount of the cell-free DNA, administering a therapy or providing information about a therapy to the recipient of a transplant. In another embodiment, the method further comprises based on the determined amount of the cell-free DNA, evaluating an effect of a therapy administered to the recipient of a transplant. In one embodiment, a decreased amount of the determined amount of the cell-free DNA is indicative of a positive effect of the therapy. In another embodiment, the method further comprises based on the determined amount of the cell-free DNA, predicting the likely clinical course.

In another aspect, a method of treatment of a recipient of a transplant is provided. In one embodiment, the method comprises quantifying the amount of cell-free DNA extracted from a biological sample obtained from the recipient of a transplant; determining a risk of a systemic disease in the recipient of a transplant based on the determined amount of the cell-free DNA; and administering a therapy, or providing information about a therapy, to the recipient of a transplant based on the determined risk. In one embodiment, the risk is indicative of the presence or absence of a systemic disease. In one embodiment, the method further comprises in a case where the amount of the cell-free DNA is greater than a threshold value, determining that the risk is increased.

In another aspect, a method of evaluating a subject is provided. In one embodiment, the method comprises calculating a value for a Predictive Model, and assessing the condition of the subject. In one embodiment, the Predictive Model is the Predictive Model of Formula 1 using values for the time post-initiation of therapy (e.g., surgical or pharmaceutical)×non-native cf-DNA. Predictive Model (Formula 1)=time post initiation of therapy (e.g., surgical or pharmaceutical)×non-native cf-DNA. In another embodiment, the Predictive Model is the Predictive Model of Formula 2 using values for the time post-clamp removal, recipient weight, donor weight, and donor-specific cell-free DNA. Predictive Model (Formula 2)=time post-clamp removal×(recipient weight/donor weight)×donor-specific cell-free DNA. In another embodiment, the Predictive Model is the Predictive Model of Formula 3 using values for the time post initiation of a therapy (e.g., anti-rejection therapy, such as an immunosuppressive therapy, a therapy for treating systemic disease or anti-cancer therapy), recipient weight, donor weight and non-native cell-free DNA. Predictive Model (Formula 3)=time post initiation of a therapy×(recipient weight/donor weight)×non-native cell-free DNA. In one embodiment, the non-native cf-DNA is DS cf-DNA, CS cf-DNA or bacterial, fungal or viral DNA. In one embodiment, the method further comprises determining an amount of non-native cell-free DNA in a biological sample from the subject. In one embodiment, the determining an amount of non-native cell-free DNA comprises any of the steps of the methods for doing so provided herein, including those in the Examples and Figures. In one embodiment, determining an amount of non-native cell-free DNA comprises analyzing nucleic acids from extracted cell-free DNA from the biological sample to identify a plurality of loci, the nucleic acids comprising first nucleic acids of the subject and second nucleic acids of the donor; determining an allele of each of the plurality of loci; selecting at least one informative locus from the plurality of loci based on the determining of the allele; and calculating an estimated allele frequency of a first allele at the at least one informative locus using a statistical distribution, wherein the amount of non-native cell-free DNA is based on the estimated allele frequency. In another embodiment, the method further comprises determining or obtaining the time post initiation of therapy (e.g., as in Formula 1, 2 or 3), recipient weight and/or donor weight. In another embodiment, the method further comprises comparing the value for the Predictive Model (e.g., as in Formula 1, 2 or 3) with a threshold value to assess the condition of the subject. In one embodiment, the assessing the condition comprises determining a risk associated with a transplant or cancer or predicting the likely clinical course. In another embodiment, the method further comprises, based on the assessing, administering a therapy or providing information about a therapy to the subject. In another embodiment, the method further comprises, based on the assessing, evaluating an effect of a therapy administered to subject. In one embodiment, the amount of the therapy administered to the subject is increased or decreased based on the evaluation. In another embodiment, a different therapy is administered to the subject based on the evaluation. In one embodiment, a value of the Predictive Model (e.g., as in Formula 1, 2 or 3) is determined at one point in time to assess the condition of the subject. In another embodiment, a value of the Predictive Model (e.g., as in Formula 1, 2 or 3) is determined at at least two points in time to assess the condition of the subject. Values for the Predictive Model (e.g., as in Formula 1, 2 or 3) can be determined over a period of time to assess the condition of the subject.

In another aspect, a method of monitoring over a time period a risk in a subject is provided. In one embodiment, the method comprises determining/assessing/evaluating the risk in the subject at least twice. The method for determining/assessing/evaluating the risk may comprise any of the methods provided herein, including those in the Examples and Figures. In one embodiment, the method comprises performing any of the other methods provided herein at least twice. In another embodiment, the method comprises evaluating the subject at least twice. The method for evaluating the subject may comprise the steps of any of the methods provided herein, including those in the Examples and Figures. In one embodiment, the method of monitoring over a time period can further comprise performing an additional test on the subject or a biological sample obtained from the subject. In another embodiment, the method of monitoring over a time period can further comprise treating the subject with a therapy or providing information about a therapy to the subject.

In another aspect, at least one computer-readable storage medium storing computer-executable instructions that, when executed by at least one processor, cause a computing device to perform any of the methods, or one or more of the steps thereof, provided herein, including those in the Examples and Figures, is provided. In one embodiment, the method comprises determining an allele of each of a plurality of loci; selecting at least one informative locus from the plurality of loci based on the determining of the allele; calculating an estimated allele frequency of a first allele at the at least one informative locus using a statistical distribution; and determining an amount of cell-free DNA not native to a subject in the cell-free DNA based on the estimated allele frequency. In one embodiment, the method further comprises determining a risk in the subject based on the determined amount of the cell-free DNA not native to the subject in the cell-free DNA.

In another embodiment, the method comprises determining an amount of cell-free DNA not native to a subject in cell-free DNA extracted from a biological sample from the subject; and determining a risk in the subject based on the determined amount of the cell-free DNA not native to the subject. In one embodiment, determining an allele of each of a plurality of loci; selecting at least one informative locus from the plurality of loci based on the determining of the allele; and calculating an estimated allele frequency of a first allele at the at least one informative locus using a statistical distribution, wherein the amount of cell-free DNA not native to the subject is based on the estimated allele frequency. In one embodiment, the method further comprises determining an amount of cell-free DNA not native to the subject comprises analyzing nucleic acids from the extracted cell-free DNA to identify a plurality of loci, the nucleic acids comprising first nucleic acids of the subject and second nucleic acids not native to the subject.

In another embodiment, the method comprises quantifying an amount of cell-free DNA extracted from a biological sample obtained from a recipient of a transplant; and determining a risk of a systemic disease in the recipient of a transplant based on the determined amount of the cell-free DNA.

In another embodiment, the method comprises calculating a value for a Predictive Model (e.g., as in Formula 1, 2 or 3). In one embodiment, the method further comprises assessing the condition of the subject. In another embodiment, the method further comprises determining an amount of non-native cell-free DNA in a biological sample from the subject. In one embodiment, determining an amount of non-native cell-free DNA comprises analyzing nucleic acids from extracted cell-free DNA from the biological sample to identify a plurality of loci, the nucleic acids comprising first nucleic acids of the subject and second nucleic acids not native to the subject; determining an allele of each of the plurality of loci; selecting at least one informative locus from the plurality of loci based on the determining of the allele; and calculating an estimated allele frequency of a first allele at the at least one informative locus using a statistical distribution, wherein the amount of non-native cell-free DNA is based on the estimated allele frequency. In another embodiment, the method further comprises comparing the value for the Predictive Model (e.g., as in Formula 1, 2 or 3) with a threshold value to assess the condition of the subject.

In one embodiment of any of the methods provided herein, the subject is a recipient of a transplant, and the risk is a risk associated with the transplant. In one embodiment, the risk associated with the transplant is risk of transplant rejection, an anatomical problem with the transplant or injury to the transplant. In another embodiment, the injury to the transplant is initial or ongoing injury. In another embodiment, the risk associated with the transplant is indicative of the severity of the injury. In another embodiment, the risk associated with the transplant is a risk of having or developing a systemic disease. In one embodiment, the systemic disease is inflammation, infection or sepsis. In another embodiment, the risk associate with the transplant is indicative of the bacterial, fungal and/or viral load.

In one embodiment of any of the methods provided herein, the cell-free DNA is total cell-free DNA or cell-free DNA native to the subject.

In one embodiment of any of the methods provided herein, the cell-free DNA not native to the subject is donor-specific cell-free DNA.

In one embodiment of any of the methods provided herein, the subject has or is at risk of having a cancer, and the risk is a risk associated with the cancer. In one embodiment, the risk associated with the cancer is the presence or absence of the cancer, recurrence of the cancer or metastasis of the cancer. In another embodiment, the risk associated with the cancer is indicative of the cancer load in the subject.

In one embodiment of any of the methods provided herein, the cell-free DNA not native to the subject is cancer-specific cell-free DNA.

In one embodiment of any of the methods provided herein, the method further comprises extracting the cell-free DNA from the biological sample.

In one embodiment of any of the methods provided herein, the first allele comprises a minor allele.

In one embodiment of any of the methods provided herein, the at least one informative locus is selected by detecting the first allele and a second allele at a locus; and determining that the first nucleic acids are homozygous for the second allele at the at least one informative locus and the second nucleic acids are heterozygous or homozygous for the first allele at the at least one informative locus.

In one embodiment of any of the methods provided herein, the first allele comprises a minor allele and the second allele comprises a major allele.

In one embodiment of any of the methods provided herein, the first allele comprises a minor allele; and the estimated allele frequency of the minor allele is calculated using a statistical distribution. In one embodiment, the statistical distribution is a binomial distribution.

In one embodiment of any of the methods provided herein, the first allele comprises a minor allele; and the estimated allele frequency of the minor allele is calculated using an expectation-maximization algorithm. In one embodiment, the expectation-maximization algorithm is a maximum likelihood method.

In one embodiment, of any of the methods provided herein, the estimated allele frequency is calculated using a combination of a statistical distribution, such as a binomial distribution, and an expectation-maximixation algorithm, such a maximum likelihood method.

Preferably, in some embodiments, the number of informative reads is at least 100, 200, 300, 400, 500, 600, 700, 800, 900, 1000, 1100 or 1200. In one embodiment, the method also comprises correcting the count or number of reads of the major and minor alleles of the at least one informative locus.

In one embodiment of any of the methods provided herein, the nucleic acids are analyzed using high-throughput DNA sequencing. In one embodiment of any of the methods provided herein, the nucleic acids are analyzed using quantitative genotyping. In one embodiment of any of the methods provided herein, the nucleic acids are analyzed using next generation sequencing.

In one embodiment of any of the methods provided herein, the method further comprises in a case where the amount of the cell-free DNA not native to the subject in the cell-free DNA is greater than a threshold value, determining that the risk is increased. In one embodiment, when the subject is a recipient of a transplant, the threshold value comprises 1%.

In one embodiment of any of the methods provided herein, the method further comprises in a case where the amount of the cell-free DNA not native to the subject in the cell-free DNA is equal to or less than a threshold value, determining that the risk is decreased. In one embodiment, when the subject is a recipient of a transplant, the threshold value comprises 1%.

In one embodiment of any of the methods provided herein, when the subject is a recipient of a transplant, the method is performed within 10, 9, 8, 7, 6, 5, 4, 3, 2 or 1 day of receiving the transplant. In one embodiment, when the subject is a recipient of a transplant, the method is performed within 10 days of receiving the transplant. In another embodiment, when the subject is a recipient of a transplant, the method is performed within 5 days of receiving the transplant. In another embodiment, when the subject is a recipient of a transplant, the method is performed within 3 days of receiving the transplant.

In one embodiment of any of the methods provided herein, when the subject is a recipient of a transplant the method is performed at a time of a scheduled endomyocardial biopsy (EMB).

In one embodiment of any of the methods provided herein, the method further comprises, based on the determined amount of the cell-free DNA not native to the subject, administering a therapy or providing information about a therapy to the subject.

hi one embodiment of any of the methods provided herein, the method further comprises, based on the determined amount of the cell-free DNA, such as cell-free DNA not native to the subject, evaluating an effect of a therapy administered to the subject. In one embodiment, a decreased amount of the determined amount of the cell-free DNA, such as the cell-free DNA not native to the subject, is indicative of a positive effect of the therapy. In another embodiment, the amount of the therapy administered to the subject is increased or decreased based on the evaluation. In another embodiment, a different therapy is administered to the subject based on the evaluation.

In one embodiment of any of the methods provided herein, the therapy is anti-rejection therapy. In one embodiment of any of the methods provided herein, the therapy comprises a therapeutic agent that treats a systemic disease. In one embodiment of any of the methods provided herein, the therapy comprises an anti-cancer therapy.

In one embodiment of any of the methods provided herein, the method further comprises performing an additional test on the subject or biological sample. In one embodiment, the additional test is a test for assessing a risk associated with a transplant. In another embodiment, the additional test is a test for assessing the presence or absence of a cancer, or a recurrence or metastasis thereof.

In one embodiment of any of the methods provided herein, the method further comprises, based on the determined amount of the cell-free DNA not native to the subject, predicting the likely clinical course. In one embodiment, when the subject is a recipient of a transplant predicting the likely clinical course comprises predicting a length of hospital stay after the subject received the transplant, the likelihood of mortality, likelihood of a risk or the likelihood of a problem with the transplant. In one embodiment, predicting the likely clinical course comprises calculating a value for a Predictive Model (e.g., as in Formula 1, 2 or 3).

In one embodiment of any of the methods provided herein, wherein based on the predicted likely clinical course, a course of action is selected for the subject or information about a course of action is provided to the subject.

In one embodiment of any of the methods provided herein, when the subject is a recipient of a transplant, the transplant comprises a heart transplant.

In one embodiment of any of the methods provided herein, the subject is a pediatric patient.

In one embodiment of any of the methods provided herein, the method further comprises obtaining a biological sample from the subject.

In one embodiment of any of the methods provided herein, the biological sample comprises, blood, plasma, serum or urine.

In one embodiment of any of the methods provided herein, the method further comprises determining a value of a Predictive Model (e.g., as in Formula 1, 2 or 3). In one embodiment, the method further comprises assessing the condition of the subject.

In one embodiment of any of the methods provided herein, the method comprises a step of spiking in an internal standard at known quantities to aid in the quantification of the cell-free DNA, such as cell-free DNA not native to the subject.

BRIEF DESCRIPTION OF THE DRAWINGS

FIG. 15 is a series of graphs showing percent DS cf-DNA and T cf-DNA pre and post biopsy.

FIG. 16 describes an exemplary method for collecting and analyzing cf-DNA.

DETAILED DESCRIPTION OF THE INVENTION

Figure 1:
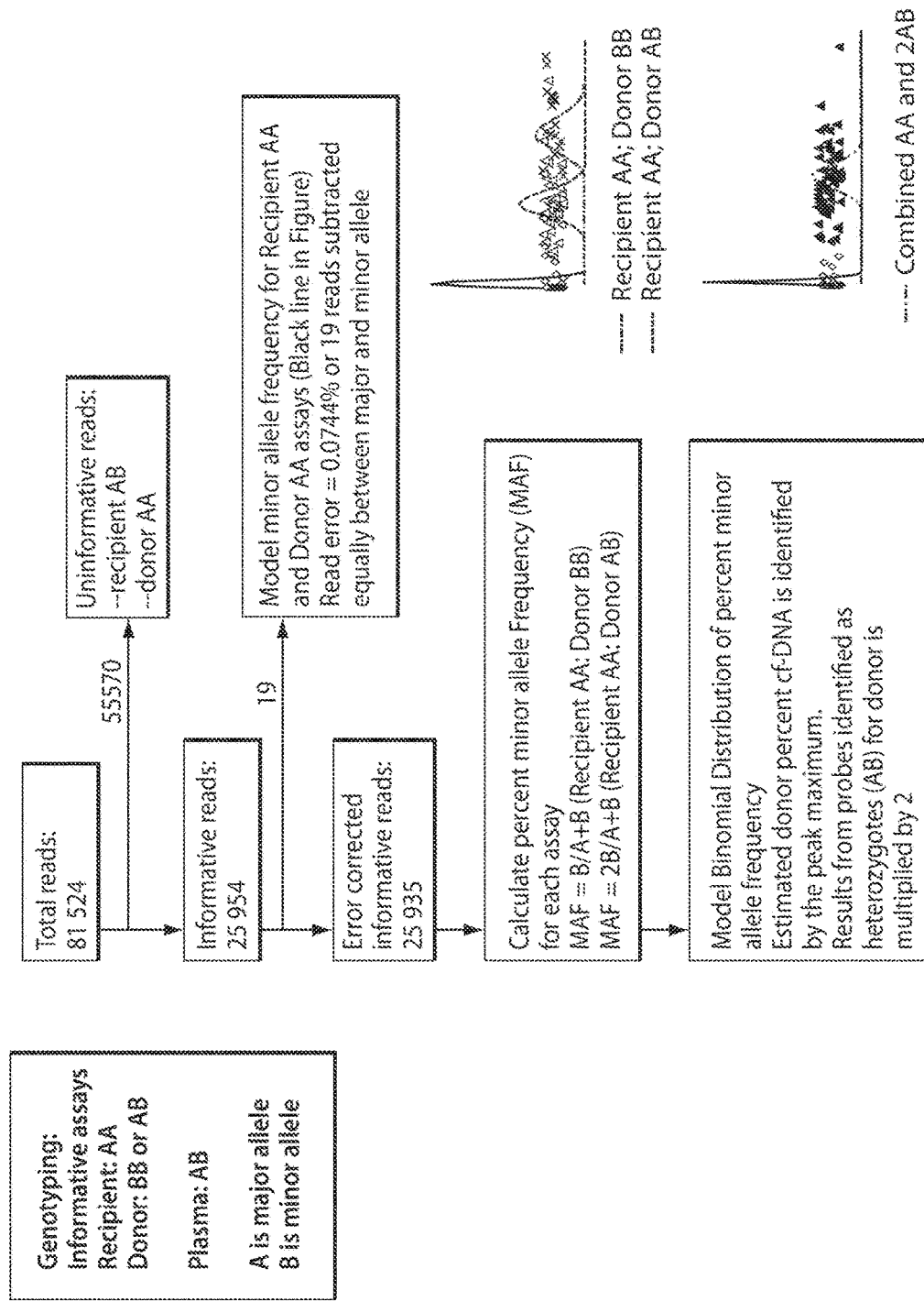
FIG. 1 is a diagram showing the data analysis method performed in Example 1.

Individuals can carry non-native DNA sources in a variety of situations including situations where cancer is present and following organ transplantation, and conditions related thereto. Provided herein are ways to determine amounts of cell-free DNA (cf-DNA), native, total, and/or non-native concentrations from biological samples. What is offered are highly sensitive and quantitative techniques to detect, analyze and also quantify cf-DNA concentrations, for example, at the percent level. Methods provided herein relate to use of non-native (also referred to herein as "not native") cf-DNA and native cf-DNA, or both, obtained from a subject. As used herein, "cell-free DNA" (cf-DNA) is DNA that is present outside of a cell, e.g., in the blood, plasma, serum, or urine of a subject. Without wishing to be bound by any particular theory or mechanism, it is believed that cf-DNA is released from cells, e.g., via apoptosis of the cells. As used herein, "native cf-DNA" or "cf-DNA of the subject" refers to cell-free DNA from cells (e.g., non-cancerous cells of the subject) of the subject. As used herein, "non-native cf-DNA" or "cf-DNA not native to the subject" refers to cell-free DNA from a non-native source that differs from the cf-DNA of the subject, e.g., a difference in sequence identity at one or more loci as described herein. Examples of non-native DNA include, but are not limited to, transplant donor DNA and cancer/tumor DNA. Examples of non-native cf-DNA include, but are not limited to, transplant donor cf-DNA (also referred to herein as donor specific cf-DNA) and tumor cf-DNA (also referred to herein as cancer-specific cf-DNA). The source of non-native cf-DNA depends upon the subject. As another example, non-native cf-DNA include bacterial, fungal and/or viral DNA. For example, if a subject is a transplant recipient, non-native cf-DNA may be shed from the donated transplanted organ (donor specific cf-DNA) and native cf-DNA may be shed by cells from the host/subject (host cf-DNA). If the subject has cancer, non-native cf-DNA may be shed, e.g., by a tumor and/or metastasis (cancer-specific cf-DNA), and native cf-DNA may be shed, e.g., by non-cancerous cells of the subject.

The methods provided herein can include calculating various cf-DNA concentrations, or percent thereof, of a total amount of cf-DNA. These amounts can be compared relative to a threshold (such as a baseline level) and/or changes in such values can be monitored over time. For example, a change from a threshold value (such as a baseline) in the ratio or percent of non-native cf-DNA relative to native cf-DNA or total cf-DNA can be used as a non-invasive clinical indicator of risk, e.g., risk associated with transplant or cancer. This ratio can allow for the measurement of variations in a clinical state and/or permit calculation of normal values or baseline levels. In organ transplantation, this can form the basis of an individualized non-invasive screening test for rejection or a risk of a condition associated thereto; in oncology, this can form the basis of a non-invasive individualized test for the presence or absence of a tumor, recurrence or metastasis, or the progression thereof. While much of the description provided herein focuses on transplant rejection and risks associated thereto, all of the methods and computer-implemented methods or computer-readable storage media can also apply to other subjects, such as a subject with or at risk of having cancer or a tumor, recurrence of cancer or a tumor or metastasis of a cancer or tumor.

As provided herein, early detection of rejection following implantation of a transplant (e.g., a heart transplant) can facilitate treatment and improve clinical outcomes. Transplant rejection remains a major cause of graft failure and late mortality and generally requires lifelong surveillance monitoring. Treatment of transplant rejections with immunosuppressive therapy has been shown to improve treatment outcomes, particularly if rejection is detected early. Transplant rejection is typically monitored using a catheter-based endomyocardial biopsy (EMB). This invasive procedure, however, is associated with risks and discomfort for a patient, and may be particularly disadvantageous for pediatric patients.

Accordingly, provided herein are sensitive, specific, cost effective, and non-invasive techniques for the surveillance of subjects, such as transplant recipients. Such techniques have been surprisingly found to allow for the detection of transplant rejection at an early stage. Such techniques can also be used to monitor organ recovery and in the selection and monitoring of a treatment or therapy, such as an anti-rejection treatment, thus improving a patient's recovery and increasing survival rates.

A "risk" as provided herein, refers to the presence or absence of any undesirable condition in a subject (such as a transplant recipient or subject having or suspected of having cancer, metastasis, and/or recurrence of cancer), or an increased likelihood of the presence or absence of such a condition, e.g., transplant rejection, transplant injury, and/or systemic disease associated with transplant; or cancer, metastasis, and/or recurrence of cancer. The undesirable condition can also include the presence or absence of a bacterial, fungal and/or viral infection. Assessing the load bacterial, fungal and/or viral DNA can be used to determine the extent of the infection. Assessing the load of cancer via the level of CS cf-DNA can be used to determine the presence or absence of cancer, or metastasis or recurrence thereof, or the progression or extent of the cancer. As provided herein "increased risk" refers to the presence of any undesirable condition in a subject or an increased likelihood of the presence of such a condition. As provided herein "decreased risk" refers to the absence of any undesirable condition in a subject or a decreased likelihood of the presence (or increased likelihood of the absence) of such a condition.

In some embodiments, the subject is a recipient of a transplant, and the risk is a risk associated with the transplant. In some embodiments, the risk associated with the transplant is risk of transplant rejection, an anatomical problem with the transplant or injury to the transplant. In some embodiments, the injury to the transplant is initial or ongoing injury. In some embodiments, the risk associated with the transplant is indicative of the severity of the injury. In some embodiments, the risk associated with the transplant is the load of a bacterial, fungal and/or viral infection. In some embodiments, the risk associated with the transplant is a risk of having or developing a systemic disease. As used herein, "systemic disease" refers to a disease that affects a number of organs and tissue, or affects the body as a whole. The systemic disease may be caused by or be a result of a transplant. In some embodiments, the systemic disease is inflammation, infection or sepsis.

In some embodiments, the subject has or is at risk of having a cancer, and the risk is a risk associated with the cancer. In some embodiments, the risk associated with the cancer is the presence or absence of the cancer, recurrence of the cancer or metastasis of the cancer, or progression thereof. In some embodiments, the risk associate with the cancer can be assessed by the load of CS cf-DNA.

The risk in a recipient of a transplant can be determined, for example, by assessing the level of total cell-free DNA and/or non-native cf-DNA, such as bacterial, fungal and/or viral cf-DNA or donor-specific cell-free-DNA (DS cf-DNA), a biomarker for cellular injury related to transplant rejection, through the use of high-throughput sequencing, such as next generation sequencing (NGS), or other type of quantitative genotyping. DS cf-DNA refers to cf-DNA that presumably is shed from the transplanted organ, the sequence of which matches (in whole or in part) the genotype of the donor who donated the transplanted organ. As used herein, DS cf-DNA may refer to certain sequence(s) in the DS cf-DNA population, where the sequence is distinguishable from the host cf-DNA (e.g., having a different sequence at a particular nucleotide location(s)), or it may refer to the entire DS cf-DNA population.

As used herein, "transplant" refers to the moving of an organ from a donor to a host/recipient for the purpose of replacing the host/recipient's damaged or absent organ. The transplant may be of one organ or more than one organ. Examples of organs that can be transplanted include, but are not limited to, the heart, kidney, liver, lung, pancreas, intestine, bone marrow, blood, and thymus. In some embodiments, the transplant is a heart transplant. In some embodiments, the term "transplant" refers to a transplanted organ or organs, and such meaning will be clear from the context the term is used.

The risk in a subject having a cancer or suspected of having cancer can be determined, for example, by assessing the level of total cell-free DNA and/or cancer specific cell-free-DNA (CS cf-DNA), a biomarker for the presence of cancer, metastasis, and/or recurrence of cancer, or progression thereof, through the use of high-throughput sequencing, such as next generation sequencing (NGS), or other type of quantitative genotyping. CS cf-DNA refers to cf-DNA that presumably is shed from a cancer, e.g., a primary tumor and/or metastases, the sequence of which matches (in whole or in part) the genotype of the primary tumor and/or metastases. CS cf-DNA may refer to certain sequences in the CS cf-DNA population, where the sequence is distinguishable from the subject/native cf-DNA (e.g., having a different sequence at a particular nucleotide location(s)), or it may refer to the entire cancer/tumor cf-DNA population.

In some embodiments, certain methods provided herein comprise correlating an increase in total cf-DNA, or native cf-DNA, and/or an increase in non-native cf-DNA (e.g., DS cf-DNA or CS cf-DNA) and/or an increase in the ratio, or percent, of non-native cf-DNA relative to native cf-DNA, with an increased risk of a condition such as transplant rejection, transplant injury, bacterial, fungal and/or viral infection and/or systemic disease associated with transplant; or cancer, metastasis, and/or recurrence in cancer in a subject, or progression or load thereof. In some embodiments, correlating comprises comparing a level (e.g., concentration, ratio or percent) of total cf-DNA, or native cf-DNA, and/or a non-native cf-DNA (e.g., DS cf-DNA or CS cf-DNA) to a threshold value as described herein to identify a subject at increased or decreased risk of a condition. In some embodiments, a subject having an increased level or percentage of total cf-DNA, or native cf-DNA, and/or non-native cf-DNA compared to a threshold value is identified as being at increased risk of a condition. In some embodiments, a subject having a decreased or similar level of total cf-DNA, or native cf-DNA, and/or a non-native cf-DNA compared to a threshold value is identified as being at decreased risk of a condition.

From the examples provided herein it has been demonstrated that levels of DS cf-DNA are elevated during rejection and cardiac allograft injury and decrease during recovery or with treatment. It has also been found that total cf-DNA levels are increased with the presence of systemic disease in transplant recipients. Thus, the amounts of DS cf-DNA or total cf-DNA from a cf-DNA sample obtained from a recipient of a transplant can provide a sensitive and non-invasive way of monitoring graft status, assessing the condition of the transplant, and predicting clinical outcomes following transplantation, such as cardiac transplantation.

In Example 1, below, it has been shown that detection of rejection following pediatric heart transplantation can facilitate treatment and improve clinical outcomes. For this example, a double-blinded prospective pilot study was designed to test the accuracy and clinical relevance of a targeted DNA sequencing method of detection and quantification of DS cf-DNA in pediatric heart transplant recipients. Twenty-four individual plasma samples were collected from 16 pediatric heart transplant recipients in two clinical settings: at routine surveillance biopsy (12 patients, 13 samples) and during treatment for rejection (4 patients, 11 samples) on days 1, 4 and 8. Total cf-DNA was determined by quantitative real time PCR and percent donor-specific DNA cf-DNA was measured using targeted next generation sequencing (NGS) (Ariosa Diagnostics). All samples collected at the initial diagnosis of rejection showed significantly elevated levels of donor cf-DNA ($P<0.002$) which decreased upon increased immunosuppressive therapy ($P<0.038$). All samples, except two, collected during routine catheterization contained below 1% donor specific cf-DNA. Of the two outliers, one sample was from a patient who was subsequently admitted (one week later) in rejection and in whom the surveillance biopsy revealed grade II rejection. The other sample was from a patient with positive antibody cross match but no obvious clinical signs of rejection.

Example 2 (below) also demonstrates that detection of rejection following heart transplantation can facilitate treatment that improves clinical outcomes. In this example, plasma samples (n=98) from transplant recipients (n=38) in five clinical settings were analyzed: 1) post-transplant—three time points, 2) pre- and post-endomyocardial biopsy (EMB), 3) before scheduled surveillance EMB, 4) before unscheduled diagnostic EMB, and 5) at treatment for rejection—three time points. Total cf-DNA (T cf-DNA) was determined by quantitative real time polymerase chain reaction; percent DS cf-DNA was measured using targeted next generation sequencing (NGS) (DANSR™, Ariosa Diagnostics, San Jose, Calif.). A baseline level of DS cf-DNA was established (<1% of Tcf-DNA). The negative predictive value of this threshold for detecting rejection or cellular injury from ischemia was 100%. Elevated post-transplant DS cf-DNA returned to baseline within 5 days. Levels of DS cf-DNA at rejection were all above 1% (range 1.9% to 7.8%, P<0.002) and decreased to baseline with therapy in all cases (4/4, P<0.05). Further, surprisingly this example showed the ability to use the methods provided herein to determine the presence or absence of transplant rejection soon after transplant.

Accordingly, some embodiments provide a non-invasive method of assessing a risk in a recipient of the transplant. The method can comprise extracting a cf-DNA from a biological sample obtained from the recipient of the transplant. Cf-DNA can be extracted using any method known in the art or as provided in the Examples (see, e.g., Current Protocols in Molecular Biology, latest edition, or the QIAamp circulating nucleic acid kit or other appropriate commercially available kits). An exemplary method for isolating cf-DNA from blood is described. Blood containing an anti-coagulant such as EDTA or DTA is collected from a subject. The plasma, which contains cf-DNA, is separated from cells present in the blood (e.g., by centrifugation or filtering). An optional secondary separation may be performed to remove any remaining cells from the plasma (e.g., a second centrifugation or filtering step). The cf-DNA can then be extracted using any method known in the art, e.g., using a commercial kit such as those produced by Qiagen. Other exemplary methods for extracting cf-DNA are also known in the art (see, e.g., Cell-Free Plasma DNA as a Predictor of Outcome in Severe Sepsis and Septic Shock. Clin. Chem. 2008, v. 54, p. 1000-1007; Prediction of MYCN Amplification in Neuroblastoma Using Serum DNA and Real-Time Quantitative Polymerase Chain Reaction. JCO 2005, v. 23, p. 5205-5210; Circulating Nucleic Acids in Blood of Healthy Male and Female Donors. Clin. Chem. 2005, v. 51, p. 1317-1319; Use of Magnetic Beads for Plasma Cell-free DNA Extraction: Toward Automation of Plasma DNA Analysis for Molecular Diagnostics. Clin. Chem. 2003, v. 49, p. 1953-1955; Chiu R W K, Poon L L M, Lau T K, Leung T N, Wong E M C, Lo Y M D. Effects of blood-processing protocols on fetal and total DNA quantification in maternal plasma. Clin Chem 2001; 47:1607-1613; and Swinkels et al. Effects of Blood-Processing Protocols on Cell-free DNA Quantification in Plasma. Clinical Chemistry, 2003, vol. 49, no. 3, 525-526).

As used herein, "biological sample" is any sample that can be obtained from the subject from which cf-DNA can be extracted. Examples of such biological samples include whole blood, plasma, serum or urine. In some embodiments, addition of further nucleic acids, e.g., carrier RNA, to the biological sample is contemplated. The cf-DNA, in some embodiments, generally comprises DNA of the subject (e.g., a recipient of a transplant) and DNA not native to the subject (e.g., DNA of the donor of the transplant), with an increasing amount of the DNA not native to the subject (e.g., donor DNA) relative to the DNA of the subject, or total DNA, being indicative of a risk of and/or of the progression of an adverse condition in such a subject. As used herein, the "amount" refers to any quantitative value for the measurement of the DNA and can be given in an absolute or relative amount. Further, the amount can be a total amount, ratio, percentage, etc. As used herein, the term "level" can be used instead of "amount" but is intended to refer to the same types of values.

Generally, as provided herein, the amount, such as the percent, of total cf-DNA, or native cf-DNA, or cf-DNA not native to the subject (e.g., DS cf-DNA), can be indicative of the presence or absence of a risk associated with a condition, such as risk associated with a transplant, such as rejection, in the recipient or can be indicative of the need for further testing or surveillance. Some aspects of the disclosure relate to use of cell-free DNA, wherein the cell-free DNA comprises nucleic acids comprising first nucleic acids and second nucleic acids. In some embodiments, the first nucleic acids are of the subject (e.g., native cf-DNA). In some embodiments, the second nucleic acids are non-native cf-DNA (i.e., nucleic acids not native to the subject). Examples of second nucleic acids include, but are not limited to, cf-DNA from a transplanted organ (DS cf-DNA), or cf-DNA from a tumor/cancer (CS cf-DNA) or bacterial, fungal and/or viral DNA. The DNA may be analyzed to identify multiple loci, an allele of each of the loci may be determined and informative loci may be selected based on the determined alleles. As used herein, "loci" refer to nucleotide positions in a nucleic acid, e.g., a nucleotide position on a chromosome or in a gene. In some embodiments, a "loci" is a single nucleotide polymorphism. As used herein, "informative loci" refers to a locus where the genotype of the subject is homozygous for the major allele, while the genotype of the nucleic acid not native to the subject (e.g., the donor genotype or the tumor genotype) is homozygous or heterozygous for the minor allele. As used herein, "minor allele" refers to the allele that is less frequent in the population of nucleic acids for a locus. In some embodiments, the minor allele is the nucleotide identity at the locus in the nucleic acid not native to the subject (e.g., DS cf-DNA or CS cf-DNA). A "major allele", on the other hand, refers to the more frequent allele in a population. In some embodiments, the major allele is the nucleotide identity at the locus in the nucleic acid of the subject (e.g., host cf-DNA or non-cancerous cf-DNA). In some embodiments, the informative loci and alleles can be determined based on prior genotyping of the nucleic acids of the subject and the nucleic acids not native to the subject (e.g., the recipient and donor DNA, respectively). For example, the genotype of the recipient and donor are compared, and informative loci are identified as those loci where the recipient is homozygous for a nucleotide identity and the donor is heterozygous or homozygous for a different nucleotide identity. Methods for genotyping are well known in the art and further described herein. In this example, the minor and major allele may be identified by determining the relative quantities of each allele at the informative locus and/or may be identified as the nucleotide identity at the informative locus in the donor DNA (minor allele) and the recipient DNA (major allele). See Examples 1 and 2 for further details of an exemplary method for identifying informative loci and alleles. Accordingly, the methods provided can further include a step of genotyping the recipient and donor or genotyping the cancer and subject, or obtaining or being provided with such genotypes.

An estimated allele frequency, such as the estimated minor allele frequency, at the informative loci may then be calculated in a suitable manner. In some embodiments, the estimated allele frequency may be calculated based on modeling the number of counts of the allele, such as the minor allele, at the informative loci using a statistical distribution. For example, the estimated allele frequency can be calculated by modeling allele read counts using a binomial distribution. In some embodiments, the peak of such a distribution is determined and is indicative of the percent cf-DNA not native to the subject. A frequency of the minor allele at the informative loci may also be calculated using a maximum likelihood method. In some embodiments, the minor allele frequency (MAF) may be calculated with genotypes from plasma DNA of the subject, and genotypes not native to the subject (e.g., donor genotypes or tumor genotypes) for informative loci may be inferred using expectation maximization. In some embodiments, the read counts for the major and/or minor allele(s) can be corrected prior to estimating the allele frequency.

The determined amount of the cf-DNA (e.g., non-native cf-DNA, such as DS cf-DNA or CS cf-DNA) in the sample from the subject may then be used to determine a risk, such as rejection, associated with the transplant or risk associated with cancer. An increase or decrease above a threshold in the determined amount can indicate an increased or decreased risk in the subject. "Threshold" or "threshold value", as used herein, refers to any predetermined level or range of levels that is indicative of the presence or absence of a condition or the presence or absence of a risk. The threshold value can take a variety of forms. It can be single cut-off value, such as a median or mean. It can be established based upon comparative groups, such as where the risk in one defined group is double the risk in another defined group. It can be a range, for example, where the tested population is divided equally (or unequally) into groups, such as a low-risk group, a medium-risk group and a high-risk group, or into quadrants, the lowest quadrant being subjects with the lowest risk and the highest quadrant being subjects with the highest risk. The threshold value can depend upon the particular population selected. For example, an apparently healthy population will have a different 'normal' range. As another example, a threshold value can be determined from baseline values before the presence of a condition or risk or after a course of treatment. Such a baseline can be indicative of a normal or other state in the subject not correlated with the risk or condition that is being tested for. In some embodiments, the threshold value can be a baseline value of the subject being tested. Accordingly, the predetermined values selected may take into account the category in which the subject falls. Appropriate ranges and categories can be selected with no more than routine experimentation by those of ordinary skill in the art.

In some embodiments, such threshold is 1%, wherein a level above 1% is indicative of an increased risk and wherein a level at or below 1% is indicative of a decreased risk.

In some embodiments, where a non-native cf-DNA (e.g., DS cf-DNA) percentage is determined to be above a threshold value such as 1%, the method further comprises performing another test on the subject or biological sample. Such other tests can be any other test known by one of ordinary skill in the art to be useful in determining the presence or absence of a risk, e.g., in a transplant recipient. In some embodiments, the subject is a transplant recipient and the other test is a determination of the level of BNP and/or troponin in the transplant recipient. In other embodiments, the other test in addition to the level of BNP and/or troponin or in place thereof is an echocardiogram. In some embodiments, where the non-native cf-DNA (e.g., DS cf-DNA) percentage is determined to be less than a threshold value such as 1% no further testing is needed or recommended to the subject. While in some embodiments, it may be determined that there is an increased risk in the recipient when the amount of the DS cf-DNA obtained from the recipient is greater than 1%, although it should be appreciated that other thresholds may be utilized as embodiments of the invention are not limited in this respect.

In some embodiments, any of the methods provided herein may include an additional test(s) for assessing a condition, such as transplant rejection, transplant injury, and/or systemic disease; or cancer, metastasis, and/or recurrence. In some embodiments, the additional test(s) is for testing for or evaluating a bacterial, fungal and/or viral infection. In some embodiments, the additional test may be a test associated with assessment of transplant risk. Exemplary additional tests for transplant recipients include, but are not limited to, a biopsy (e.g., an endomyocardial biopsy (EMB)), blood sugar level test, urine level test, abdominal CT scan, chest x-ray, heart echocardiography, kidney arteriography, kidney ultrasound, kidney function tests (e.g., creatinine in blood and/or urine or blood urea nitrogen), or liver function tests (e.g., albumin, aspartate transaminase, transaminitis, alkaline phosphotase, bilirubin, and/or gamma glutamyl transpeptidase). The type of additional test(s) will depend upon the transplanted organ (heart, lung, liver, kidney, etc.) and is well within the determination of the skilled artisan. Exemplary additional tests for subjects suspected of having cancer, metastasis, and/or recurrence, include, but are not limited to, biopsy (e.g., fine-needle aspiration, core biopsy, or lymph node removal), X-ray, CT scan, ultrasound, MRI, endoscopy, circulating tumor cell levels, complete blood count, detection of specific tumor biomarkers (e.g., EGFR, ER, HER2, KRAS, c-KIT, CD20, CD30, PDGFR, BRAF, or PSMA), and/or genotyping (e.g., BRCA1, BRCA2, HNPCC, MLH1, MSH2, MSH6, PMS1, or PMS2). The type of additional test(s) will depend upon the type of suspected cancer/metastasis/recurrence and is well within the determination of the skilled artisan.

The inventors have surprisingly discovered that DS cf-DNA may be detected in a transplant recipient within 10 days following the transplantation. The ability to detect transplant risk so early, and with a non-invasive method, can offer early intervention and better patient outcomes. In some embodiments, the methods provided herein are performed on a transplant recipient as early as 14-36 hours after transplant. In other embodiment, the methods can be performed within 84-126 hours after transplant. In still other embodiments, the methods can be performed within 160-206 hours after transplant. In yet other embodiments, the methods are performed within 3, 5, 7, 10, 14, 21, 30, 40, 50, or 60 days after transplant. The amount of non-native cf-DNA, such as DS cf-DNA, or total cf-DNA or native cf-DNA, may also be determined at any other time following the transplant, and may be utilized for short- or long-term surveillance. The determination may be performed instead of or in addition to EMB or other tests.

It was observed that the percentage of non-native cf-DNA (e.g., donor-specific DNA) can decrease or even decrease to a near baseline level in recipients upon initiation of a therapy, such as an anti-rejection therapy. Accordingly, as provided herein the methods provided can include the step of providing a therapy, such as an anti-rejection therapy, or providing information regarding therapies, to the transplant recipient where the amount, such as the percent, of non-native cf-DNA, is above a certain threshold value, such as 1%. In some embodiments, the information includes written materials containing the information. Written materials can include the written information in electronic form.

Therapies can include anti-rejection therapies. Anti-rejection therapies include, for example, the administration of an immunosuppressive to the transplant recipient. Immunosuppressives include, but are not limited to, corticosteroids (e.g., prednisolone or hydrocortisone), glucocorticoids, cytostatics, alkylating agents (e.g., nitrogen mustards (cyclophosphamide), nitrosoureas, platinum compounds, cyclophosphamide (Cytoxan)), antimetabolites (e.g., folic acid analogues, such as methotrexate, purine analogues, such as azathioprine and mercaptopurine, pyrimidine analogues, and protein synthesis inhibitors), cytotoxic antibiotics (e.g., dactinomycin, anthracyclines, mitomycin C, bleomycin, mithramycin), antibodies (e.g., anti-CD20, anti-IL-1, anti-IL-2Ralpha, anti-T-cell or anti-CD-3 monoclonals and polyclonals, such as Atgam, and Thymoglobuline), drugs acting on immunophilins, ciclosporin, tacrolimus, sirolimus, interferons, opiods, TNF-binding proteins, mycophenolate, fingolimod and myriocin. In some embodiments, anti-rejection therapy comprises blood transfer or marrow transplant. Therapies can also include therapies for treating systemic conditions, such as sepsis. The therapy for sepsis can include intravenous fluids, antibiotics, surgical drainage, early goal directed therapy (EGDT), vasopressors, steroids, activated protein C, drotrecogin alfa (activated), oxygen and appropriate support for organ dysfunction. This may include hemodialysis in kidney failure, mechanical ventilation in pulmonary dysfunction, transfusion of blood products, and drug and fluid therapy for circulatory failure. Ensuring adequate nutrition—preferably by enteral feeding, but if necessary by parenteral nutrition—can also be included particularly during prolonged illness. Other associate therapies can include insulin and medication to prevent deep vein thrombosis and gastric ulcers. Therapies for treating a recipient of a transplant can also include therapies for treating a bacterial, fungal and/or viral infection. Such therapies are known to those of ordinary skill in the art.

Similarly, the therapies can be therapies for treating cancer, a tumor or metastasis, such as an anti-cancer therapy. Such therapies include, but are not limited to, antitumor agents, such as docetaxel; corticosteroids, such as prednisone or hydrocortisone; immunostimulatory agents; immunomodulators; or some combination thereof. Antitumor agents include cytotoxic agents, chemotherapeutic agents and agents that act on tumor neovasculature. Cytotoxic agents include cytotoxic radionuclides, chemical toxins and protein toxins. The cytotoxic radionuclide or radiotherapeutic isotope can be an alpha-emitting or beta-emitting. Cytotoxic radionuclides can also emit Auger and low energy electrons. Suitable chemical toxins or chemotherapeutic agents include members of the enediyne family of molecules, such as calicheamicin and esperamicin. Chemical toxins can also be taken from the group consisting of methotrexate, doxorubicin, melphalan, chlorambucil, ARA-C, vindesine, mitomycin C, cis-platinum, etoposide, bleomycin and 5-fluorouracil. Other antineoplastic agents include dolastatins (U.S. Pat. Nos. 6,034,065 and 6,239,104) and derivatives thereof. Toxins also include poisonous lectins, plant toxins such as ricin, abrin, modeccin, botulina and diphtheria toxins. Other chemotherapeutic agents are known to those skilled in the art. Examples of cancer chemotherapeutic agents include, but are not limited to, irinotecan (CPT-11); erlotinib; gefitinib (Iressa™); imatinib mesylate (Gleevec); oxalipatin; anthracyclins-idarubicin and daunorubicin; doxorubicin; alkylating agents such as melphalan and chlorambucil; cis-platinum, methotrexate, and alkaloids such as vindesine and vinblastine. In some embodiments, further or alternative cancer treatments are contemplated herein, such as radiation and/or surgery.

Administration of a treatment or therapy may be accomplished by any method known in the art (see, e.g., Harrison's Principle of Internal Medicine, McGraw Hill Inc.). Preferably, administration of a treatment or therapy occurs in a therapeutically effective amount. Administration may be local or systemic. Administration may be parenteral (e.g., intravenous, subcutaneous, or intradermal) or oral. Compositions for different routes of administration are well known in the art (see, e.g., Remington's Pharmaceutical Sciences by E. W. Martin).

As used herein, "a therapeutically effective amount" is an amount sufficient to provide a medically desirable result, such as treatment of transplant rejection, treatment of systemic disease, or treatment of cancer. The effective amount will vary with the particular condition being treated, the age and physical condition of the subject being treated, the severity of the condition, the duration of the treatment, the nature of any concurrent therapy, the specific route of administration and the like factors within the knowledge and expertise of the health practitioner. For administration to a subject such as a human, a dosage of from about 0.001, 0.01, 0.1, or 1 mg/kg up to 50, 100, 150, or 500 mg/kg or more can typically be employed. When administered, a treatment or therapy may be applied in pharmaceutically-acceptable amounts and in pharmaceutically-acceptable compositions. Such preparations may routinely contain salt, buffering agents, preservatives, compatible carriers, and optionally other therapeutic agents.

In some embodiments, the amount of non-native cf-DNA (e.g., DS cf-DNA) or total cf-DNA or native cf-DNA in the sample from the recipient may be used to evaluate an effect of a therapy, such as an anti-rejection therapy, sepsis therapy, therapy for treating a bacterial, fungal and/or viral infection or anti-cancer therapy on the subject (e.g., the recipient of the transplant) by correlating a decreased amount of the non-native cf-DNA or total cf-DNA or native cf-DNA in the subject with a positive effect of the therapy. A suitable therapy may be selected based on the correlation and/or the amount of the therapy administered to the subject may be increased or decreased also based such a correlation. Choice of therapies and dosing involved with such therapies are within the skill in those in the art.

It should be appreciated that the described techniques of determining an amount of cf-DNA may be used for any non-invasive method of assessing a risk in a recipient of a transplant. The method may be employed over any period of time after the transplantation. The described methods of assessing a risk in a recipient of a transplant may be implemented in any suitable manner. For example, the method may be implemented as described below in connection with Examples 1, 2 and/or any of the Figures. The method may be any of the methods provided herein, including those in the Examples and in the Figures.

It should also be appreciated that a Predictive Model (e.g., as in Formula 1, 2 or 3) can also be used to assess risk in a subject, such as a recipient of a transplant rejection, and/or outcome, and such methods are also provided. It was found, as described in more detail in Example 2, that a formula based on the times, such as hours, from clamp removal, recipient and donor weight, and concentration of DS cf-DNA is significantly correlated with the length of hospital stay and consistent with donor organ injury. Thus, methods are provided herein where the amount of non-native cf-DNA is determined and the result of Formula 1, 2 and/or 3 is calculated.

Predictive Model(Formula 1)=time post initiation of therapy(e.g., surgical or pharmaceutical)×non-native cf-DNA Predictive Model(Formula 2)=time post-clamp removal×(recipient weight/donor weight)×donor-specific cell-free DNA Predictive Model(Formula 3)=time post initiation of a therapy×(recipient weight/donor weight)×non-native cell-free DNA In some embodiments, the Predictive Model (e.g., Formula 1, 2 or 3) is used assuming a constant plasma clearance rate.

The methods provided can further comprise performing another test on the subject based on the comparison or result, such as the outcome of the Predictive Model (e.g., Formula 1, 2 or 3) (e.g., by comparison of the result with one or more threshold values). Such other tests can be any other test known by one of ordinary skill in the art useful in determining the presence or absence of a risk in a subject, such as a transplant recipient, and/or the outcome for such a subject. In some embodiments, the other test is a determination of the level of BNP and/or troponin in a transplant recipient. In other embodiments, the other test in addition to the level of BNP and/or troponin or in place thereof is an echocardiogram. In still other embodiments, the other test can be any of the other methods provided herein.

In other embodiments, the methods can include the step of providing a therapy, such as an anti-rejection therapy or anti-cancer therapy, or providing information regarding a therapy, to the transplant recipient or subject having or suspected of having cancer when the result is above a certain threshold value. In still other embodiments, the methods can be used to assess the efficacy of a therapy, such as an anti-rejection therapy or anti-cancer therapy, in a transplant recipient or subject having or suspected of having cancer where improved values can indicate less of a need for the therapy, while worsening values can indicate the need for a therapy, a different therapy, or an increased amount of a therapy. The methods provided herein can include the step of evaluating the need or dose of a therapy in a transplant recipient based on the result of a comparison with a threshold value or a value determined from a Predictive Model (e.g., Formula 1, 2 or 3), etc. at one time point or over time.

In yet other embodiment, the methods can include predicting the likely clinical course based on the determined amount of the cell-free DNA not native to the subject. In some embodiments, when the subject is a recipient of a transplant predicting the likely clinical course comprises predicting a length of hospital stay after the subject receives the transplant, the likelihood of mortality or the likelihood of a problem with the transplant. In some embodiments, when the subject is a having or suspected of having cancer, predicting the likely clinical course comprises predicting the likelihood of mortality. In some embodiments, a course of action is selected for the subject or information about a course of action is provided to the subject based on the likely predicted clinical course.

The cf-DNA, such as DS cf-DNA, can be determined using any of the methods provided herein, including those in the Examples or the Figures, or that would be otherwise apparent to one of ordinary skill in the art. The DNA may be analyzed using any suitable next generation or high-throughput sequencing and/or genotyping technique, such as those provided herein. Examples of next generation and high-throughput sequencing and/or genotyping techniques include, but are not limited to, massively parallel signature sequencing, polony sequencing, 454 pyrosequencing, illumina (Solexa) sequencing, SOLiD sequencing, ion semiconductor sequencing, DNA nanoball sequencing, heliscope single molecule sequencing, single molecule real time (SMRT) sequencing, MassARRAY®, and Digital Analysis of Selected Regions (DANSR™) (see, e.g., Stein R A (1 Sep. 2008). "Next-Generation Sequencing Update". Genetic Engineering & Biotechnology News 28 (15); Quail, Michael; Smith, Miriam E; Coupland, Paul; Otto, Thomas D; Harris, Simon R; Connor, Thomas R; Bertoni, Anna; Swerdlow, Harold P; Gu, Yong (1 Jan. 2012). "A tale of three next generation sequencing platforms: comparison of Ion torrent, pacific biosciences and illumina MiSeq sequencers". BMC Genomics 13 (1): 341; Liu, Lin; Li, Yinhu; Li, Siliang; Hu, Ni; He, Yimin; Pong, Ray; Lin, Danni; Lu, Lihua; Law, Maggie (1 Jan. 2012). "Comparison of Next-Generation Sequencing Systems". Journal of Biomedicine and Biotechnology 2012: 1-11; Qualitative and quantitative genotyping using single base primer extension coupled with matrix-assisted laser desorption/ionization time-of-flight mass spectrometry (MassARRAY®). Methods Mol Biol. 2009; 578: 307-43; Chu T, Bunce K, Hogge W A, Peters D G. A novel approach toward the challenge of accurately quantifying fetal DNA in maternal plasma. Prenat Diagn 2010; 30:1226-9; and Suzuki N, Kamataki A, Yamaki J, Homma Y. Characterization of circulating DNA in healthy human plasma. Clinica chimica acta; international journal of clinical chemistry 2008; 387:55-8).

Aspects of the disclosure relate to assessing risk in a subject. The term subject and patient may be used interchangeably herein. In some embodiments, the subject is a transplant recipient. In some embodiments, the transplant recipient is a pediatric transplant recipient. In some embodiments, the subject may show no signs or symptoms of having a transplant complication or condition, such as systemic disease, transplant rejection, bacterial, fungal and/ or viral infection and/or transplant injury. However, in some embodiments, the subject may show symptoms associated with such conditions, such as decrease of the transplanted organs function, pain or swelling in the area of the organ, fever, flu-like symptoms, and/or discomfort. Though the examples described herein pertain to assessing a risk associated with a heart transplant, risk associated with any transplant may be monitored using the described techniques as embodiments are not limited in this respect. Therefore, the transplant may be of any other solid organs, such as the kidneys, liver, lungs, pancreas, stomach, etc. The recipient may be an adult or a pediatric recipient.

As mentioned above, any of the methods provided can be performed on a subject with or at risk of having cancer or a tumor, recurrence of cancer or a tumor or metastasis of a cancer or tumor. Accordingly, in some embodiments, the subject is a subject suspected of having cancer, metastasis, and/or recurrence of cancer or subject having cancer, metastasis and/or recurrence of cancer. In some embodiments, the subject may show no signs or symptoms of having a cancer, metastasis, and/or recurrence. However, in some embodiments, the subject may show symptoms associated with cancer. The type of symptoms will depend upon the type of cancer and are well known in the art. Cancers include, but are not limited to, leukemias, lymphomas, myelomas, carcinomas, metastatic carcinomas, sarcomas, adenomas, nervous system cancers and geritourinary cancers. Exemplary cancers include, but are not limited to, adult and pediatric acute lymphoblastic leukemia, acute myeloid leukemia, adrenocortical carcinoma, AIDS-related cancers, anal cancer, cancer of the appendix, astrocytoma, basal cell carcinoma, bile duct cancer, bladder cancer, bone cancer, osteosarcoma, fibrous histiocytoma, brain cancer, brain stem glioma, cerebellar astrocytoma, malignant glioma, ependymoma, medulloblastoma, supratentorial primitive neuroectodermal tumors, hypothalamic glioma, breast cancer, male breast cancer, bronchial adenomas, Burkitt lymphoma, carcinoid tumor, carcinoma of unknown origin, central nervous system lymphoma, cerebellar astrocytoma, malignant glioma, cervical cancer, childhood cancers, chronic lymphocytic leukemia, chronic myelogenous leukemia, chronic myeloproliferative disorders, colorectal cancer, cutaneous T-cell lymphoma, endometrial cancer, ependymoma, esophageal cancer, Ewing family tumors, extracranial germ cell tumor, extragonadal germ cell tumor, extrahepatic bile duct cancer, intraocular melanoma, retinoblastoma, gallbladder cancer, gastric cancer, gastrointestinal stromal tumor, extracranial germ cell tumor, extragonadal germ cell tumor, ovarian germ cell tumor, gestational trophoblastic tumor, glioma, hairy cell leukemia, head and neck cancer, hepatocellular cancer, Hodgkin lymphoma, non-Hodgkin lymphoma, hypopharyngeal cancer, hypothalamic and visual pathway glioma, intraocular melanoma, islet cell tumors, Kaposi sarcoma, kidney cancer, renal cell cancer, laryngeal cancer, lip and oral cavity cancer, small cell lung cancer, non-small cell lung cancer, primary central nervous system lymphoma, Waldenstrom macroglobulinema, malignant fibrous histiocytoma, medulloblastoma, melanoma, Merkel cell carcinoma, malignant mesothelioma, squamous neck cancer, multiple endocrine neoplasia syndrome, multiple myeloma, mycosis fungoides, myelodysplastic syndromes, myeloproliferative disorders, chronic myeloproliferative disorders, nasal cavity and paranasal sinus cancer, nasopharyngeal cancer, neuroblastoma, oropharyngeal cancer, ovarian cancer, pancreatic cancer, parathyroid cancer, penile cancer, pharyngeal cancer, pheochromocytoma, pineoblastoma and supratentorial primitive neuroectodermal tumors, pituitary cancer, plasma cell neoplasms, pleuropulmonary blastoma, prostate cancer, rectal cancer, rhabdomyosarcoma, salivary gland cancer, soft tissue sarcoma, uterine sarcoma, Sezary syndrome, non-melanoma skin cancer, small intestine cancer, squamous cell carcinoma, squamous neck cancer, supratentorial primitive neuroectodermal tumors, testicular cancer, throat cancer, thymoma and thymic carcinoma, thyroid cancer, transitional cell cancer, trophoblastic tumors, urethral cancer, uterine cancer, uterine sarcoma, vaginal cancer, vulvar cancer, and Wilms tumor. In some embodiments, the cancer is prostate cancer, bladder cancer, pancreatic cancer, lung cancer, kidney cancer, breast cancer, or colon cancer.

Figure 9:
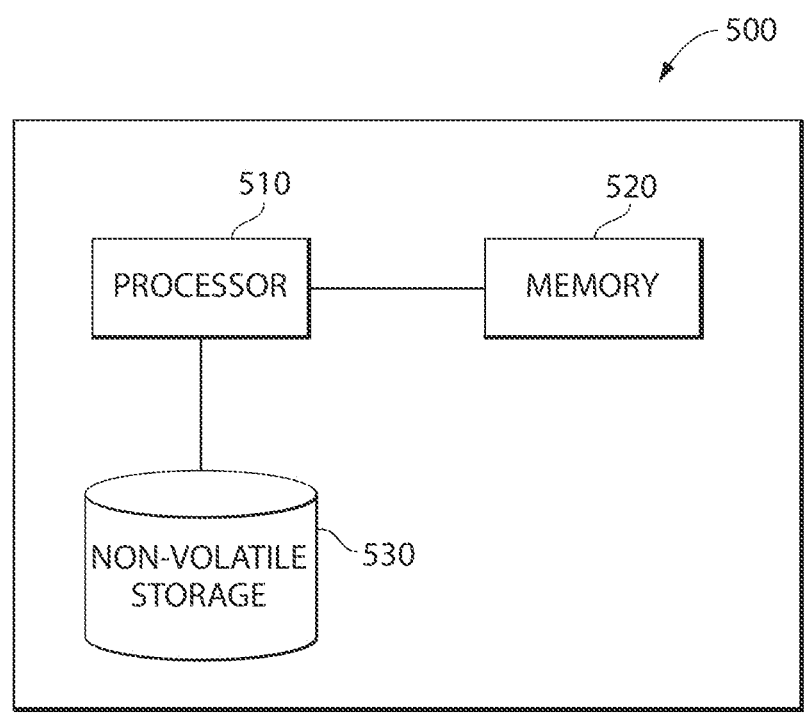
FIG. 9 is a schematic of an illustrative implementation of a computer system that may be used in connection with any of the embodiments of the invention.
Figure 10:
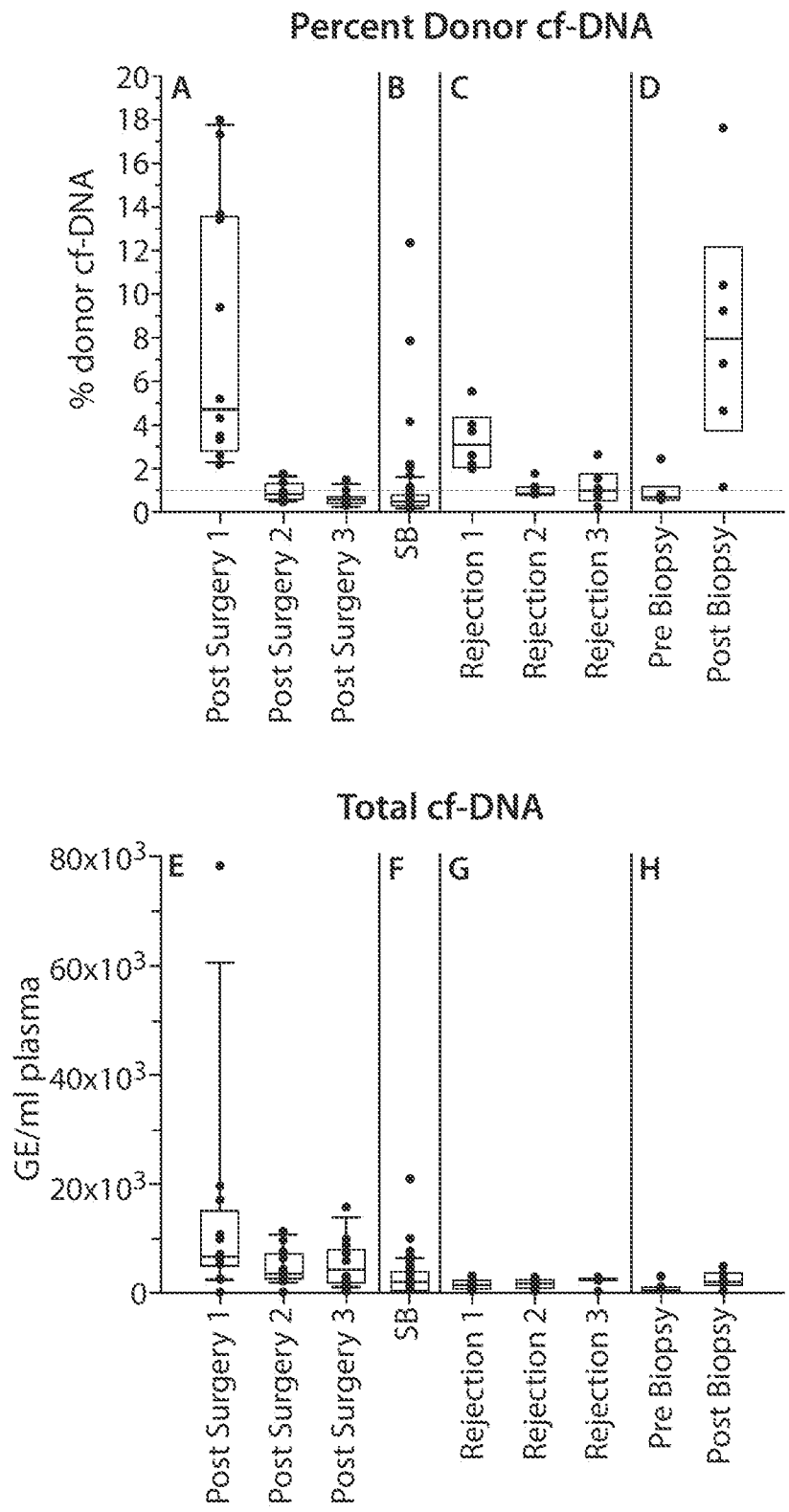
FIG. 10 is a series of bar graphs showing the percent DS cf-DNA (A-D) and T cf-DNA (E-H) at three time points post-surgery, in a surveillance biopsy, at 3 times points during rejection, and pre- and post-biopsy.
Figure 11:
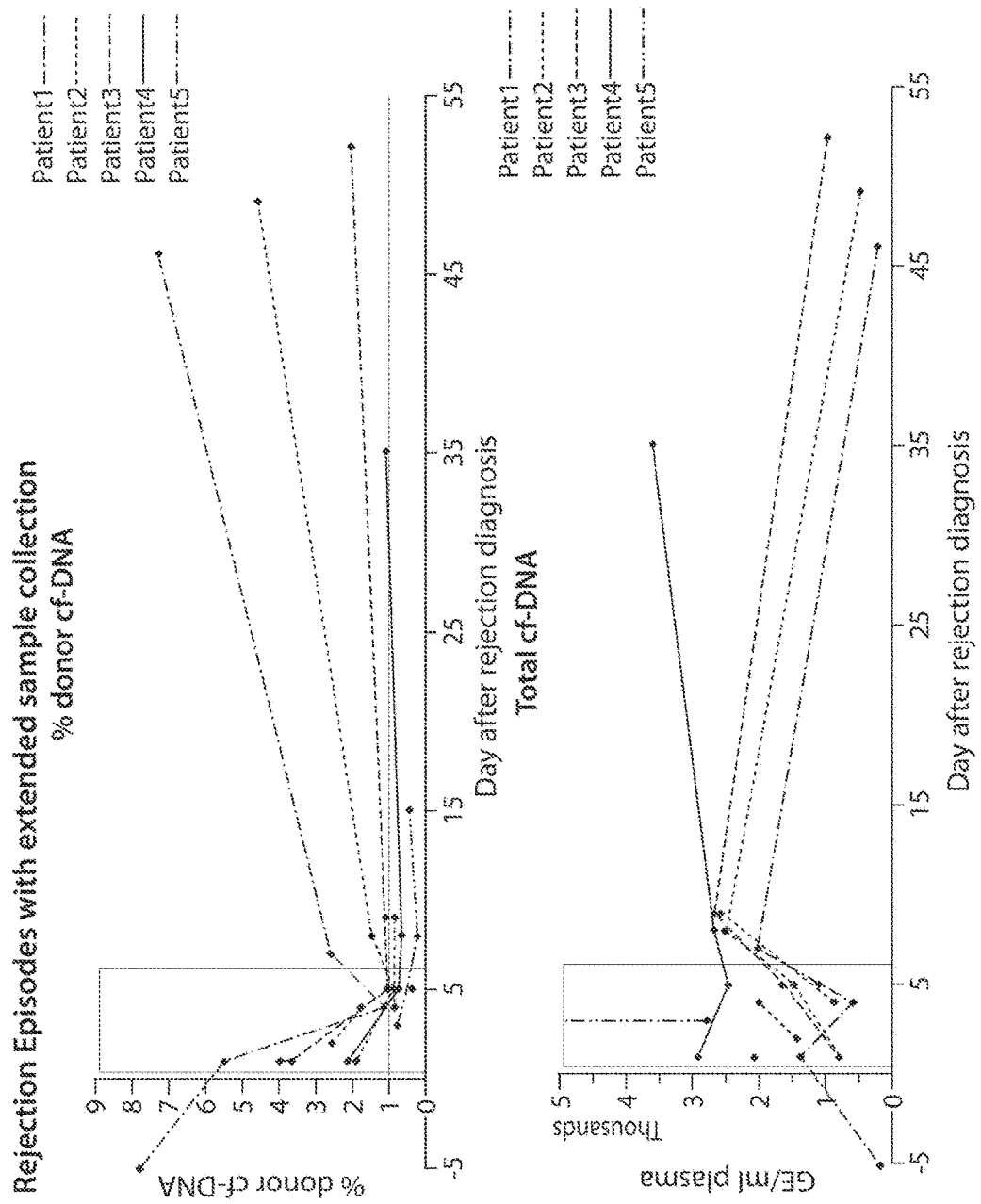
FIG. 11 is a series of graphs showing percent DS cf-DNA and T cf-DNA (GE/mL) during rejection episodes with extended sample collection in five patients.
Figure 12:
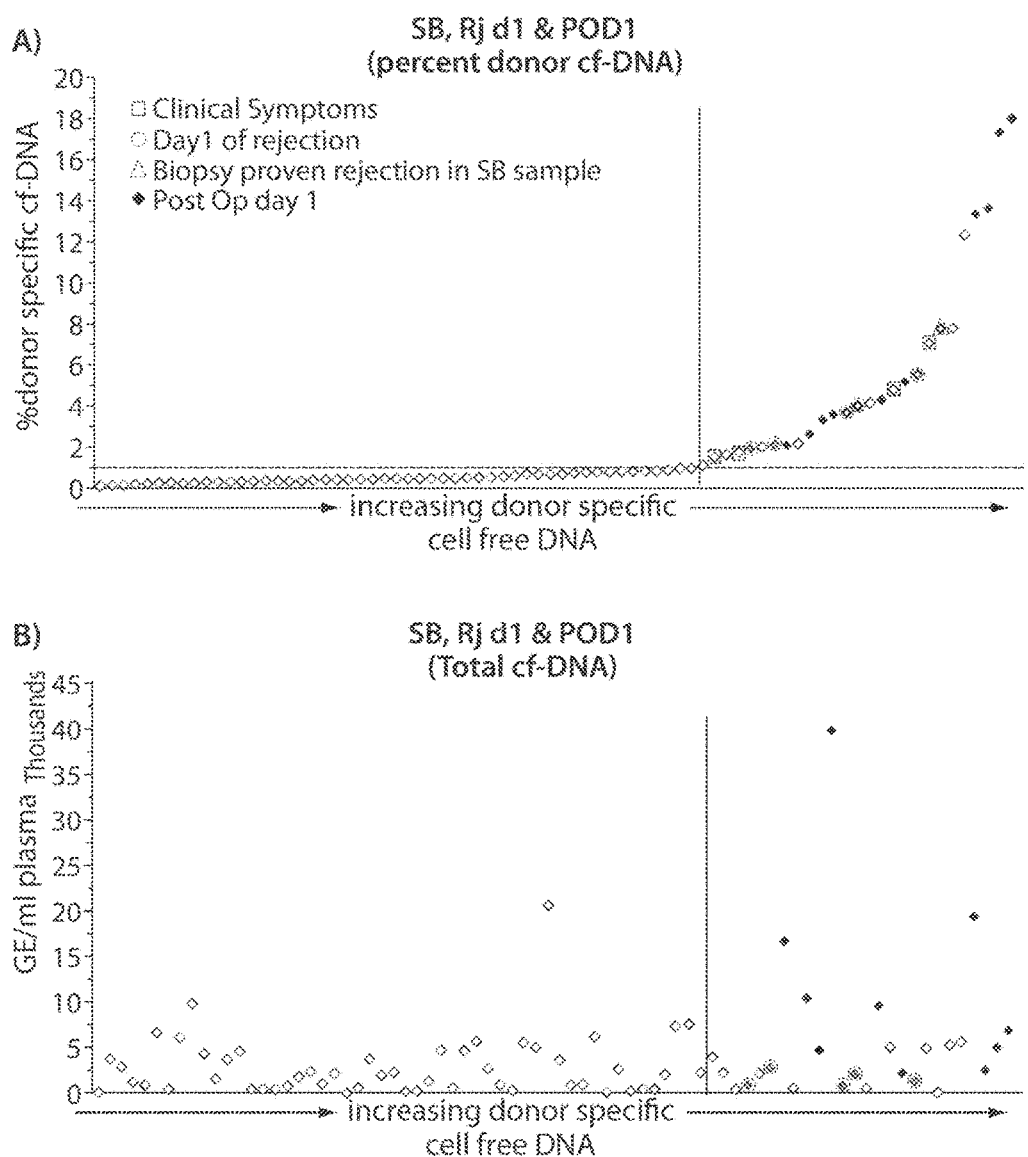
FIG. 12 is a series of graphs showing percent DS cf-DNA (A) and T cf-DNA (B) (GE/mL) in samples from surveillance biopsy (SB), on the day of clinical diagnosis of rejection (Rj D1) and post-operation day 1 (POD1) in several patients.
Figure 13:
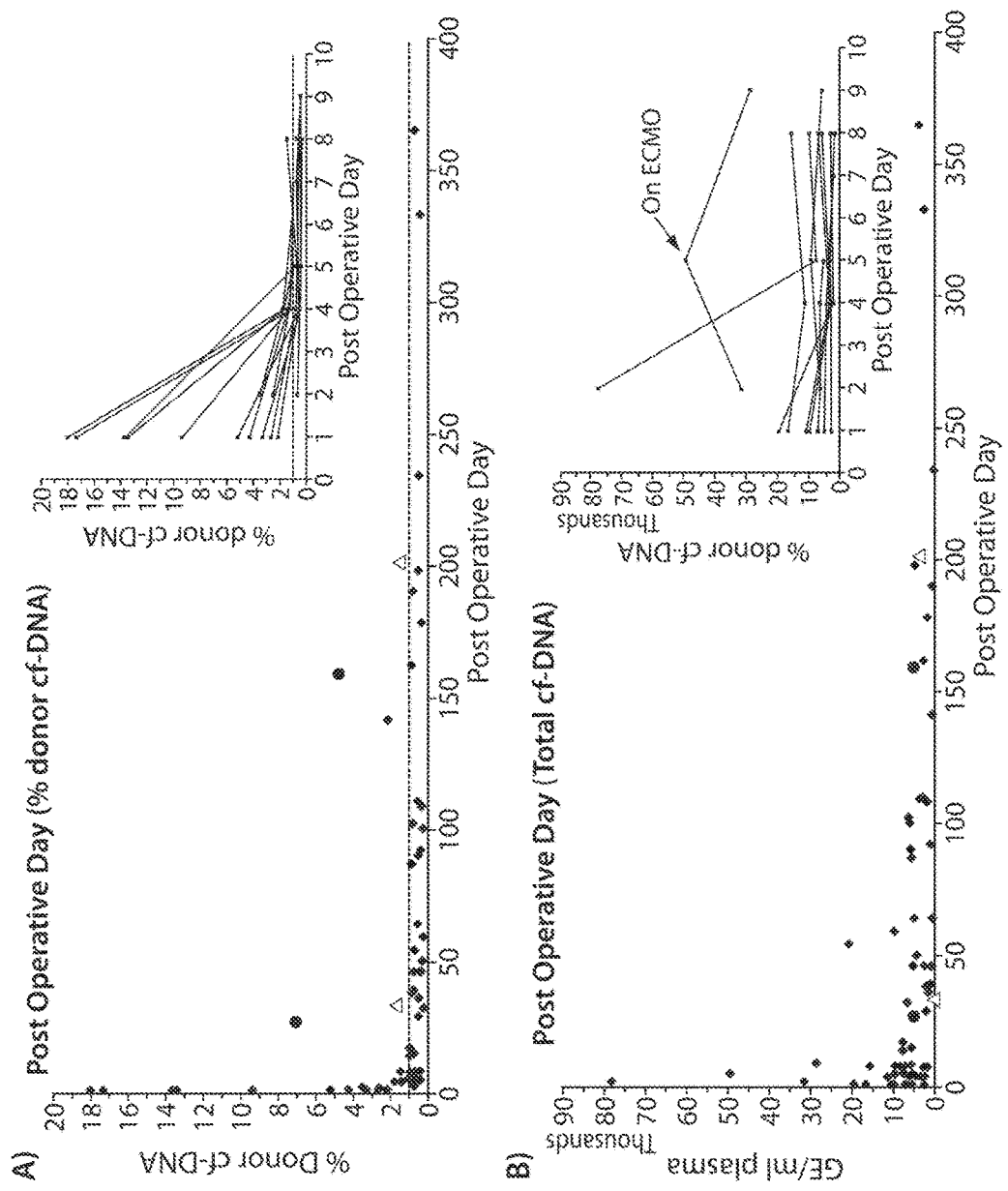
FIG. 13 is a series of graphs showing percent DS cf-DNA (A) and T cf-DNA (B) in samples collected on different post-operative days in patients.
Figure 14:
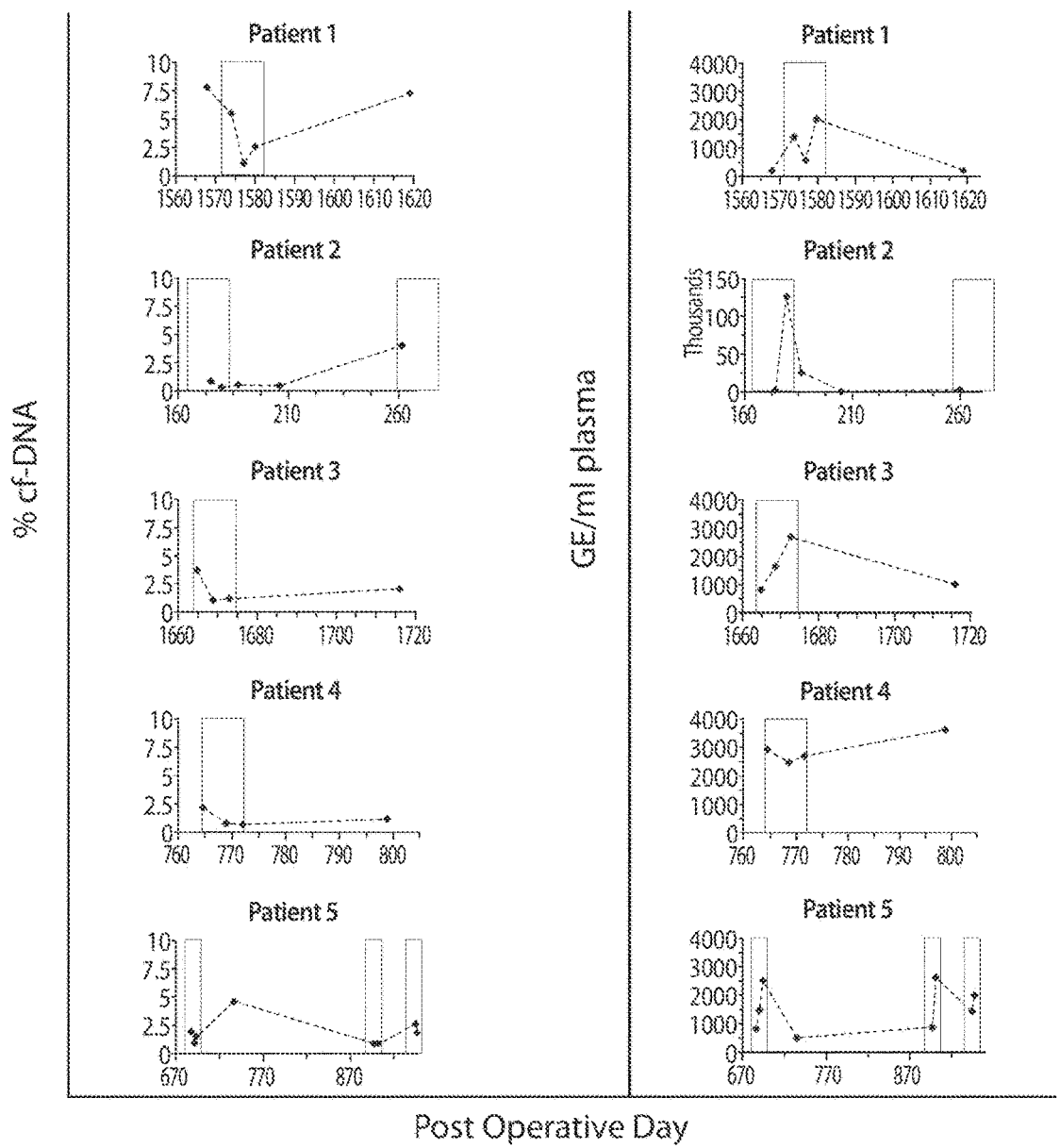
FIG. 14 is a series of graphs showing percent DS cf-DNA and T cf-DNA (GE/mL) in samples collected on different post-operative days in patients.
Figure 17:
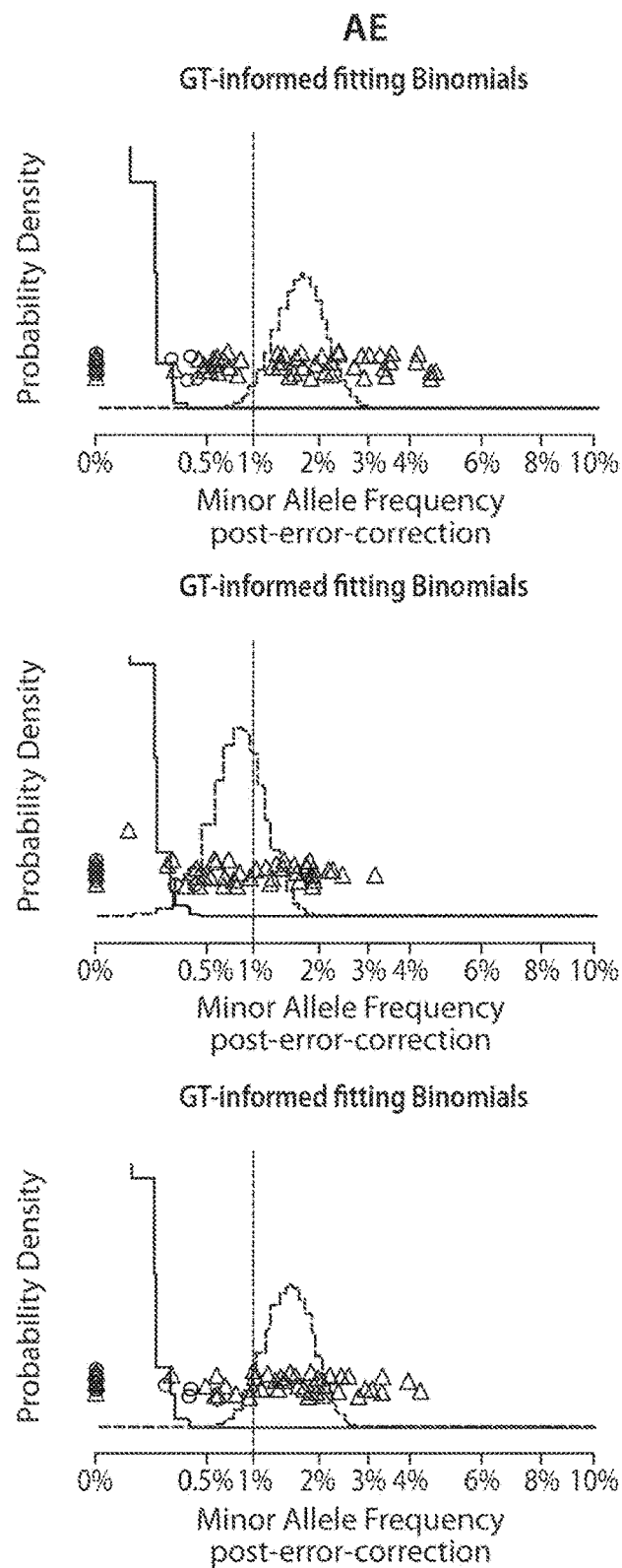
FIG. 17 is a series of graphs of minor allele frequencies post-error correction.
Figure 17:
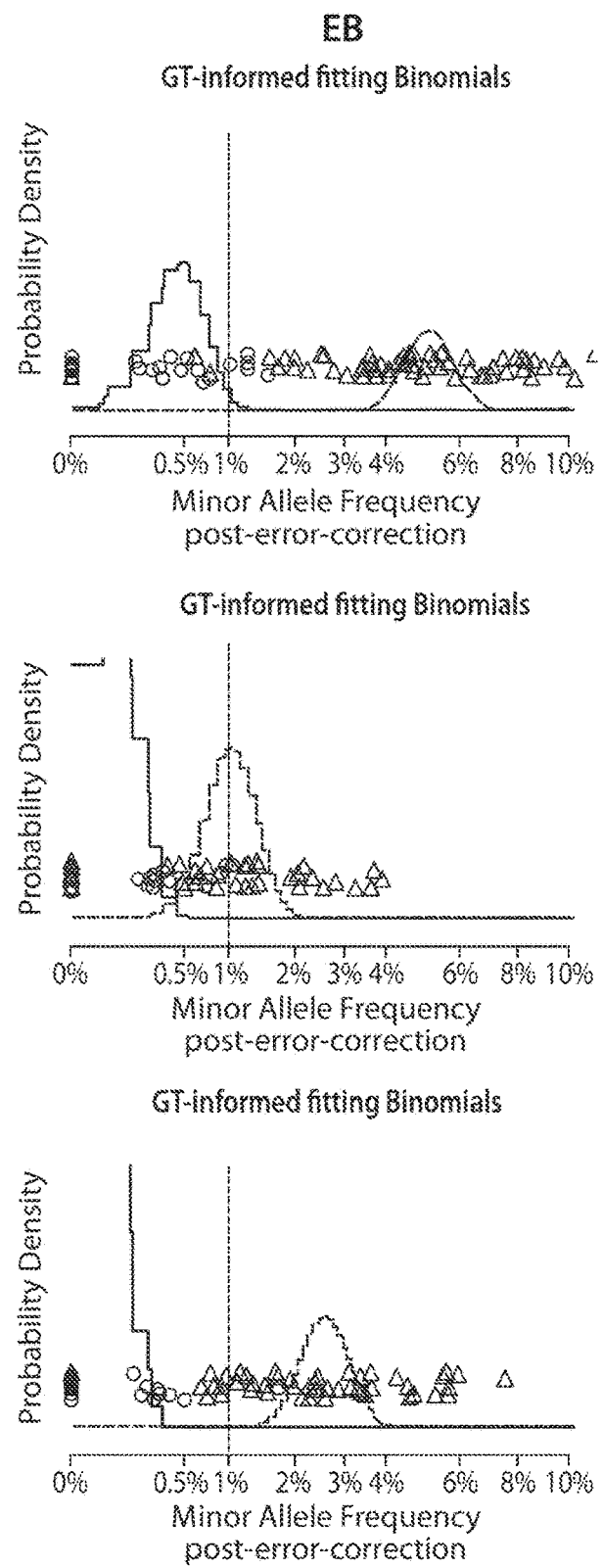
Figure 17:
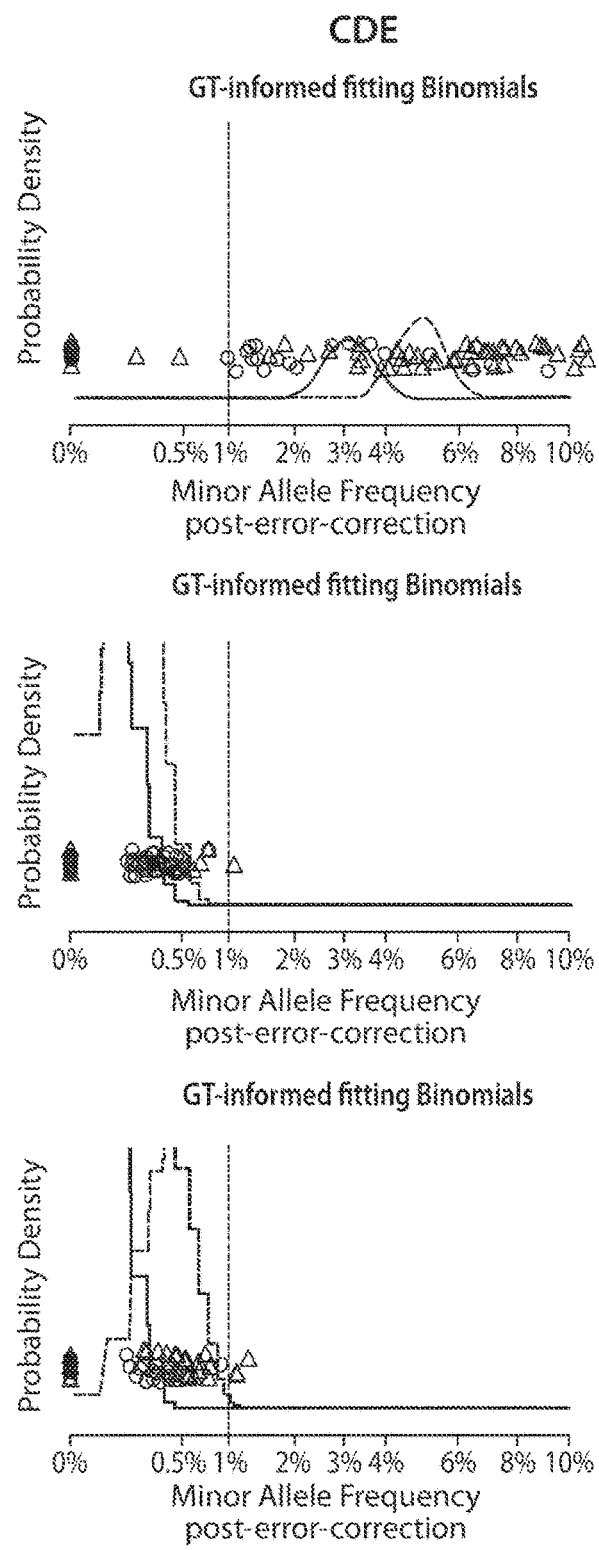
Figure 17:
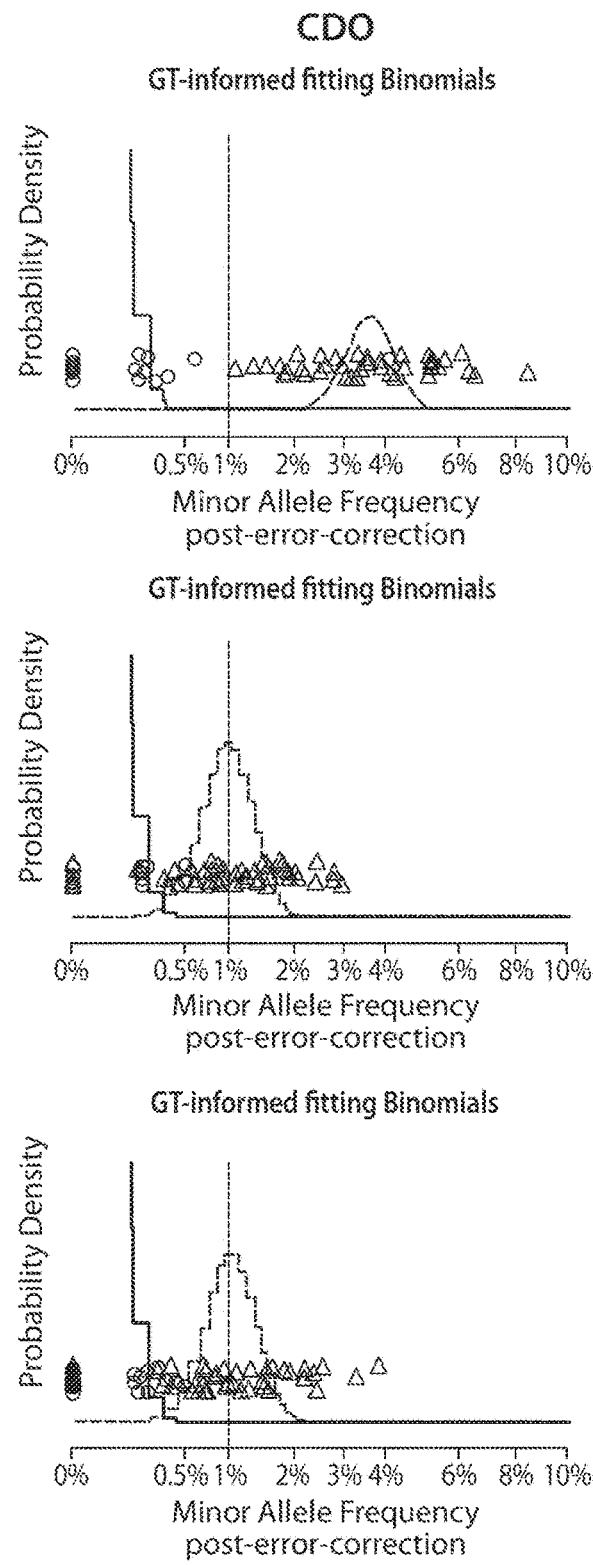
Figure 18:
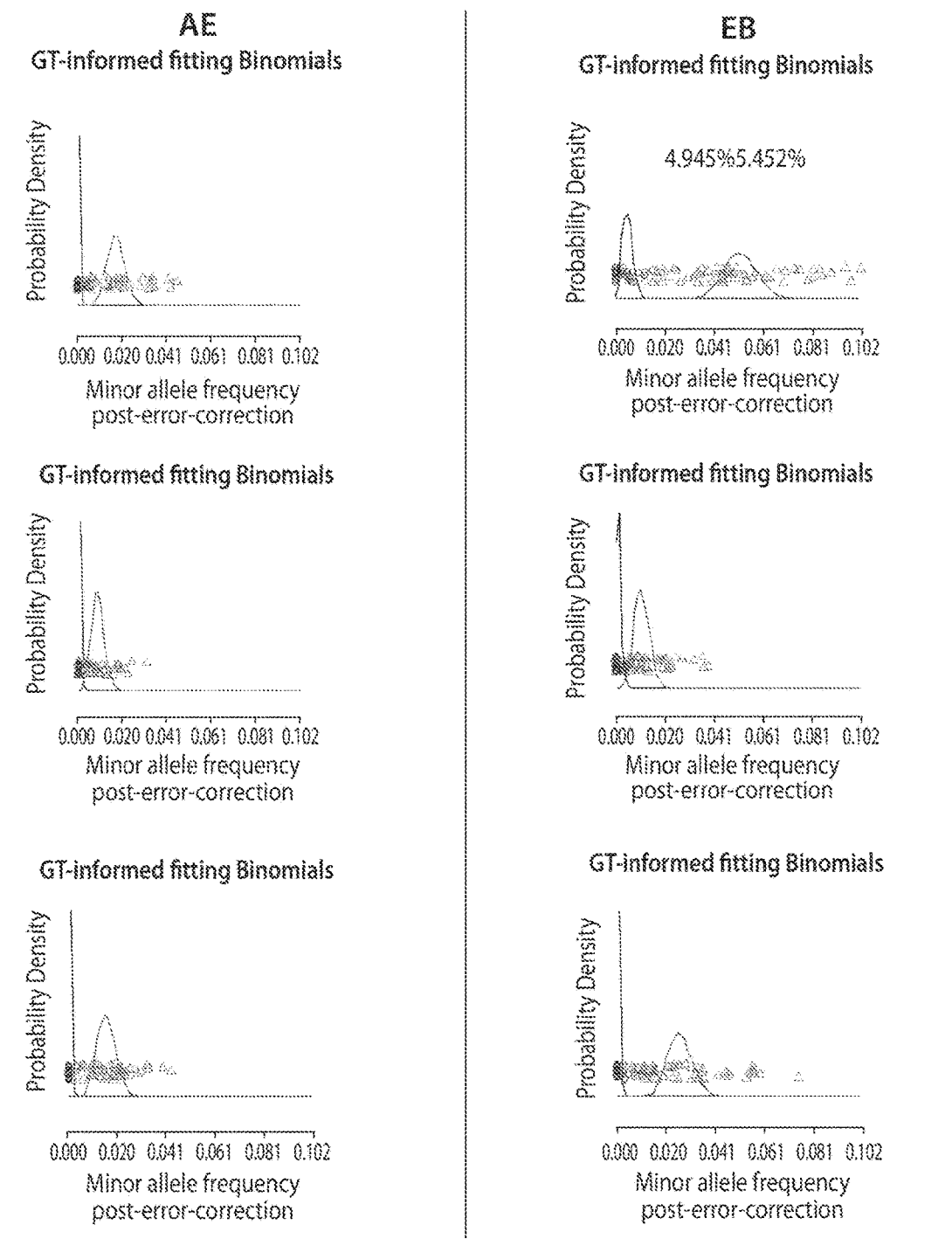
FIG. 18 is a series of graphs of minor allele frequencies post-error correction in SB samples.
Figure 18:
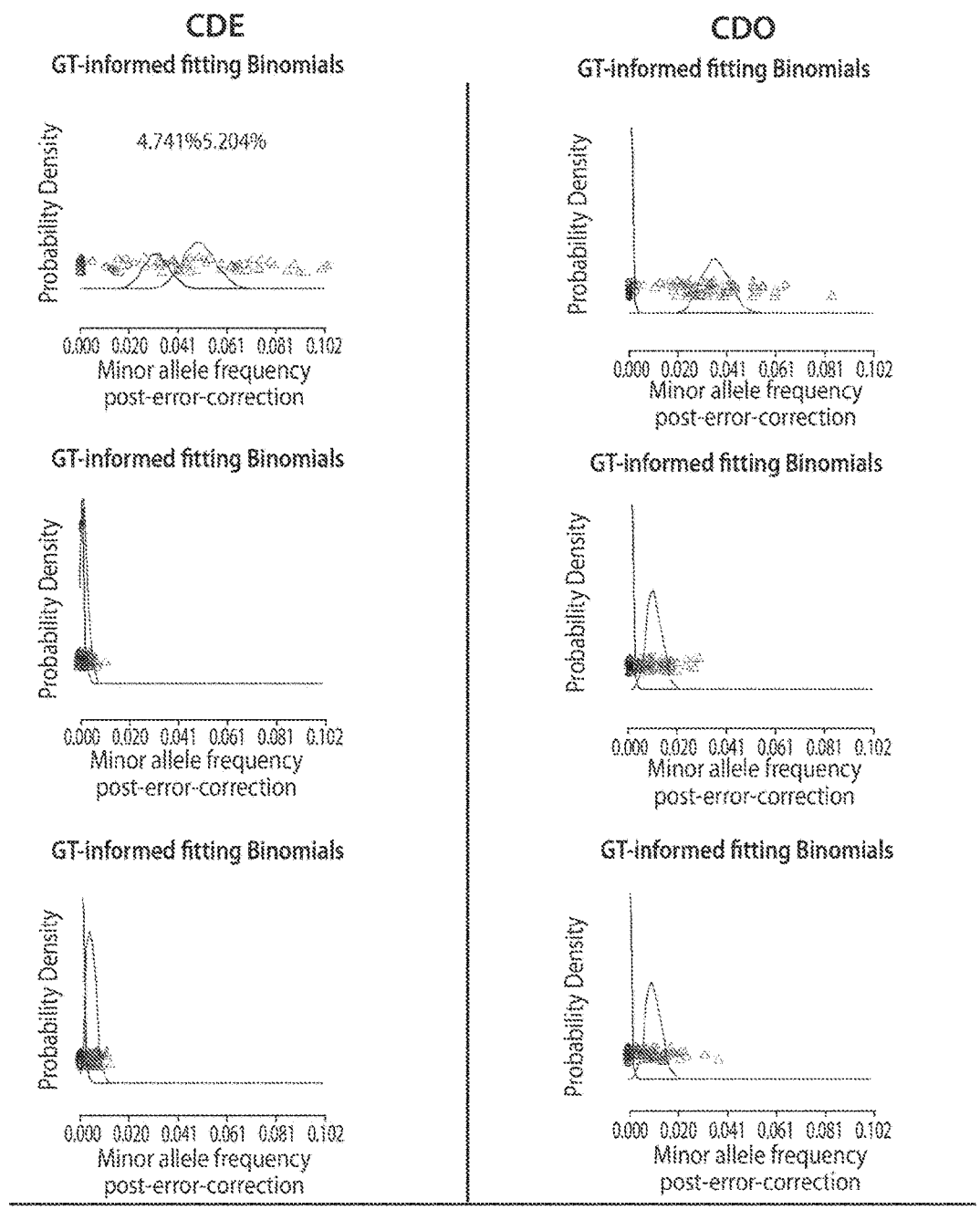
Figure 18:
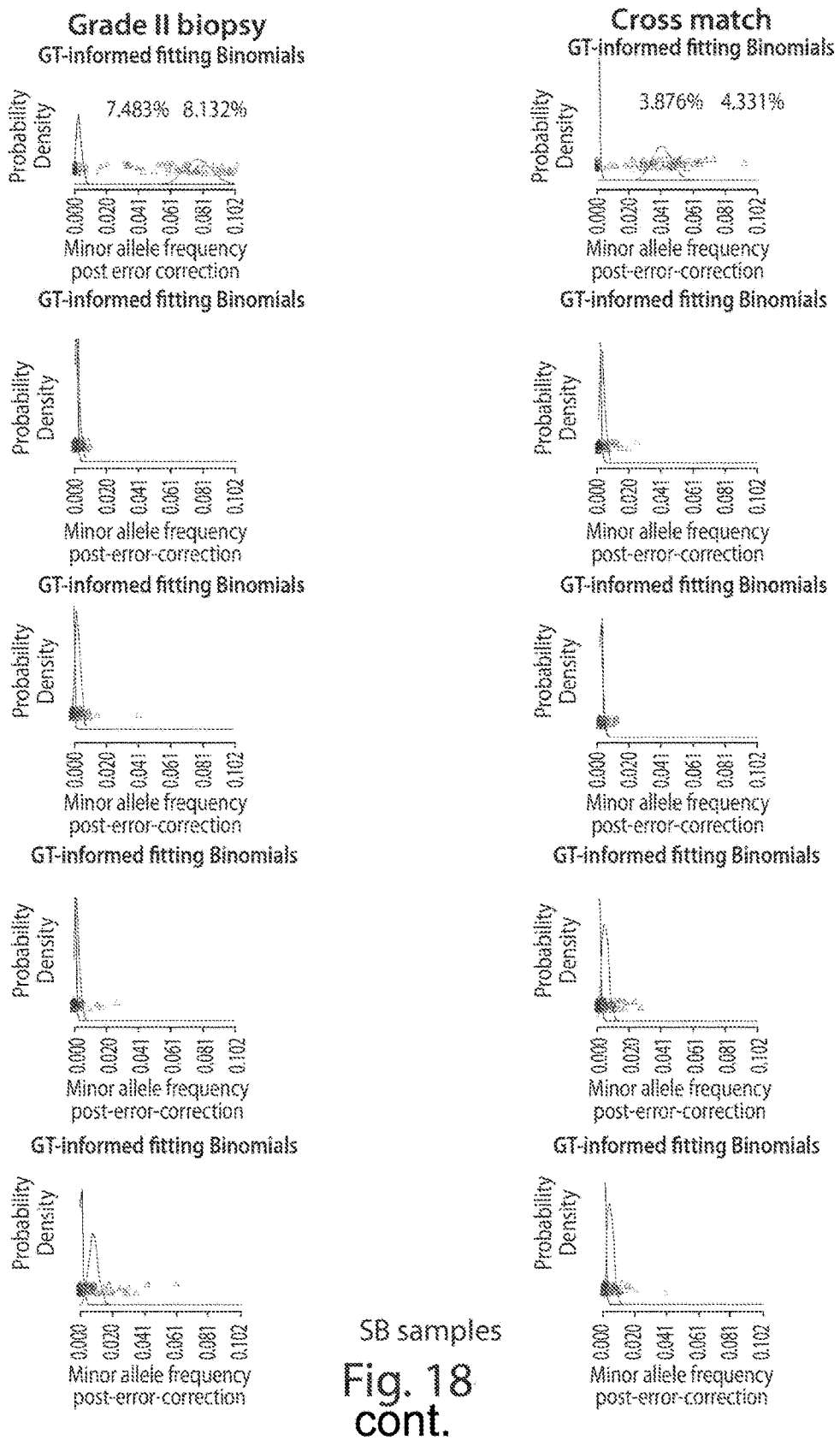
Figure 19:
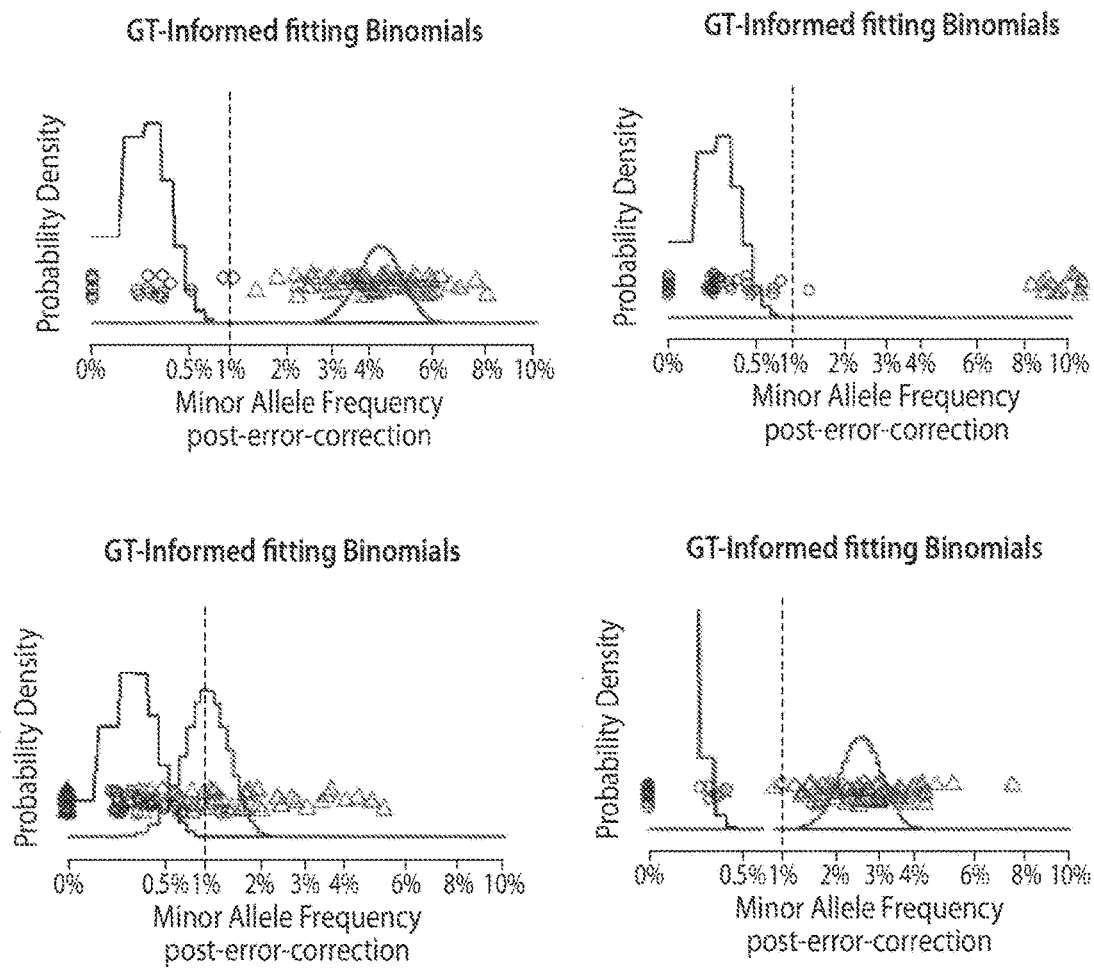
FIG. 19 is a series of graphs of minor allele frequencies post-error correction in post-operative day 1, 4, and 8 samples (POD1, POD4, and POD8).
Figure 19:
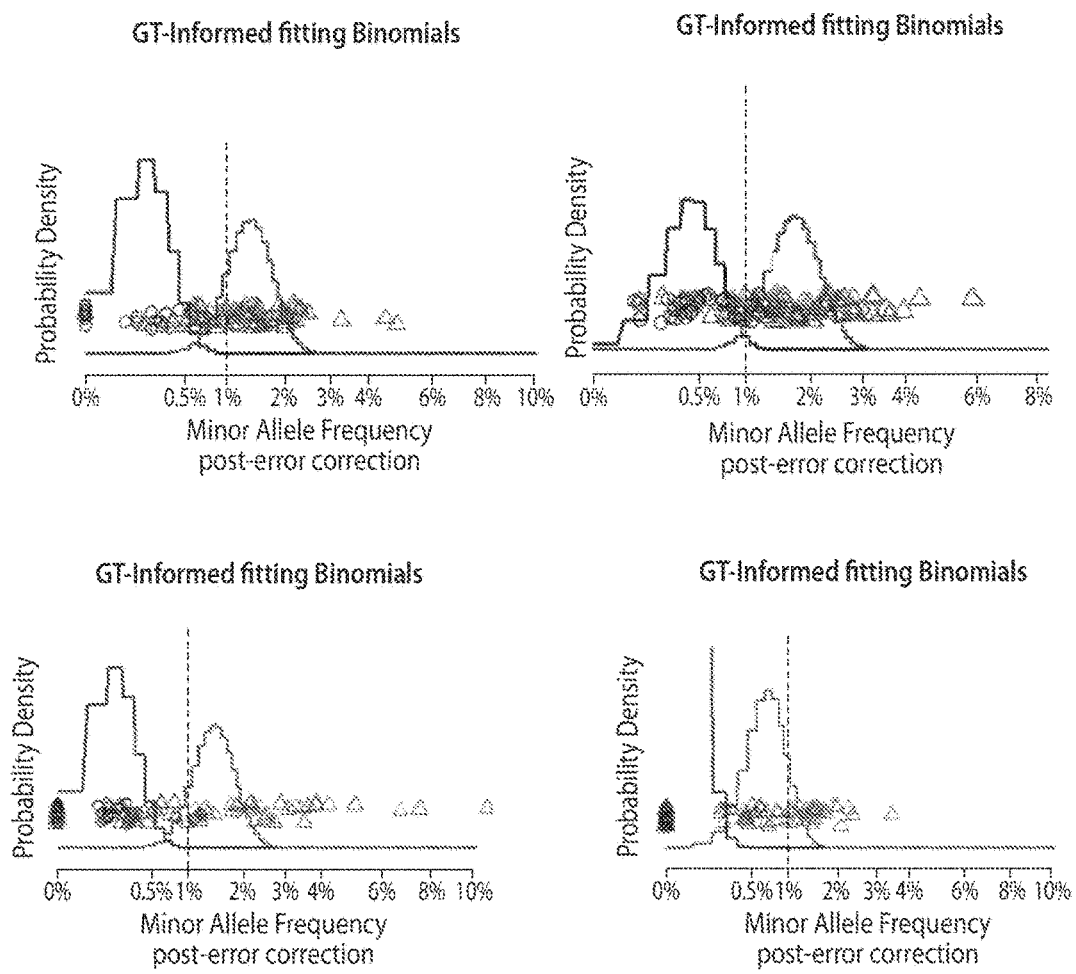
Figure 19:
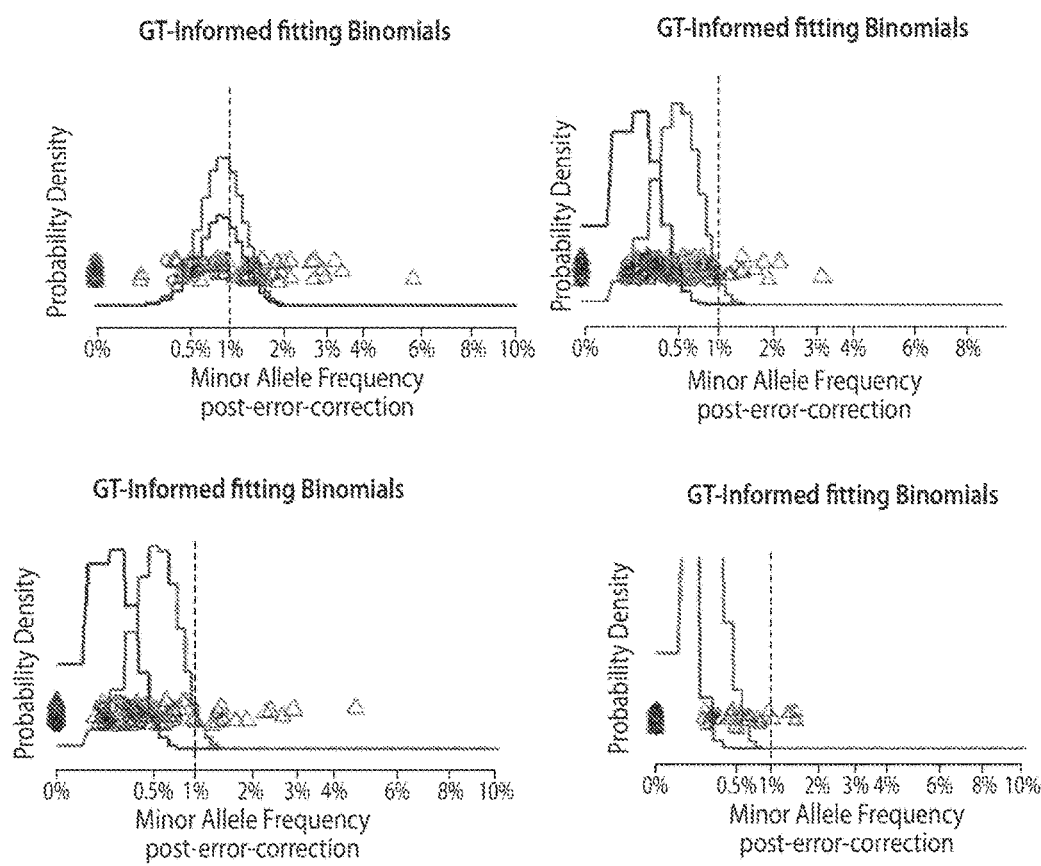

In some embodiments, at least some acts or all of the acts of any of the methods provided, including those in the Examples and Figures, may be implemented as computer-readable instructions stored on one or more non-transitory computer-readable storage media. The computer-readable instructions, when executed by one or more processors, may cause a computing device to execute the acts of the method. FIG. 9 is an exemplary computer system on which some embodiments of the invention may be employed.

An illustrative implementation of a computer system 500 that may be used in connection with any of the embodiments of the invention described herein is shown in FIG. 9. The computer system 500 may include one or more processors 510 and one or more computer-readable non-transitory storage media (e.g., memory 520 and one or more non-volatile storage media 530). The processor 510 may control writing data to and reading data from the memory 520 and the non-volatile storage device 530 in any suitable manner, as the aspects of the present invention described herein are not limited in this respect. To perform any of the functionality described herein, the processor 510 may execute one or more computer-executable instructions stored in one or more computer-readable storage media (e.g., the memory 520), which may serve as non-transitory computer-readable storage media storing instructions for execution by the processor 510.

The above-described embodiments of the present invention can be implemented in any of numerous ways. For example, some aspects of the embodiments may be implemented using hardware, software or a combination thereof. When implemented in software, the software code can be executed on any suitable processor or collection of processors, whether provided in a single computer or distributed among multiple computers. It should be appreciated that any component or collection of components that perform the functions described above can be generically considered as one or more controllers that control the above-discussed functions. The one or more controllers can be implemented in numerous ways, such as with dedicated hardware, or with general-purpose hardware (e.g., one or more processors) that is programmed using microcode or software to perform the functions recited above.

In this respect, it should be appreciated that one implementation of the embodiments of the present invention comprises at least one non-transitory computer-readable storage medium (e.g., a computer memory, a floppy disk, a compact disk, a tape, etc.) encoded with a computer program (i.e., a plurality of instructions), which, when executed on a processor, performs the above-discussed functions of the embodiments of the present invention. The computer-readable storage medium can be transportable such that the program stored thereon can be loaded onto any computer resource to implement the aspects of the present invention discussed herein. In addition, it should be appreciated that the reference to a computer program which, when executed, performs the above-discussed functions, is not limited to an application program running on a host computer. Rather, the term computer program is used herein in a generic sense to reference any type of computer code (e.g., software or microcode) that can be employed to program a processor to implement the above-discussed aspects of the present invention.

Various aspects of the present invention may be used alone, in combination, or in a variety of arrangements not specifically discussed in the embodiments described in the foregoing and are therefore not limited in their application to the details and arrangement of components set forth in the foregoing description or illustrated in the drawings. For example, aspects described in one embodiment may be combined in any manner with aspects described in other embodiments.

Also, embodiments of the invention may be implemented as one or more methods, of which an example has been provided. The acts performed as part of the method(s) may be ordered in any suitable way. Accordingly, embodiments may be constructed in which acts are performed in an order different from illustrated, which may include performing some acts simultaneously, even though shown as sequential acts in illustrative embodiments.

Use of ordinal terms such as "first," "second," "third," etc., in the claims to modify a claim element does not by itself connote any priority, precedence, or order of one claim element over another or the temporal order in which acts of a method are performed. Such terms are used merely as labels to distinguish one claim element having a certain name from another element having a same name (but for use of the ordinal term).

The phraseology and terminology used herein is for the purpose of description and should not be regarded as limiting. The use of "including," "comprising," "having," "containing", "involving", and variations thereof, is meant to encompass the items listed thereafter and additional items.

Having described several embodiments of the invention in detail, various modifications and improvements will readily occur to those skilled in the art. Such modifications and improvements are intended to be within the spirit and scope of the invention. Accordingly, the foregoing description is by way of example only, and is not intended as limiting. The following description provides two examples of the implementation of the described technique.

EXAMPLES

Example 1

Summary

Circulating donor specific cell-free-DNA (cf-DNA) can be isolated from recipient plasma and can be a stable biomarker for cellular injury. A blinded prospective pilot study to test the accuracy of a targeted method of detection and quantification of donor specific cf-DNA in heart transplant recipients was designed.

Twenty-five individual plasma samples were collected from 16 pediatric heart transplant recipients in two clinical settings: at surveillance biopsy (12 patients, 14 samples) and during admission for rejection (4 patients, 11 samples). Samples were blinded and processed. Cf-DNA was extracted. Total cf-DNA was quantified and percent donor specific DNA was measured using targeted next generation sequencing (DANSR, Aria Dx).

All samples collected at the initial diagnosis of rejection showed elevated percentages of donor cf-DNA, P<0.002. Eleven of 13 samples collected during routine surveillance biopsy contained below 1% donor cf-DNA. Of the two samples with elevated donor cf-DNA, one was from a patient who was subsequently admitted in rejection and one from a patient with known positive cross match. The ratio of donor cf-DNA consistently declined with antirejection therapy, P<0.038.

Percentages of donor cf-DNA increase during rejection and fall following treatment. These changes can be monitored, such as by an accurate NGS method. This method is both scalable and efficient.

Introduction

Over 2000 heart transplantations and 300 pediatric heart transplantations are performed in the US each year resulting in approximately 20,000 living transplant recipients currently residing in the US[1]. Currently, one-year survival rates commonly exceed 90% but only 50% survival rate 15 years following transplant[2]. Rejection remains the major cause of graft failure and late mortality and requires lifelong monitoring. Aggressive clinical management of rejection episodes with immunosuppressive therapy has been shown to improve treatment outcomes particularly if rejection is detected early[3]. The current gold standard for monitoring rejection is catheter based endomyocardial biopsy. The invasive procedure is associated with risks and discomfort for the patient, which is particularly pronounced in the pediatric population[4,5]. Several non-invasive screening methods such as transthoracic echocardiography and diagnostic markers such as C-reactive protein (CRP), brain natriuretic peptides (BNP) and troponin levels exist, yet these approaches are all weakly associated with different grades of rejection and have poor correlation with biopsy defined rejection[6]. A more costly test based on quantification of gene expression in mononuclear cells of peripheral blood has been FDA approved and is commercially available[7,8]. Use of this test in selected centers and patient populations has resulted in fewer biopsies[9]. However, the sensitivity and specificity of this test for accurate detection is less than 80%. Therefore, there is a need for a sensitive, specific and cost effective, non-invasive test for surveillance of transplant rejection.

Cell-free-DNA (cf-DNA) is as a marker for cellular injury caused by rejection for several organs, including the heart[10-13]. In adult cardiac transplant patients biopsy proven rejection episodes correlate with increased levels of donor specific cf-DNA in recipient plasma detected by whole genome next generation sequencing (NGS)[10]. However, this approach may be limited as a surveillance tool by cost, throughput, and complexity of analysis. Recent advances in NGS technologies and sample preparation make a donor-specific cf-DNA assay more feasible. Novel, targeted approaches for the non-invasive detection of fetal chromosomal abnormalities can potentiate the utility of cf-DNA as a biomarker for sensitive, timely, and cost effective surveillance of early rejection in heart transplant patients. In this study, a targeted NGS method initially developed for non-invasive fetal genetic screening was applied to quantify the percent donor specific cf-DNA in pediatric heart transplant patients[14,15].

Methods

Sample and Data Collection

Blood samples were collected from pediatric cardiac transplant recipients under a protocol approved by the Institutional Review Board at Children's Hospital of Wisconsin. Samples were drawn at the time of standard lab draw—immediately prior to routine surveillance biopsy (SB), on the day of clinical rejection (Rj) diagnosis, and at days 4 and 8 following the initial Rj diagnosis. Samples were immediately blinded, coded, and delivered to the lab. Clinical data on patient status and medication profile were recorded at the time of each sample collection by an independent clinical team. All collected clinical data were entered into and stored in a RedCap database (Vanderbilt University, Nashville, Tenn.). Processing and analysis of samples was carried out by researchers blinded to the clinical status with no access to the clinical database. Each blood sample was collected in either 10 ml K$_3$EDTA vacutainer (BD, Franklin Lakes, N.J.) or 10 ml BCT tubes (Streck, Omaha, Nebr.).

The medical history of rejection patients and medical summary of all included patients are provided in Tables 1 and 2.

Inclusion/Exclusion Criteria

All single organ cardiac transplant recipients under 18 years of age whose progress can be followed were candidates for inclusion in the study. Multiple organ transplant recipients were excluded. Samples taken from patients at time of surveillance biopsy who were within three months of treatment for a rejection episode were excluded from the analysis.

Plasma Processing and DNA Extraction

Processing of blood to plasma by centrifugation was carried out as previously described[16] and plasma was stored at −80° C. until DNA extraction. All cf-DNA extraction was performed with the Circulating Nucleic Acid Extraction Kit (Qiagen, Valencia, Calif.). One to three ml of plasma from each sample was extracted using 5.6 μg of carrier RNA per sample and eluted in 30 μl of 1 mM Tris and 0.1 mM EDTA. Genomic DNA from each recipient was prepared from the buffy coat using the Gentra Puregene Blood Kit (Qiagen, Valencia, Calif.). Purified genomic DNA was re-suspended in 1.0 mM Tris HCl pH 8.0 and 0.1 mM EDTA. DNA quality was tested by OD 260/280 ratios, quantified by UV spectrophotometry using a Nanodrop 2000 (Thermo Scientific, Wilmington, Del.). Genomic donor DNA for genotyping was obtained from Blood Center of Wisconsin, which collects and stores DNA from all donors as part of donor/recipient matching process.

Total Cf-DNA Analysis

Total cf-DNA content in each sample was evaluated in triplicate by TaqMan real-time PCR using an assay targeting RNaseP (Applied Biosystems, Foster City, Calif.). For each PCR reaction, 2 μl of DNA extraction eluate was used. A dilution series of a human genomic DNA samples was used to create a standard curve for quantification. The DNA standards originated from a TK6 cell-line (ATCC, Manassas, Va.). PCR analysis was carried out on an ABI7900 machine according to the manufacturer's instructions.

Percent Donor Cf-DNA Analysis

Recipient and donor cf-DNA in plasma was quantified using the Digital Analysis of Selected Regions (DANSR™) assay as previously described[14,17]. This approach enables simultaneous quantification of hundreds of loci by cf-DNA dependent catenation of two locus-specific oligonucleotides via an intervening 'bridge' oligo to form a PCR template. For each sample, one hundred ninety-two regions on chromosomes 1-12 were targeted. Cf-DNA generated PCR products were quantified on an Illumina Hiseq 2000™ instrument (Illumina, San Diego, Calif.). Genotyping of donor and recipient genomic DNA was carried out by the same assay. Recipient and donor genomic DNA was sheared to 300 bp by sonication (Covaris, Woburn, Mass.). Final fragment size was verified on a Bioanalyzer (Agilent Technologies, Santa Clara, Calif.). 150 ng of sheared recipient and genomic donor DNA was used for genotyping. An input of 5-15 ng of total cf-DNA as determined by real-time PCR was used for each plasma sample analyzed.

Data Analysis

Genotypes were determined for 192 loci from DNA samples extracted from recipient WBCs, recipient plasma, and donor WBCs. Loci (markers) were deemed "informative" for calculating donor specific DNA frequencies when recipient genotypes were homozygous and donor genotypes were either heterozygous or homozygous for the other allele. Loci with fewer than 100 total read counts were excluded. To calculate donor specific DNA frequencies present in plasma samples in the subset of informative markers, minor-allele read counts were modeled as a binomial distribution as previously described[17,18]. The percent donor specific reads was defined at the peak of the distribution. The maximum likelihood estimator and standard error of the binomial frequency parameter were computed with the software R package stats[4]. Prior to modeling minor allele frequency, an estimated read error was subtracted from the data. Error rates were calculated for each sample by identifying marker loci where donor and recipient were homozygous for the same allele and therefore should not have had any minor allele read counts. The read error was modeled by the same maximum likelihood method described above. The read error was subtracted from both A and B reads of informative markers.

A summary of the data analysis is provided in FIG. 1.

Results

Sample Collection

Fourteen samples from twelve patients were collected just prior to routine endomyocardial surveillance biopsy (SB). Four samples from four patients were drawn at the time of biopsy proven rejection episodes (Rj d1). In addition, for each rejection patient follow up plasma samples were collected during rejection therapy at day 4 and 8 after diagnosis (Rj d4, Rj d8). Samples from one patient were collected as both SB and Rj.

Sequencing Data

Determination of genotypes was calculated as described. Each donor recipient combination resulted in 39-82 informative assays from the 192 targets. The number of reads used for genotyping was 100-1200. Sequencing plasma samples produced on average 82,663±SEM 11,119 high quality reads per sample that were used for determination of percent donor specific cf-DNA in plasma. Each plasma sample contained on average 0.2% read errors that were extracted prior to calculating the percent donor specific cf-DNA.

Percent Donor Cf-DNA

Figure 2:
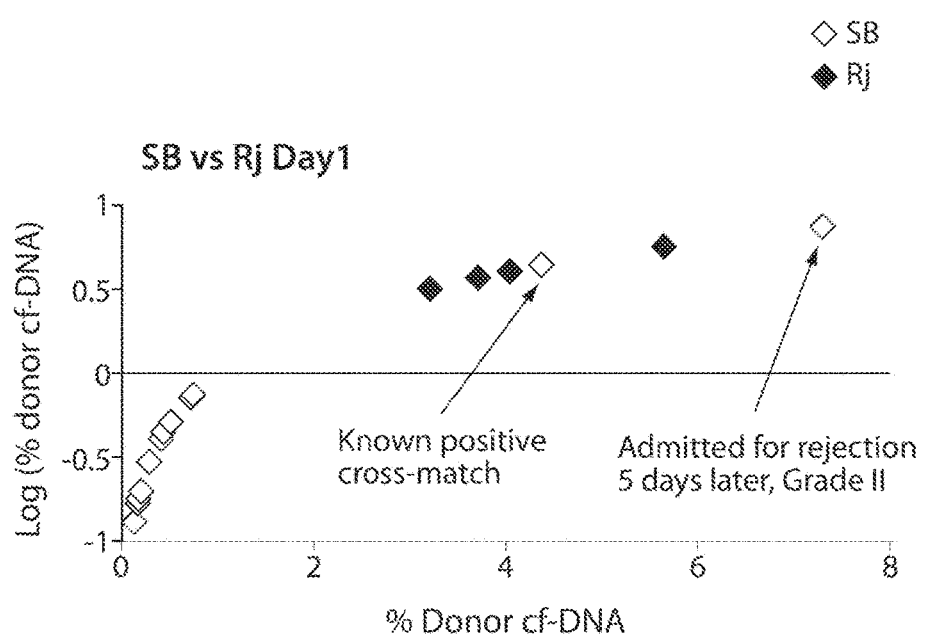
FIG. 2 is a graph showing log percent donor specific (DS) cell-free (cf) DNA versus percent donor cf-DNA in patient samples taken during surveillance biopsy (SB) and rejection (Rj).
Figure 3:
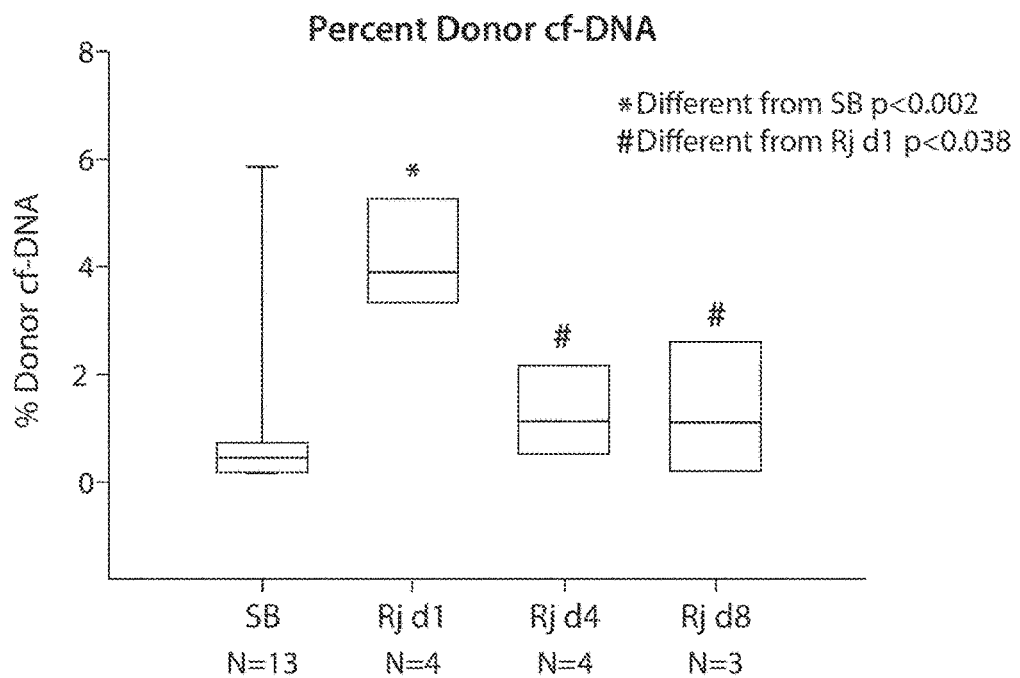
FIG. 3 is a bar graph showing percent donor cf-DNA in surveillance biopsy (SB) patient samples and rejection (Rj) patient samples taken the day of clinical diagnosis of rejection (Rj d1) and at day 4 (Rj d4) and day 8 (Rj d8) after clinical diagnosis of rejection.
Figure 4:
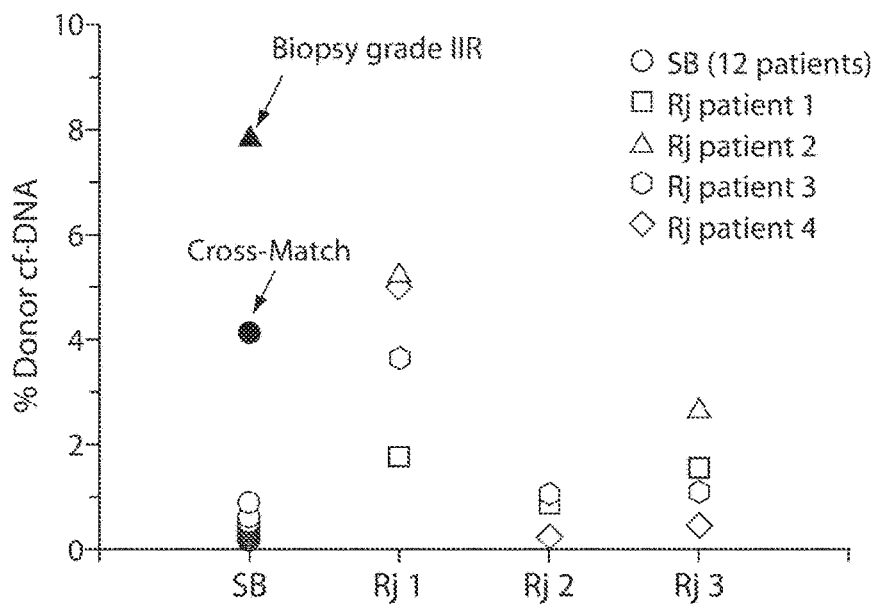
FIG. 4 is a graph showing percent donor cf-DNA in surveillance biopsy (SB) samples and rejection (Rj) samples taken the day of clinical diagnosis of rejection (Rj d1) and at day 2 (Rj d2) and day 3 (Rj d3) after clinical diagnosis of rejection.

All samples collected at the initial diagnosis of rejection showed elevated levels of percent donor specific (DS) cell-free(cf)-DNA. Twelve of the 14 SB samples analyzed contained less than 1% donor cf-DNA (below 0 on the log scale in FIG. 2). Of the two SB samples with elevated donor cf-DNA, one was from a patient subsequently diagnosed with rejection and the other had a known positive antibody cross-match implicating higher risk for rejection. The lower levels of donor DNA in SB samples were significantly different from Rj samples (FIG. 3). In addition, levels of donor cf-DNA had decreased significantly (FIG. 3) at day 4 and 8 of rejection indicating that these patients responded to immunosuppressive medications resulting in less cellular damage of the transplanted cardiac tissue. Based on the data, it was concluded that donor-specific DNA is initially high at rejection compared to samples with no clinical suspicion of rejection, but levels decrease rapidly upon treatment with immunosuppressive medication.

Total Cf-DNA

Total cf-DNA in most samples were ranging from $10^2$-$10^3$ similar to what is found in healthy non-transplanted subjects[19,20]. Two samples exhibited abnormally large amounts of total cf-DNA. These samples were collected from the same patient during a rejection episode during which the patient presented in cardiac arrest soon after initial diagnosis of rejection.

Discussion

In this study, a novel sensitive and cost-effective methodology was applied to determine levels of donor specific cf-DNA in pediatric heart transplant patients at the time of routine surveillance biopsy and during events of rejection. The current gold standard for assessing rejection is endomyocardial biopsy, however even with this invasive procedure some controversy still exists regarding grading and interpretation. For example, there is variability in pathological interpretation of histologic grades, especially with severe cases of rejection due to the difficulty with estimating the amounts of nodular infiltrate present[21]. Other means of assessing rejection status exists (Table 3) but currently none can function as a replacement for biopsy. Cell-free DNA has been found to be a less invasive, reliable, measurable, sensitive and specific biomarker. DNA is stable and collection tubes that preserve cell integrity and techniques specifically optimized for cf-DNA with respect to plasma processing, storage and DNA extraction under a variety of shipping conditions are available.

A targeted next generation sequencing approach was employed to detect cf-DNA in pediatric heart transplant patients. Donor specific cell-free DNA was detected and quantified from 1.5 ml of recipient plasma. The percentage of donor specific cell-free DNA was elevated in 100% of patients diagnosed with rejection. The percentage of donor specific cell-free DNA decreased to near baseline in all patients upon initiation of anti-rejection therapy. Targeted quantification of circulating donor specific cell-free DNA using next generation sequencing appears to be sensitive and feasible for rejection surveillance.

Based on this study, a sensitivity of 100% and a specificity of 95% was found, which is high when compared to other currently existing biomarkers. The patient in whom this occurred exhibited a positive antibody cross-match. Thus, there was an immune response also in this patient, and, therefore, the specificity of cf-DNA could be improved.

In one of the samples that was collected when the patient was visiting for routine surveillance biopsy showing no signs of being in clinical rejection, cf-DNA correctly predicted that the patient was actually in rejection. Once confirmed, treatment was initiated. The levels of donor-specific cf-DNA rapidly decreased upon treatment. The ratio of donor to recipient cf-DNA was one of the highest in this predictive sample, and it was collected 6 days prior to the patients being hospitalized and treated.

In many cases, a rejection episode appears sudden due to, for example, altered metabolism or non-compliance with anti-rejection medication. It has been found that cf-DNA could function as a non-invasive rapid initial screen with or without a clinical suspicion for rejection. Sequencing techniques are rapidly developing and methods to acquire sequencing data for determining donor percent cf-DNA similar to methods used in this study can be obtained within 24 hours. For patients in chronic rejection one would expect a slower increase of cf-DNA. One could envisage that chronic rejection would slowly increase the ratio of donor to recipient cf-DNA enabling the monitoring of rejection in real-time and possibly adjusting therapy accordingly. For all acute rejection cases in this study, the patient displayed high plasma levels of donor specific cf-DNA on day 1 after rejection. Upon treatment with anti-rejection medication at collection time points 2 and 3 (aimed at day 4 and 8 after diagnosis) the levels decreased. This may indicate that, in addition to functioning as a predictor for rejection, cf-DNA could give the physician information about how well anti-rejection therapy is working and allow for the adjustment of the levels of a therapeutic based on cf-DNA levels. The turnover of cf-DNA is rapid. It is expected that donor specific cf-DNA in transplant rejection patients will decrease shortly after effective therapeutic levels of antirejection medications have been reached.

TABLE 1

Medical history of rejection patients

| # | Patient | age | Type | POD at sample collection (days) | Medications at sample collection | Troponin | Bx | Wedge | EF |
|---|---|---|---|---|---|---|---|---|---|
| sample 1 | 1 | | SB | 346 | Mycophenolate (oral) Tacrolimus (oral) Steroids (oral) | <0.012 | 0 | 14 | 68 |
| sample 2 | 2 | | SB | 2121 | Mycophenolate (oral) Tacrolimus (oral) Steroids (oral) | <0.012 | 0 | 12 | 62 |
| sample 3 | 2 | | SB | 2382 | Mycophenolate (oral) Tacrolimus (oral) Steroids (oral) | <0.012 | 0 | 13 | 57 |
| sample 4 | 3 | | SB | 2208 | Mycophenolate (oral) Tacrolimus (oral) | <0.012 | 0 | 16 | 65 |
| sample 5 | 4 | | SB | 210 | Mycophenolate (oral) Tacrolimus (oral) | <0.012 | 0 | 7 | 63 |
| sample 6 | 4 | | SB | 385 | Mycophenolate (oral) Tacrolimus (oral) Steroids (oral) | — | — | 8 | 56 |
| sample 7 | 5 | | SB | 391 | Mycophenolate (oral) Tacrolimus (oral) Steroids (oral) | <0.012 | 0 | 18 | 63 |
| sample 8 | 6 | | SB | 4152 | Mycophenolate (oral) Tacrolimus (oral) Steroids (oral) | 0.02 | — | 6 | 65 |
| sample 9 | 7 | | SB | 350 | Mycophenolate (oral) Tacrolimus (oral) | <0.012 | 0 | 7 | 60 |
| sample 10 | 8 | | SB | 1846 | Mycophenolate (oral) Tacrolimus (oral) | <0.012 | 1R | 9 | 52 |
| sample 11 | 9 | | SB | 368 | Mycophenolate (oral) Tacrolimus (oral) | <0.012 | 0 | 10 | 74 |
| sample 12 | 10 | | SB | 1471 | Mycophenolate (oral) Tacrolimus (oral) | <0.012 | — | 14 | 68 |
| sample 13 | 11 | | SB | 694 | | <0.012 | 0 | 9 | nl |
| sample 14 | 12 | | SB | 1569 | Mycophenolate (oral) Tacrolimus (oral) | 0.02 | 2R | 8 | — |
| sample 15 | 12 | | Rj 1 | 1574 | Mycophenolate (oral) Tacrolimus (oral) Steroids (IV) Immunoglobulins (IV) | <0.012 | 1R | — | 60 |

TABLE 1-continued

Medical history of rejection patients

| | | | | | | | | |
|---|---|---|---|---|---|---|---|---|
| sample 16 | 12 | Rj 2 | 1577 | Mycophenolate (oral) Sirolimus (oral) Tacrolimus (oral) Steroids (IV) Immunoglobulins (IV) Rituximab (IV) | — | — | — | — |
| sample 17 | 12 | Rj 3 | 1580 | Sirolimus (oral) Tacrolimus (oral) Steroids (Oral) Immunoglobulins (IV) | — | — | — | 59 |
| sample 18 | 13 | Rj 1 | 1665 | Mycophenolate (IV) Tacrolimus (oral) Steroids (IV) | 0.59 | — | — | 42 |
| sample 19 | 13 | Rj 2 | 1669 | Mycophenolate (IV) Tacrolimus (oral) Steroids (IV) Thymoglobulin (IV) Immunoglobulins (IV) | — | 1R | 15 | 52 |
| sample 20 | 13 | Rj 3 | 1673 | Mycophenolate (IV) Tacrolimus (oral) Steroids (oral) Thymoglobulin (IV) Immunoglobulins (IV) Rituximab (IV) | — | — | — | 59 |
| sample 21 | 14 | Rj 1 | 175 | Mycophenolate (IV) Steroids (IV) | — | — | — | odd |
| sample 22 | 14 | Rj 2 | 180 | Mycophenolate (IV) Steroids (IV) Thymoglobulin (IV) | — | 2R | 12 | 39 |
| sample 23 | 14 | Rj 3 | 187 | Mycophenolate (IV) Tacrolimus (oral) Steroids (IV) Thymoglobulin (IV) | — | — | — | 69 |
| sample 24 | 15 | Rj 1 | 688 | Mycophenolate (oral) Tacrolimus (oral) Steroids (IV) Immunoglobulins (IV) | <0.012 | 2R | 17 | 64 |
| sample 25 | 15 | Rj 2 | 692 | Mycophenolate (oral) Tacrolimus (oral) Steroids (IV) Immunoglobulins (IV) Rituximab (IV) | <0.012 | — | — | 64 |
| sample 26 | 15 | Rj 3 | 695 | Mycophenolate (oral) Tacrolimus (oral) Steroids (IV) | | | | |

| # | CI | CGV | % donor cf-DNA | Total cf-DNA GE/ml | Total reads | read error |
|---|---|---|---|---|---|---|
| sample 1 | 3.4 | 0 | 4.10 ± 0.11 | 549 ± 67 | 94146 | |
| sample 2 | 2.4 | 0 | 0.48 ± 0.04 | 567 ± 49 | 74561 | |
| sample 3 | 2.6 | 0 | 0.44 ± 0.04 | 257 ± 23 | 76765 | |
| sample 4 | 3 | 0 | 0.88 ± 0.06 | 214 ± 34 | 70614 | |
| sample 5 | 3 | 0 | 0.12 ± 0.02 | 3795 ± 195 | 86746 | |
| sample 6 | 3.18 | 0 | 0.042 ± 0.04 | 104 ± 31 | 87678 | |
| sample 7 | 4.5 | 0 | 0.32 ± 0.03 | 519 ± 102 | 82664 | |
| sample 8 | 4.3 | 0 | 0.25 ± 0.03 | 788 ± 53 | 69191 | |
| sample 9 | 3.2 | 0 | 0.17 ± 0.02 | 2981 ± 41 | 65563 | |
| sample 10 | 2.45 | 0 | 0.18 ± 0.02 | 1339 ± 310 | 59382 | |
| sample 11 | 3 | 0 | 0.62 ± 0.04 | 370 ± 7 | 88841 | |
| sample 12 | 3.1 | 0 | 0.39 ± 0.05 | 560 ± 75 | 82135 | |
| sample 13 | 3.6 | 0 | 0.22 ± 0.02 | 370 ± 48 | 90515 | |
| sample 14 | 2.14 | 0 | 7.81 ± 0.17 | 215 ± 50 | 81525 | |
| sample 15 | — | — | 5.20 ± 0.13 | 974 ± 135 | 91005 | |
| sample 16 | — | — | 1.07 ± 0.06 | 553 ± 91 | 81735 | |
| sample 17 | — | — | 2.63 ± 0.10 | 1105 ± 247 | 84166 | |
| sample 18 | — | — | 3.64 ± 0.11 | 789 ± 52 | 86740 | |
| sample 19 | 1.7 | 0 | 1.04 ± 0.06 | 1632 ± 177 | 89905 | |
| sample 20 | — | — | 1.08 ± 0.06 | 2264 ± 389 | 94649 | |
| sample 21 | — | — | 4.97 ± 0.12 | 4177 ± 914 | 93927 | |
| sample 22 | 2 | 0 | 0.21 ± 0.02 | 126560 ± 12698 | 100417 | |
| sample 23 | — | — | 0.45 ± 0.03 | 26606 ± 2886 | 100435 | |
| sample 24 | 1.6 | 0 | 1.76 ± 0.10 | 488 ± 35 | 61908 | |
| sample 25 | — | — | 0.88 ± 0.06 | 1474 ± 74 | 74157 | |
| sample 26 | | | 1.57 ± 0.08 | | 79876 | |

TABLE 2

Medical summary of all included patients

| Patints characteristics | Results |
|---|---|
| age at surgery (years) | |
| <1 | x |
| 1-9 | y |
| >10 | o |
| age at rejection | |
| <1 | x |
| 1-9 | x |
| >10 | x |
| Gender | |
| Male | x |
| Female | x |
| AB compatability | |
| yes | |
| no | |
| Positive cross match | |

TABLE 3

Summary of Methods for monitoring rejection

| Test | Sensitivity/Specificity | Invasive | Cost for test |
|---|---|---|---|
| Biopsy[3] | 90%/80% | Yes | $4,000 |
| Echocardiography[7] | 76%/88% | No | $500 |
| Troponin[10] | 80%/62% | No | $76 |
| BNP[9] | 90%/76% | No | $342 |
| CRP[9] | 64%/66% | No | $95 |
| Gene expression profiling[14] | 75%/78% | No | $3,000 |
| Cell free DNA (WGS)[19] | 83%/84% | No | ~$3,000 |
| Cell free DNA (TS)[Prelim Data] | 100%/95-100% | No | <$200 |

TS (Targeted Sequencing),
WGS (Whole Genome Sequencing)

References for Example 1

1. OPTN/SRTR Annual Report www.ustransplantorg/annual_reports/current/.
2. Hertz M I, Aurora P, Benden C, et al. Scientific Registry of the International Society for Heart and Lung Transplantation: introduction to the 2011 annual reports. J Heart Lung Transplant 2011; 30:1071-7.
3. Kaczmarek I, Deutsch M A, Sadoni S, et al. Successful management of antibody-mediated cardiac allograft rejection with combined immunoadsorption and anti-CD20 monoclonal antibody treatment: case report and literature review. J Heart Lung Transplant 2007; 26:511-5.
4. Daly K P, Marshall A C, Vincent J A, et al. Endomyocardial biopsy and selective coronary angiography are low-risk procedures in pediatric heart transplant recipients: Results of a multicenter experience. J Heart Lung Transplant 2012; 31:398-409.
5. Pophal S G, Sigfusson G, Booth K L, et al. Complications of endomyocardial biopsy in children. J Am Coll Cardiol 1999; 34:2105-10.
6. Moran A M, Lipshultz S E, Rifai N, et al. Non-invasive assessment of rejection in pediatric transplant patients: serologic and echocardiographic prediction of biopsy-proven myocardial rejection. J Heart Lung Transplant 2000; 19:756-64.
7. Deng M C, Eisen H J, Mehra M R, et al. Noninvasive discrimination of rejection in cardiac allograft recipients using gene expression profiling. Am J Transplant 2006; 6:150-60.
8. Horwitz P A, Tsai E J, Putt M E, et al. Detection of cardiac allograft rejection and response to immunosuppressive therapy with peripheral blood gene expression. Circulation 2004; 110:3815-21.
9. Pham M X, Teuteberg J J, Kfoury A G, et al. Gene-expression profiling for rejection surveillance after cardiac transplantation. The New England journal of medicine 2010; 362:1890-900.
10. Snyder T M, Khush K K, Valantine H A, Quake S R. Universal noninvasive detection of solid organ transplant rejection. Proceedings of the National Academy of Sciences of the United States of America 2011; 108:6229-34.
11. Garcia Moreira V, Prieto Garcia B, Baltar Martin J M, Ortega Suarez F, Alvarez F V. Cell-free DNA as a non-invasive acute rejection marker in renal transplantation. Clin Chem 2009; 55:1958-66.
12. Gadi V K, Nelson J L, Boespflug N D, Guthrie K A, Kuhr C S. Soluble donor DNA concentrations in recipient serum correlate with pancreas-kidney rejection. Clin Chem 2006; 52:379-82.
13. Lo Y M, Tein M S, Pang C C, Yeung C K, Tong K L, Hjelm N M. Presence of donor-specific DNA in plasma of kidney and liver-transplant recipients. Lancet 1998; 351:1329-30.
14. Sparks A B, Wang E T, Struble C A, et al. Selective analysis of cell-free DNA in maternal blood for evaluation of fetal trisomy. Prenat Diagn 2012:1-7.
15. Ghanta S, Mitchell M E, Ames M, et al. Non-invasive prenatal detection of trisomy 21 using tandem single nucleotide polymorphisms. PLoS One 2010; 5.
16. Hidestrand M, Stokowski R, Song K, et al. The influence of temperature during transportation on cell free DNA analysis Fetal Diagnosis and Therapy 2011.
17. Sparks A B, Struble C A, Wang E T, Song K, Oliphant A. Noninvasive prenatal detection and selective analysis of cell-free DNA obtained from maternal blood: evaluation for trisomy 21 and trisomy 18. American journal of obstetrics and gynecology 2012; 206:319 e1-9.
18. Chu T, Bunce K, Hogge W A, Peters D G. A novel approach toward the challenge of accurately quantifying fetal DNA in maternal plasma. Prenat Diagn 2010; 30:1226-9.
19. Suzuki N, Kamataki A, Yamaki J, Homma Y. Characterization of circulating DNA in healthy human plasma. Clinica chimica acta; international journal of clinical chemistry 2008; 387:55-8.
20. Fleischhacker M, Schmidt B. Circulating nucleic acids (CNAs) and cancer—a survey. Biochimica et biophysica acta 2007; 1775:181-232.
21. Marboe C C, Billingham M, Eisen H, et al. Nodular endocardial infiltrates (Quilty lesions) cause significant variability in diagnosis of ISHLT Grade 2 and 3A rejection in cardiac allograft recipients. J Heart Lung Transplant 2005; 24:S219-26.
22. Lo Y M, Zhang J, Leung T N, Lau T K, Chang A M, Hjelm N M. Rapid clearance of fetal DNA from maternal plasma. American journal of human genetics 1999; 64:218-24.
23. Beiter T, Fragasso A, Hudemann J, Niess A M, Simon P. Short-term treadmill running as a model for studying cell-free DNA kinetics in vivo. Clin Chem 2011; 57:633-6.

Example 2

Introduction

Over 2,000 heart transplantations including nearly 400 pediatric cases are performed annually resulting in approximately 20,000 living transplant recipients currently residing in the US (2009 OPTN/SRTR Annual Report 1999-2008).

Currently, one year survival rates following heart transplantation commonly exceed 90% but 10 year survival is less than 60%[1]. Rejection remains a major cause of graft failure and late mortality and generally requires lifelong surveillance monitoring. Aggressive clinical management of rejection episodes with immunosuppressive therapy has been shown to improve treatment outcomes particularly if rejection is detected early[2]. The current gold standard for monitoring rejection is catheter based endomyocardial biopsy (EMB). This invasive procedure is associated with risks and discomfort for the patient which are particularly pronounced in the pediatric population[3, 4]. Several non-invasive screening methods such as transthoracic echocardiography and diagnostic markers such as C-reactive protein (CRP), brain natriuretic peptide (BNP) and troponin levels have been proposed, yet these approaches are all only weakly associated with different grades of rejection and have poor correlation with biopsy defined rejection[5-7]. Quantification of gene expression in mononuclear cells of peripheral blood has been FDA approved for use in adult transplant survivors and is commercially available[8-10]. However, although a high negative predictive value has been reported[8], the sensitivity and specificity of this test for accurate detection of moderate to severe grades of rejection (≥2R, ISHLT 2005 revised standards[11]) is less than 80%[10, 12]. Furthermore, this test has not been approved for patients less than 15 years of age nor during the early post-transplant period (i.e., <2 months post-transplant). There remains a compelling need for a sensitive and specific test suited for serial use for surveillance of transplant rejection.

Donor specific cell-free DNA (DS cf-DNA) is as a stable marker for cellular injury caused by rejection in several organs, including the heart[13-16]. In adult cardiac transplant patients, biopsy proven rejection episodes correlate with increased levels of DS cf-DNA in recipient plasma detected by whole genome next generation sequencing (NGS)[13]. The complexity and cost of the analysis required by this approach may limit its application as a surveillance tool. However, recent advances in NGS technologies and sample preparation make a DS cf-DNA assay more feasible. Specifically, targeted NGS approaches applied to non-invasively detect chromosomal abnormalities in fetal DNA may potentiate the development of DS cf-DNA as a biomarker for rejection in solid organ transplant recipients[17, 18]. In this study, such a targeted NGS method initially developed for non-invasive fetal genetic screening was applied to quantify the percent DS cf-DNA in pediatric heart transplant patients.

Methods

Patient Sample

All cardiac transplant recipients followed at the Herma Heart Center at Children's Hospital of Wisconsin were invited to participate in this study. Exclusion criteria included: multi-organ transplant recipients, samples which failed genotyping quality control (QC), those with incompletely documented collection times or samples obtained from patients on ECMO. Participants provided informed consent. The protocol was approved by the Institutional Review Board at Children's Hospital of Wisconsin.

Blood Sample Collection

To assess circulating levels of cf-DNA, 5-10 cc of anticoagulated blood were collected from pediatric cardiac transplant recipients at Children's Hospital of Wisconsin (CHW). Each blood sample was collected in either 10 ml K3EDTA vacutainer (BD, Franklin Lakes, N.J.) or 10 nil BCT tubes (Streck, Omaha, Nebr.).

Sample collection coincided with collection of standard laboratory draws at five different clinical scenarios. Scenario 1) post-transplant—33 samples were drawn at three time points in each of eleven new heart transplant recipient patients at 14-36 hours, 84-126 hours, and 160-206 hours following removal of aortic cross clamp and reperfusion of the donor organ. Scenario 2) pre- and postendomyocardial biopsy—12 samples were drawn at two time points in 6 heart transplant recipients undergoing surveillance biopsy, immediately prior to and within 35 minutes following EMB. Scenario 3) scheduled surveillance biopsy—38 samples were collected from 26 asymptomatic heart transplant recipients in the catheterization laboratory immediately prior to scheduled surveillance biopsy. Scenario 4) unscheduled diagnostic biopsy—7 samples were collected from 6 hospitalized heart transplant recipients prior to unscheduled diagnostic EMB to evaluate suspicious clinical findings suggestive of rejection. Scenario 5) rejection—12 samples were collected from 4 heart transplant recipients with biopsy proven rejection (≥grade 2R cellular and/or positive for antibody mediated rejection (AMR 1) as defined by the ISHLT 2005 revised standards11) at three time points: before treatment (3-44 hours prior to the initiation of intravenous (IV) steroids), during treatment (45-87 hours following the initial IV steroid dose), and following treatment (110-162 hours after the initial intravenous dose but 43-98 hours following discontinuation of IV steroids).

Following collection, blood samples were immediately coded, de-identified, and delivered to the laboratory. Plasma preparation, extraction and plating of cf-DNA and determination of total circulating cf-DNA (Tcf-DNA) as outlined below was carried out by researchers blinded to identifiers and with no access to the clinical database.

Clinical Data Collection

Clinical, laboratory, cardiac catherization and echocardiographic data were recorded at the time of each sample collection and data were managed using Research Electronic Data Capture (REDCap) electronic capture tools hosted at CHW19.

Clinical Monitoring of Rejection

Patients who had clinical symptoms suggestive of rejection underwent the Center's standard clinical, laboratory and echocardiographic evaluation. Laboratory tests including immunosuppressant drug levels, troponin I, and BNP were drawn. Echocardiography was also performed. Signs that were highly suspicious for rejection included elevated BNP or troponin levels, with or without low levels of immunosuppressive therapy. On echocardiography, increased valvular regurgitation, the presence of a pericardial effusion, or evidence of poor systolic or diastolic function were considered highly suspicious for rejection. In the setting of hemodynamic instability, empiric rejection therapy may have been initiated prior to obtaining EMB; otherwise, a biopsy was performed prior to initiating rejection specific treatment and biopsy grading was based on ISHLT 2005 revised standards[11].

Plasma Processing and DNA Extraction

Separation of plasma from blood cellular elements by centrifugation was carried out as previously described[20]. Plasma was stored at −80° C. until DNA extraction. All cf-DNA extractions were performed with the Circulating Nucleic Acid Extraction Kit (Qiagen, Valencia, Calif.). One to three ml of plasma from each sample was extracted using 11.2 µg of carrier RNA per sample and eluted in 30 µl of TE buffer (1 mM Tris-HCl, pH 7.0 and 0.1 mM EDTA). Genomic DNA from each recipient was prepared from the buffy coat that includes the white blood cells using the Gentra Puregene Blood Kit (Qiagen). Purified genomic DNA was re-suspended in TE buffer. DNA purity was tested by OD 260/280 ratios and quantified by UV spectrophotometry using a Nanodrop 2000 (Thermo Scientific, Wilmington, Del.). Genomic donor DNA for genotyping was obtained from Blood Center of Wisconsin which collects and stores DNA from all donors as part of the donor/recipient matching process.

Total Cf-DNA Analysis

Total cf-DNA content in each plasma sample was evaluated in triplicate by TaqMan quantitative real-time polymerase chain reaction (qRT-PCR) using an assay targeting RNaseP (Applied Biosystems, Foster City, Calif.). For each qRT-PCR reaction, one µl of cf-DNA extracted from plasma was used. A dilution series of a human genomic DNA samples originating from a TK6 cell-line (ATCC, Manassas, Va.) was used to create a standard curve for quantification. PCR analysis was carried out on an ABI7900 machine according to assay instructions from the company (Applied Biosystems). The amount of quantified cf-DNA level was converted to Genomic Equivalents (GE) by using a conversion factor of 6.6 pg of DNA per cell[21].

Percent Donor Specific Cf-DNA Analysis

The ratio of recipient to donor cf-DNA in plasma was quantified using the Digital ANalysis of Selected Regions (DANSR™) assay as previously described[18, 22]. The quantification was carried out by laboratory personnel blinded to clinical data at Ariosa Diagnostics (San Jose, Calif.). The DANSR approach enables simultaneous quantification of hundreds of genomic loci by cf-DNA dependent catenation of two locus-specific oligonucleotides via an intervening 'bridge' oligo to form a PCR template. For each sample 192 genomic loci on chromosomes 1-12 were targeted. Catenated PCR products were quantified on an Illumina HiSeq 2000™ instrument (Illumina, San Diego, Calif.). Genotyping of donor and recipient genomic DNA was carried out by the same assay. For this purpose genomic DNA was sheared to 300 bp by sonication (Covaris, Woburn, Mass.) prior to shipping. Final fragment size was verified on a Bioanalyzer (Agilent Technologies, Santa Clara, Calif.).

Sequencing Data Analysis

Calculation of percent DS cf-DNA in each plasma sample based on targeted NGS was done as outlined in the Supplemental Method. In brief, donor and recipient genotypes were designated and loci were deemed informative when recipient genotypes were homozygous and donor genotypes were either heterozygous or homozygous for the other allele. Subsequently the minor allele frequency (MAF) for informative loci was modeled as a binomial distribution and the percent DS cf-DNA was defined as the peak from this modeling[22, 23]. For samples containing pre and post biopsy data, the MAF was calculated solely with genotypes from recipient plasma and the donor genotypes for probe loci were inferred by the method of Expectation Maximization, an iterative process routinely used for latent variable imputation[24].

Data analysis QC for each sample was performed by plotting the negative log likelihood value of the data given the binomial model (LogLike) against the estimated MAF read error. If the fit was inadequate the sample was excluded (criteria in Supplemental Method). In addition, if the number of low read probes for any sample analysis exceeded 75 (out of the 192), the analysis was not included. Finally, if the sample starting material was <15 ng Tcf-DNA, a second extraction was performed. For all samples run in duplicate the results from the run with the highest DNA input was used for further analysis in the study.

Supplemental Method

Calculations of Percent Donor Specific Cell Free DNA

Genotypes were determined for 192 loci from DNA samples extracted from recipient and donor WBCs. Loci (markers) were deemed "informative" for calculating DS cf-DNA frequencies when recipient genotypes were homozygous and donor genotypes were either heterozygous or homozygous for the other allele. Loci with total read counts below the 5th percentile of their respective sequencing runs were excluded. To calculate the percent DS cf-DNA present in plasma samples the minor allele's frequency (MAF) was calculated for each locus by dividing the read counts for the minor allele (B) with the read count for the major allele (A) using the following formulas: $MAF=B_{hom}/(A_{hom}+B_{hom})$ and $MAF=B_{het}\times2/(A_{hom}+B_{het}\times2)$. The calculated minor allele frequencies were then modeled as a binomial distribution (Chu T, Bunce K, Hogge W A, Peters D G. A novel approach toward the challenge of accurately quantifying fetal DNA in maternal plasma. Prenat Diagn. 2010; 30:1226-1229; Sparks A B, Wang E T, Struble C A, Barrett W, Stokowski R, McBride C, Zahn J, Lee K, Shen N, Doshi J, Sun M, Garrison J, Sandler J, Hollemon D, Pattee P, Tomita-Mitchell A, Mitchell M, Stuelpnagel J, Song K, Oliphant A. Selective analysis of cell-free DNA in maternal blood for evaluation of fetal trisomy. Prenat Diagn. 2012: 1-7).

Figure 20:
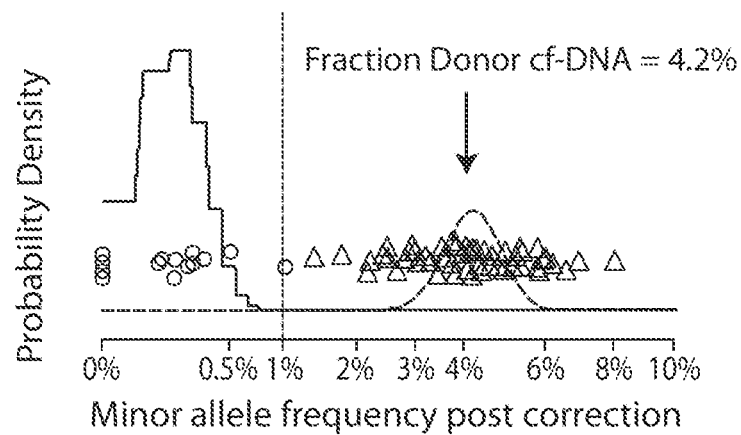
FIG. 20 provides an example of a distribution of minor allele frequencies from informative loci: Each triangle in the plot represents the minor allele frequency (MAF) at one loci and the circles represents the background noise measured in loci were recipient and donor are homozygous for the same allele. The background errors are subtracted from informative loci at the sequencing read level prior to determination of percent. The probability that a loci contains a certain MAF is calculated from the distribution of all informative loci and plotted on the y-axis as the probability density for probes to contain x % of the minor allele. The peak probability indicated by arrow is used as the percent MAF corresponding to the percent donor specific cell free DNA in the sample.
Figure 21:
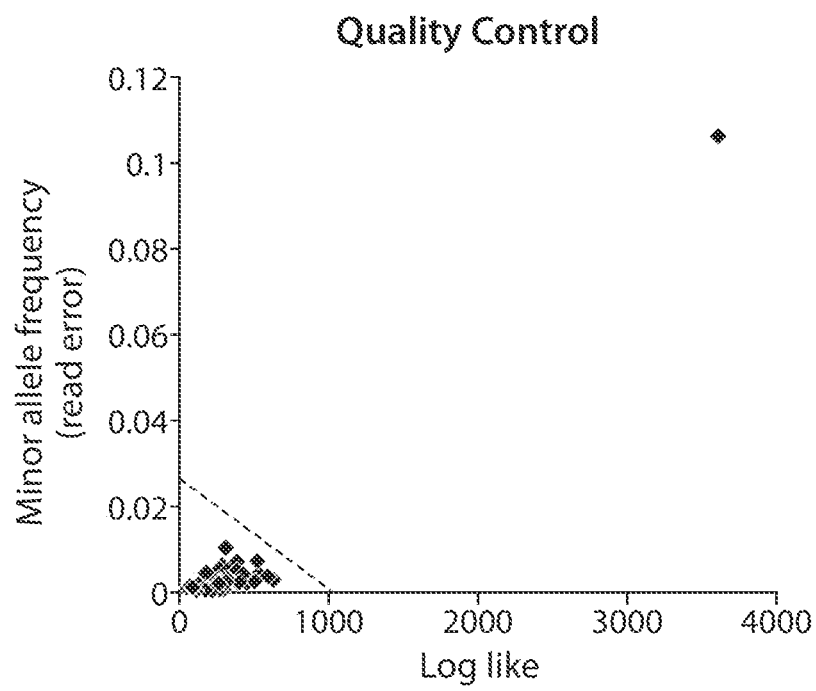
FIG. 21 shows the minor allele frequency from loci where recipient and donor are homozygous for the same allele plotted on the y-axis against the log likelihood (Log like) for goodness of fit as computed by software. Samples to the left of the dashed line all passed quality control (QC). Data are from 87 individual sample where genotyping was based on both donor and recipient genomic DNA. Excluded are Pre and Post Biopsy samples (12 samples). Only 1 sample was excluded due to clearly excessive rate of error reads and poor data fit as defined by the computed Log like value.

The percent DS cf-DNA in the plasma was defined as the peak of the distribution (FIG. 20). The maximum likelihood estimator (MLE) and standard error (SE) of the binomial frequency parameter were computed with the software R package stats4 (www.r-project.org/). Prior to calculating the MAF, an estimated read error was subtracted from the data. Error rates were calculated for each sample by identifying marker loci where donor and recipient were homozygous for the same allele and should not have had any minor allele read counts. MAF error was calculated by $MAF_{error}=B_{hom,\ error}/(A_{hom}+B_{hom,\ error})$. The read error was then modeled by the same maximum likelihood method described above such that the error was defined as the peak of the binomial distribution. The percent erroneous reads were subtracted at each loci equally from A and B read counts so that expected minor allele count error is zero. Some samples containing pre and post biopsy data the MAF was calculated solely with plasma. Similarly the maximum likelihood estimation of minor allele frequencies were computed using R package stats 4, but the donor genotypes for probe loci are inferred by the method of Expectation Maximization, an iterative process routinely used for latent variable imputation (Dempster A P, Laird N M, Rubin D B. Maximum likelihood from incomplete data via the em algorithm. Journal of the Royal Statistical Society. Series B (Methodological). 1977; 39:1-38).

Quality Control of Sequencing Data

Figure 22:
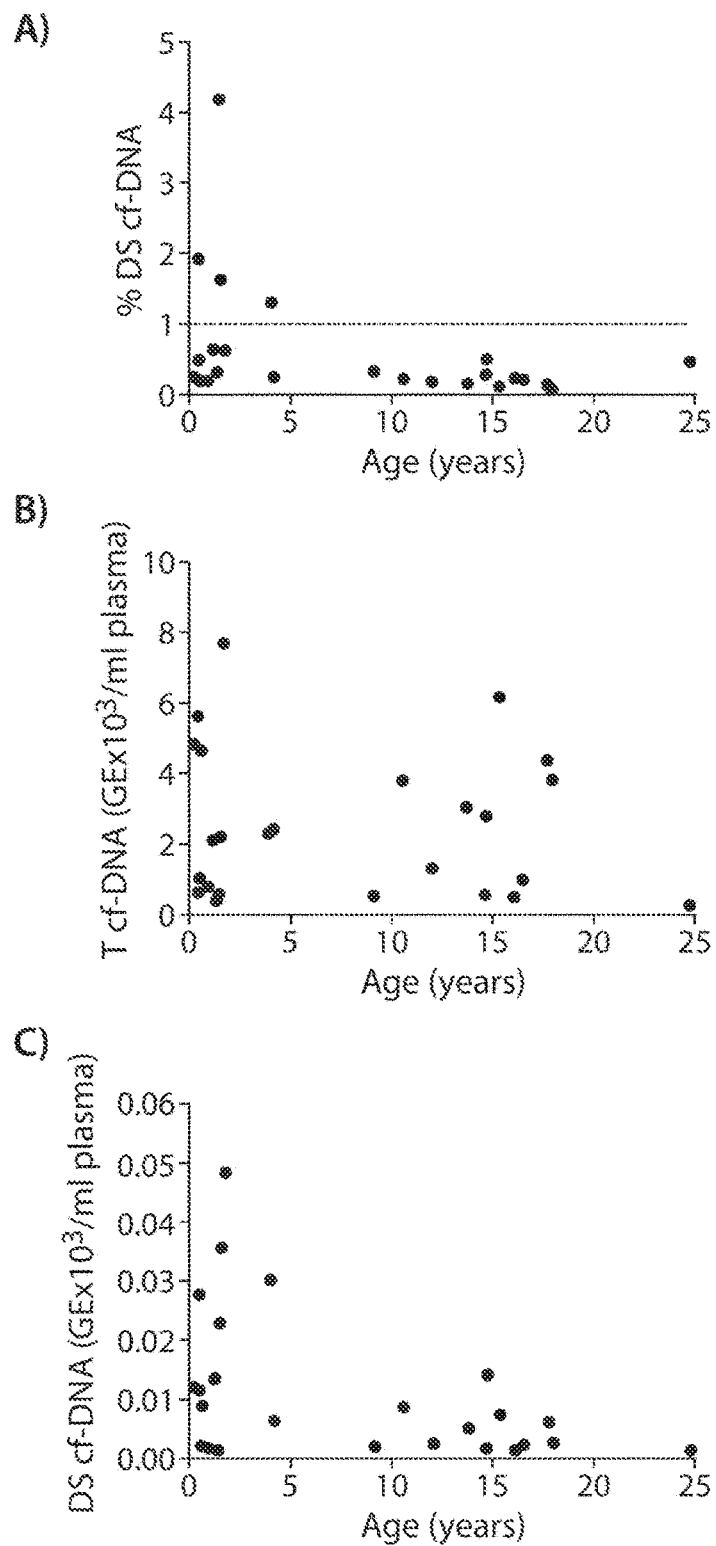
FIG. 22 shows results from data that included 25 first encounter samples collected during surveillance biopsy where there were no clinical concerns for rejection. Panel A) depicts percent DS cf-DNA, panel B) Tcf-DNA and panel C) depicts DS cf-DNA. Cell free DNA levels are plotted against the age of the patient at sample draw.

An automated process to calculate the fraction of DS cf-DNA and perform quality control (QC) analysis was run for each sample. QC factors include the number of informative loci in each sample (not less than 75), the total number of reads in each sample (above the 5th percentile of the sequencing run), and the standard error of minor allele frequencies. Excessively erroneous read counts in isolated loci are also identified as outliers and excluded. In a final step read error is plotted against the binomial models' log likelihood (a measure of goodness of fit computed with R's dbinom) and samples showing a clear visual difference from the majority are excluded (FIG. 22). Only 1 sample was excluded due to clearly excessive rate of error reads and poor data fit when plotting data according to the binomial distribution.

Statistical Methods

Since cf-DNA data did not appear normally distributed, non-parametric tests, such as a Friedman analysis of variance were used. The median and range are used as summary statistics. Paired samples (i.e. different times post-surgery) were compared using a Wilcoxon rank sum test and unpaired samples such as the rejection group vs. the surveillance group were compared using a Mann-Whitney test. Categorical data was compared using a chi-squared or a Fisher exact test. Correlations were summarized with a Pearson correlation and linear regression was done using SPSS version 20. A P-value<0.05 was considered significant although no adjustment for multiple testing was done.

Results

Ninety eight samples from 38 patients passed inclusion/exclusion criteria and were used for subsequent analysis. Genotyping of each donor recipient pair resulted in 54-80 informative loci per sample. Sequencing plasma samples produced on average 141,802 (range 59,380-229,510) high quality reads per sample that were used to calculate the percent DS cf-DNA as previously reported and further outlined in Supplemental Methods and FIG. 20[22, 23]. Each plasma sample contained on average 0.23±0.17% (standard deviations) read errors that were extracted prior to calculating the percent DS cf-DNA.

Cell-Free DNA Levels Following Heart Transplant Surgery (Scenario 1)

Figure 5:
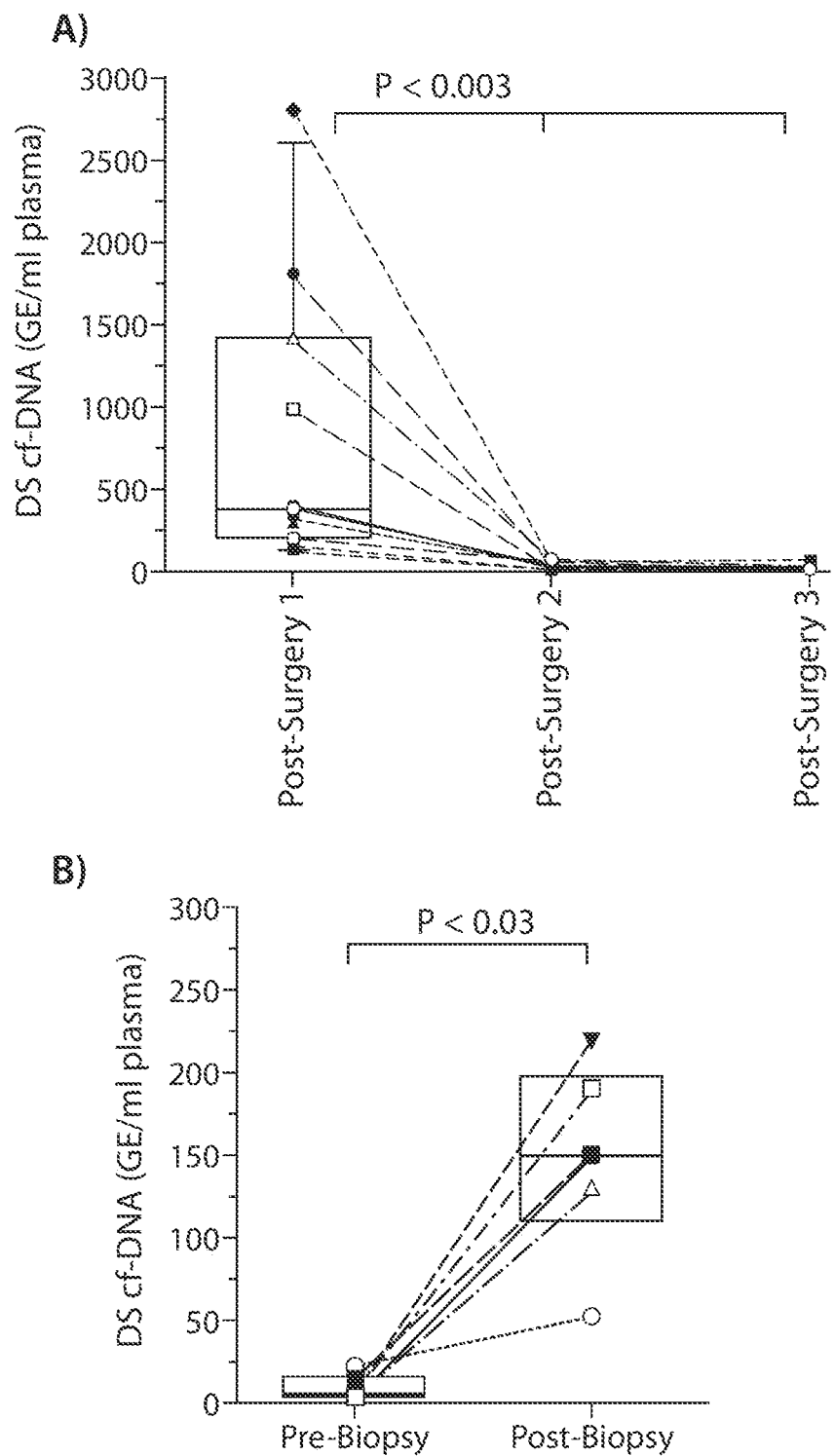
FIG. 5 shows two graphs showing DS cf-DNA post-surgery (panel A) and pre- and post-biopsy (panel B). Panel A) Levels of DS cf-DNA in plasma from pediatric heart transplant patients at three post-operative time points between days 1-10 (11 patients, 33 samples). Panel B) Levels of DS cf-DNA pre- and postendomyocardial biopsy (EMB) (6 patients, 12 samples) (post-biopsy, range 8-35 minutes). The sample indicated by the arrow had the shortest collection time (8 minutes) after biopsy. For both panels, statistical significance was calculated by the Wilcoxon rank sum test for paired data.
Figure 6:
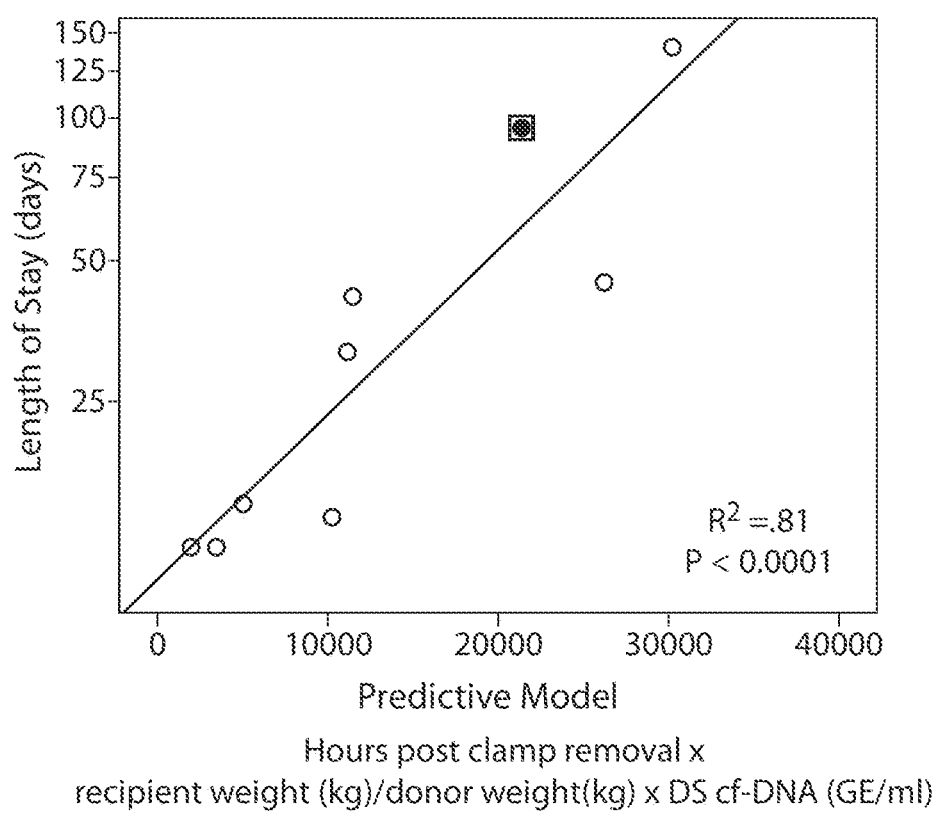
FIG. 6 is a graph of the length of stay Predictive Model (Formula 1). A significant correlation between length of hospitalization after transplantation surgery and a formula that includes three parameters was found to exist. These parameters include time since cross clamp removal, donor/recipient weight ratio, and the concentration of DS cf-DNA. The graph is plotted versus the log value of length of stay and each circle in the graph represents one patient. The circle with the square around it indicates the single patient who died prior to discharge.
Figure 7:
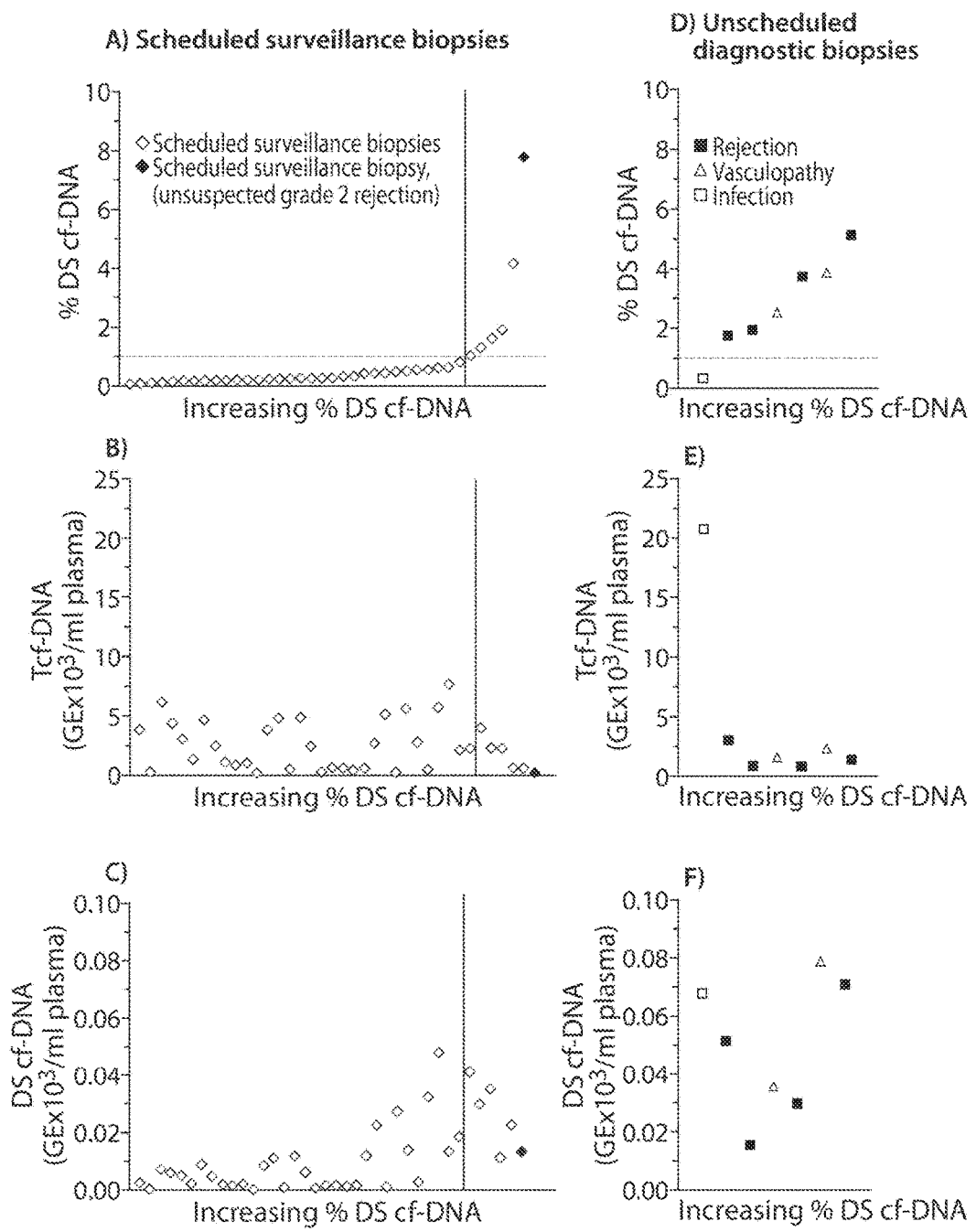
FIG. 7 is a series of graphs showing percent DS cf-DNA, total (T) cf-DNA, and DS cf-DNA in scheduled surveillance biopsies (panels A-C) and unscheduled diagnostic biopsies (panels D-F). Panels A & D) percent DS cf-DNA, panels B & E) T cf-DNA, and panels C & F) DS cf-DNA. Each data point represents a sample collected with the clinical data and biopsy findings indicated by the legend in panels A and D. Data in all six panels are sorted on the x-axis according to increasing percent DS cf-DNA so that T cf-DNA and DS cf-DNA from each sample align vertically. The dashed line in panels A and D highlights the 1% DS cf-DNA level, and the vertical solid lines in panels A-C orient the picture so all samples containing less than 1% DS cf-DNA are on the left-hand side and all samples greater than 1% are on the right.
Figure 8:
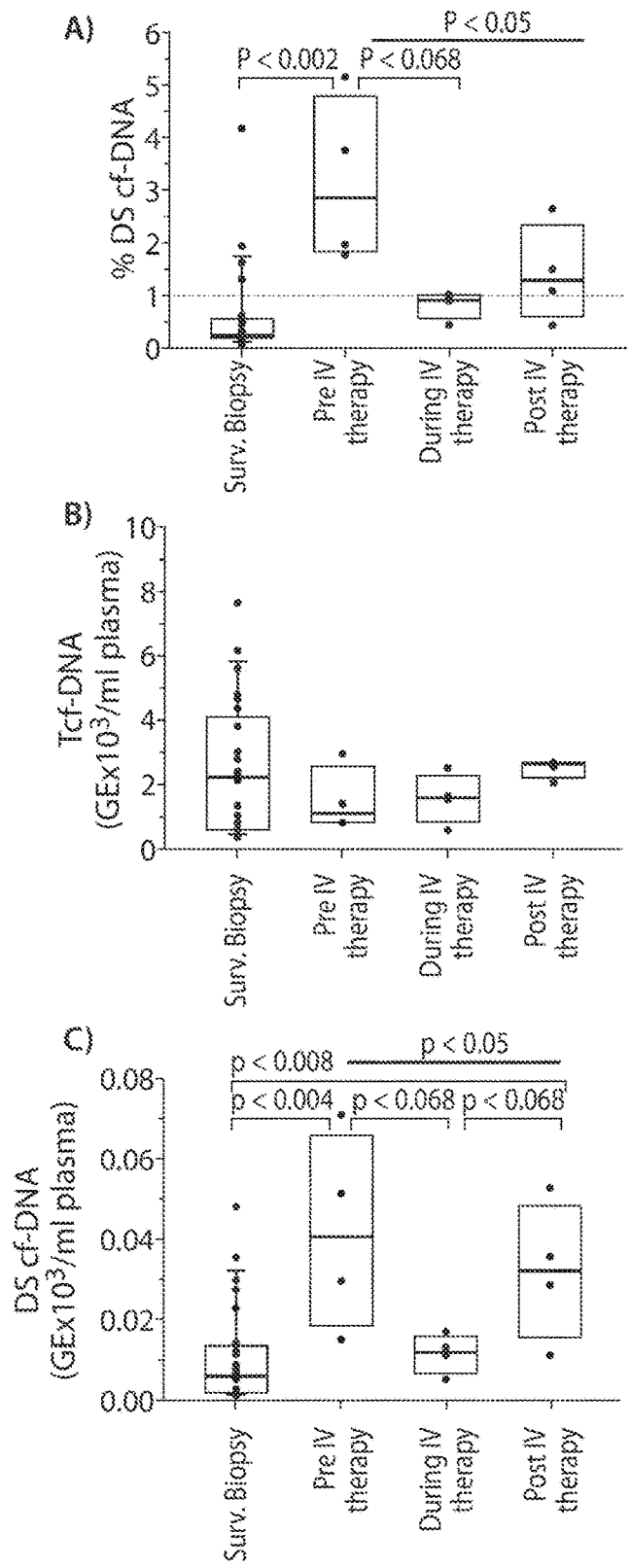
FIG. 8 is a series of graphs showing that percent DS cf-DNA level in plasma is an indicator of rejection. In each panel, surveillance biopsy results are compared with samples taken during biopsy proven rejection at three time-points; before, during and following intravenous (IV) immunosuppressive treatment. Panel A) percentage DS cf-DNA, panel B) T cf-DNA, and panel C) DS cf-DNA. Surveillance biopsy: 25 plasma samples from 25 patients taken at first study-enrolled surveillance EMB. Rejection samples: 12 samples from 4 patients with biopsy proven rejection, (pre IV therapy=3 to 44 hours prior to IV steroids), (post W therapy=43-98 hours after the last IV steroid dose). Patients found to have antibody-mediated rejection (AMR) not only received IV steroids but were also treated with Rituximab (375 mg/M2 weekly×4) and IV immunoglobulin. The single sample collected at the time of surveillance EMB (which had very high DS cf-DNA percent and was associated with a clinically unsuspected positive EMB for rejection) was excluded because it represented successful detection of subclinical rejection. The brackets with gray p-values indicate a significant difference between surveillance biopsy and rejection samples (pre IV therapy samples) as determined by the Mann-Whitney test for unpaired data. Statistical significance between pre, during, and post IV steroid therapy was calculated by Friedman's two way test of variance of ranks indicating that there is a significant difference between the three sample groups (p-value displayed on upper non-bracketed line). To identify differences between specific groups, the Wilcoxon rank sum test for paired data was used. The Wilcoxon test results are indicated by brackets with the lowest p-values displayed in black.

Thirty three samples were drawn at three time points after aortic clamp removal in each of 11 new heart transplant recipients (median age was 1 year, range 0-18 years): time point 1 (14-36 hours, day 1), time point 2 (84-126 hours, day 3-5), and time point 3 (160-206 hours, day 6-9). Increased levels of DS cf-DNA were observed in all samples at time point 1 (FIG. 5A). In each case these levels rapidly declined with subsequent samples showing a significant decrease between time points 1 and 2 (p<0.003) (FIG. 5A). The samples at time point 3 (day 6-9) were not different from baseline levels found in asymptomatic heart transplant recipients undergoing scheduled surveillance biopsy. A Predictive Model (Formula 1) was developed which factored hours from clamp removal, recipient and donor weight, and concentration of DS cf-DNA using the following equation: Predictive Model (Formula 1)=time post-clamp removal (hours)×(recipient weight (kg)/donor weight (kg))×DS cf-DNA (GE/ml). This model of transplant associated donor organ injury assumed a constant plasma clearance rate. Comparison of the predictive model calculation to the log of the length of hospital stay identified a significant correlation ($R^2$=0.81, P<0.0001, FIG. 6) consistent with donor organ injury. In addition, the single mortality in this group had an elevated value in the predictive model also consistent with significant donor organ injury (FIG. 6).

Cell-Free DNA Levels Immediately Pre and Post-Endomyocardial Biopsy (Scenario 2)

To further explore the hypothesis that this assay can measure DS cf-DNA as a direct result of myocardial cell damage a sub analysis which compared plasma samples collected pre- and post-scheduled surveillance EMB with a standard 1.5 mm bioptome was performed. Samples from six patients were collected in this manner. All post-biopsy samples contained dramatically higher DS cf-DNA (P<0.03, FIG. 5B) and percent DS cf-DNA than the corresponding pre-biopsy sample.

Cell-Free DNA Immediately Prior to Scheduled Surveillance Biopsy (Scenario 3)

Cell-free DNA levels in samples from 26 patients undergoing 38 surveillance biopsies were determined. The median age for the group was 4 years (0-25 years), and the median time since transplant was 0.3 years (0-6.5 years). Thirty two (84%) of the scheduled surveillance biopsy samples contained less than 1% DS cf-DNA. No patient with a DS cf-DNA fraction below 1% had pathological evidence of rejection as defined by ISHLT graded EMB. DS cf-DNA levels equaled or exceeded 1% in 6 samples (1.0% to 7.8%).

One surveillance biopsy returned positive for rejection (ISHLT grade 2R cellular) and this sample had the highest percentage DS cf-DNA (7.8%). The remaining five scheduled surveillance biopsy samples with DS cf-DNA percentages above 1% (range 1.0-4.2%) had negative biopsies (Specificity 86%).

Cell-Free DNA in Clinically Symptomatic Patients Prior to Unscheduled Diagnostic Biopsy (Scenario 4)

Seven samples were taken in six patients prior to unscheduled diagnostic EMB to rule out rejection as the cause of clinical symptoms). The median age was 18 years (14-25 years) and median time since transplant was 2 years (0-5 years). Six had DS cf-DNA levels greater than 1% (1.9-5.1%) and one sample had DS cf-DNA levels less than 1% (0.33%). Four of the six elevated levels were associated with biopsy confirmed acute rejection and the other two patients had significant coronary artery vasculopathy (CAV) on angiography (ISHLT, CAV 3 graded as previously defined[25]) (6/6, sensitivity 100%). The one symptomatic patient taken for diagnostic catheterization and biopsy with low percentage of DS cf-DNA had very high levels of Tcf-DNA as well as mildly elevated levels of DS cf-DNA. EMB was negative for rejection and coronary angiography was normal. The patient subsequently was diagnosed with sepsis which as indicated by cf-DNA levels implied a global infection rather than myocardial injury.

TABLE 4

Samples drawn due to clinical concern for rejection

| Diagnosed indication | % DS-cf-DNA | AMR† | ACR† | CAV | Months since transplant |
|---|---|---|---|---|---|
| Rejection | 1.9 | 1 | 3 | – | 22.6 |
| Rejection | 3.7 | 1* | 1* | – | 54.6 |
| Rejection | 5.1 | 0* | 2* | – | 51.6 |
| Rejection | 1.8 | 1 | 1 | – | 25.1 |
| Graft vasculopathy | 2.3 | NA | NA | + | 31 |
| Graft vasculopathy | 3.8 | 0 | 0 | + | 8.6 |
| Sepsis | 0.1 | 0 | 0 | – | 2.8 |

*EMB during rejection episode but not on day 1
†Rejection grade according to ISHLT 2005 revised standards
Antibody Mediated Rejection (AMR)
Acute Cellular Rejection (ACR)
Coronary Artery Vasculopathy (CAV)

Non-invasive laboratory and echocardiographic variables recorded at catheterization for the four patients with rejection were analyzed and compared with the 25 scheduled first encounter surveillance biopsies. Sensitivity and specificity for four non-invasive markers of rejection are compared in Table 5. Percent DS cf-DNA was the most sensitive marker (100%) with a specificity of 84% in this study. Left ventricular ejection fraction (LVEF) remained the most specific non-invasive marker (96%) but with a sensitivity of only 25%. Sensitivity and specificity calculations for the current study group were limited by fewer samples but were in the range of previous data.

TABLE 5

Sensitivity and Specificity for markers of rejection in this study

| | % DS-cf-DNA | | BNP | | Troponin | | LVEF | |
|---|---|---|---|---|---|---|---|---|
| | Rj 1 | SB | Rj 1 | SB | Rj 1 | SB | Rj 1 | SB |
| Total | 4 | 25 | 3 | 22 | 4 | 14 | 4 | 23 |
| Negative | 0 | 21 | 1 | 16 | 2 | 12 | 3 | 22 |

TABLE 5-continued

Sensitivity and Specificity for markers of rejection in this study

| | % DS-cf-DNA | | BNP | | Troponin | | LVEF | |
|---|---|---|---|---|---|---|---|---|
| | Rj 1 | SB | Rj 1 | SB | Rj 1 | SB | Rj 1 | SB |
| Positive* | 4 | 4 | 2 | 6 | 2 | 2 | 1 | 1 |
| | 100%[†] | 84%[‡] | 67%[†] | 72%[‡] | 80%[†] | 86%[‡] | 25%[†] | 96% [‡] |

*Levels used to indicate positive for rejection: % DS-cf-DNA >1% BNP >100 (pg/ml), Troponin >0.012 (ng/ml), LVEF <50 (%)
[†]Sensitivity,
[‡]Specificity
Rejection sample 1 (Rj 1),
Surveillance Biopsy (SB)

Cell Free DNA During Acute Rejection (Scenario 5)

Samples from four patients with rejection episodes were analyzed. Median age at the time of sample draw was 20 years (14-25 years) and the median time since transplant was 3 years (2-5 years). Time point 1 was upon diagnosis of rejection but prior to initiation of IV immunosuppressive therapy. Time point 2 was during the course of IV immunosuppressive therapy. Time point 3 was following the termination of IV immunosuppressive therapy. All pretreatment samples collected at the initial diagnosis had a percentage of DS cf-DNA>1% (4/4, sensitivity 100%) compared to patients with negative surveillance biopsy (21/25, specificity 84%) (P<0.002). Levels of DS cf-DNA in GE/ml plasma were also elevated (P<0.004) compared to the surveillance biopsy samples. Following initiation of IV immunosuppressive therapy all patients showed decreasing levels of DS cf-DNA (P<0.05). From time point 2 to time point 3, there appeared to be an increase in levels of both percent and the amount of DS cf-DNA, however the increase was not statistically significant possibly reflecting the small sample size. Levels of Tcf-DNA were similar in all three rejection time points and overlapped with levels drawn at surveillance biopsy.

Discussion

The work performed has furthered the understanding of cf-DNA dynamics in heart transplant patients in four important clinical settings; early post-transplant recovery, at the time of surveillance EMB, at diagnostic EMB, and during treatment for rejection. Fluctuations of DS cf-DNA are highly correlated with clinical status. Results herein demonstrate that levels of DS cf-DNA are elevated during rejection and cardiac allograft injury and decrease during recovery. Low levels of DS cf-DNA in recipient plasma (<1%) have a high predictive value; no sample obtained during a surveillance biopsy with <1% DS cf-DNA was associated with rejection by EMB. Taken together, these results show that monitoring cf-DNA from a simple blood draw in pediatric heart transplant patients could be safely utilized to guide the use of EMB in rejection surveillance.

The percent DS cf-DNA increases during rejection in cardiac transplant patients as detected by a whole genome sequencing (WGS) technique[13]. The WGS technique used to calculate percent DS cf-DNA used on average 13,000,000 Illumina sequencing reads per sample whereas in the targeted approach provided herein each sample was covered by approximately 100,000 reads from the same sequencing platform. In addition, as a result of targeting only selected and likely informative loci, a higher sequencing depth at each informative site per sequenced nucleotide is achieved when comparing DANSR to WGS. Higher sequencing depth enables a better accuracy in % DS cf-DNA measurements. This can be directly translated to lower assay cost for a targeted approach as performed in this study[18, 22].

Data generated by a series of samples collected following heart transplantation and during treatment for rejection yields clinically important information regarding organ recovery, expected length of stay and clinical improvement. The relatively short time it takes DS cf-DNA to reach its baseline levels following heart transplantation demonstrate rapid kinetics of clearance of cf-DNA. This is consistent with previously described fetal cf-DNA in maternal plasma that is cleared within hours of delivery, and with clearance of T cf-DNA hours post cessation of exercise[26, 27]. The data show that levels of DS cf-DNA fall to baseline (<1%) within three to five days following surgery suggesting that quantification of DS cf-DNA is a feasible strategy for detection of rejection in the high risk early post-transplant period, a period during which physicians monitor frequently for rejection with EMB. Although the hazard function for rejection peaked at one month post heart transplantation in a large cohort of adult cardiac transplant recipients, currently approved alternative gene expression assays are not approved for use during this early yet vulnerable period post cardiac transplantation[8]. In fact, during the first year following heart transplantation the recipient is usually subjected to approximately 6-9 biopsies and then at least yearly thereafter[28]. A sensitive non-invasive rejection monitoring method that can be applied as early as a week post-transplant could lessen the total number of biopsies needed over a lifespan considerably resulting in potential significant cost saving.

The current gold standard for the diagnosis of graft rejection in cardiac transplantation is EMB; however, controversy persists regarding grading and interpretation. There is variability in pathological interpretation of histologic grades, especially with severe cases of rejection due to the difficulty with estimating the amounts of nodular infiltrate present, so-called Quilty lesions[29]. Further, rejection can occur as a patchy or non-uniform process such that false negative biopsies, in which an unaffected area is sampled, has been described[30]. This is especially true at lower grades of rejection. DS cf-DNA has the ability to detect myocardial damage regardless of where it occurs. The current study shows that even a very small focal injury made by the bioptome results in a considerable increase in plasma DS cf-DNA. Taken together, these arguments support that cf-DNA has the potential to detect rejection earlier and in a more sensitive fashion than currently available methods summarized in Table 6.

TABLE 6

Summary of methods for monitoring rejection

| Test | Sensitivity/Specificity | Invasive | Test cost |
|---|---|---|---|
| Biopsy[37] | 90%/80% | Yes | $4,000 |
| Echocardiography[38] | 76%/88% | No | $500 |
| Troponin[6] | 80%/62% | No | $76 |
| BNP[5] | 90%/76% | No | $342 |
| CRP[5] | 64%/66% | No | $95 |
| Gene expression[8] | 75%/78% | No | $3,000 |
| Cell free DNA (WGS*)[15] | 83%/84% | No | ~$3,000 |
| Cell free DNA (TS[†])[‡] | 100%/84-86% | No | N/A |

*WGS (Whole Genome Sequencing)
[†]TS (Targeted Sequencing)
[‡]Data in this study DS cf-DNA can be a non-invasive, quantitative, extremely sensitive and specific biomarker. DNA is stable and collection tubes that preserve cell integrity under a variety of conditions including shipping prior to processing are available[20, 31]. Techniques specifically optimized for cf-DNA with respect to plasma processing, storage and DNA extraction have been established and are being used clinically at large scale to test for fetal trisomies[32-34]. With recent advances in sequencing techniques, NGS is the current method of choice for determining levels of fetal cf-DNA in maternal blood[22, 35, 36]. These techniques are directly applicable to detect cf-DNA from donor organs in the blood of the recipient[13]. This is a tremendous advantage for assay development where methods already have been optimized for clinical use. Because of the strength of the relationship between donor organ injury as measured by DS cf-DNA, a functional Predictive Model (Formula 1) was developed. It is anticipated that with a larger study the predictive value of early measures of DS cf-DNA will be further refined and validated.

Conclusions

A targeted NGS approach was employed to detect and quantify circulating levels of DS cf-DNA in pediatric heart transplant patients from ~1-3 ml of recipient plasma in the first 10 days following transplantation, at the time of routinely scheduled surveillance EMB, and during treatment of rejection. The percentage of DS cf-DNA was elevated in 100% of patients diagnosed with rejection. All patients with DS cf-DNA levels less than 1% were shown by biopsy and clinical parameters to be negative for rejection (negative predictive value was 100%). The percentage of DS cf-DNA in patients treated for rejection decreased to near baseline in all patients with anti-rejection therapy. Targeted NGS of circulating DS cf-DNA appears to be a sensitive cost-effective and safe tool for rejection surveillance, and it may offer an alternative to EMB.

References for Example 2

1. Hertz M I, Aurora P, Benden C, Christie J D, Dobbels F, Edwards L B, Kirk R, Kucheryavaya A Y, Rahmel A O, Rowe A W, Stehlik J. Scientific registry of the international society for heart and lung transplantation: Introduction to the 2011 annual reports. *J Heart Lung Transplant.* 2011; 30:1071-1077
2. Kaczmarek I, Deutsch M A, Sadoni S, Brenner P, Schmauss D, Daebritz S H, Weiss M, Meiser B M, Reichart B. Successful management of antibody-mediated cardiac allograft rejection with combined immunoadsorption and anti-cd20 monoclonal antibody treatment: Case report and literature review. *J Heart Lung Transplant.* 2007; 26:511-515
3. Daly K P, Marshall A C, Vincent J A, Zuckerman W A, Hoffman T M, Canter C E, Blume E D, Bergersen L. Endomyocardial biopsy and selective coronary angiography are low-risk procedures in pediatric heart transplant recipients: Results of a multicenter experience. *J Heart Lung Transplant.* 2012; 31:398-409
4. Pophal S G, Sigfusson G, Booth K L, Bacanu S A, Webber S A, Ettedgui J A, Neches W H, Park S C. Complications of endomyocardial biopsy in children. *J Am Coll Cardiol.* 1999; 34:2105-2110
5. Campbell D J, Woodward M, Chalmers J P, Colman S A, Jenkins A J, Kemp B E, Neal B C, Patel A, MacMahon S W. Prediction of heart failure by amino terminal-pro-b-type natriuretic peptide and c-reactive protein in subjects with cerebrovascular disease. *Hypertension.* 2005; 45:69-74
6. Dengler T J, Zimmermann R, Braun K, Muller-Bardorff M, Zehelein J, Sack F U, Schnabel P A, Kubler W, Katus H A. Elevated serum concentrations of cardiac troponin t in acute allograftrejection after human heart transplantation. *J Am Coll Cardiol.* 1998; 32:405-412
7. Moran A M, Lipshultz S E, Rifai N, O'Brien P, Mooney H, Perry S, Perez-Atayde A, Lipsitz S R, Colan S D. Non-invasive assessment of rejection in pediatric transplant patients: Serologic and echocardiographic prediction of biopsy-proven myocardial rejection. *J Heart Lung Transplant.* 2000; 19:756-764
8. Pham M X, Teuteberg J J, Kfoury A G, Starling R C, Deng M C, Cappola T P, Kao A, Anderson A S, Cotts W G, Ewald G A, Baran D A, Bogaev R C, Elashoff B, Baron H, Yee J, Valantine H A. Geneexpression profiling for rejection surveillance after cardiac transplantation. *The New England journal of medicine.* 2010; 362:1890-1900
9. Horwitz P A, Tsai E J, Putt M E, Gilmore J M, Lepore J J, Parmacek M S, Kao A C, Desai S S, Goldberg L R, Brozena S C, Jessup M L, Epstein J A, Cappola T P. Detection of cardiac allograft rejection and response to immunosuppressive therapy with peripheral blood gene expression. *Circulation.* 2004; 110:3815-3821
10. Deng M C, Eisen H J, Mehra M R, Billingham M, Marboe C C, Berry G, Kobashigawa J, Johnson F L, Starling R C, Murali S, Pauly D F, Baron H, Wohlgemuth J G, Woodward R N, Klingler T M, Walther D, Lal P G, Rosenberg S, Hunt S. Noninvasive discrimination of rejection in cardiac allograft recipients using gene expression profiling. *Am J Transplant.* 2006; 6:150-160
11. Stewart S, Winters G L, Fishbein M C, Tazelaar H D, Kobashigawa J, Abrams J, Andersen C B, Angelini A, Berry G J, Burke M M, Demetris A J, Hammond E, Itescu S, Marboe C C, McManus B, Reed E F, Reinsmoen N L, Rodriguez E R, Rose A G, Rose M, Suciu-Focia N, Zeevi A, Billingham M E. Revision of the 1990 working formulation for the standardization of nomenclature in the diagnosis of heart rejection. *J Heart Lung Transplant.* 2005; 24:1710-1720
12. Starling R C, Pham M, Valantine H, Miller L, Eisen H, Rodriguez E R, Taylor D O, Yamani M H, Kobashigawa J, McCurry K, Marboe C, Mehra M R, Zuckerman A, Deng M C. Molecular testing in the management of cardiac transplant recipients: Initial clinical experience. *J Heart Lung Transplant.* 2006; 25:1389-1395
13. Snyder T M, Khush K K, Valantine H A, Quake S R. Universal noninvasive detection of solid organ transplant rejection. *Proceedings of the National Academy of Sciences of the United States of America.* 2011; 108:6229-6234
14. Garcia Moreira V, Prieto Garcia B, Baltar Martin J M, Ortega Suarez F, Alvarez F V. Cell-free DNA as a non-invasive acute rejection marker in renal transplantation. *Clin Chem.* 2009; 55:1958-1966
15. Gadi V K, Nelson J L, Boespflug N D, Guthrie K A, Kuhr C S. Soluble donor DNA concentrations in recipient serum correlate with pancreas-kidney rejection. *Clin Chem.* 2006; 52:379-382
16. Lo Y M, Tein M S, Pang C C, Yeung C K, Tong K L, Hjelm N M. Presence of donor-specific DNA in plasma of kidney and liver-transplant recipients. *Lancet.* 1998; 351:1329-1330
17. Ghanta S, Mitchell M E, Ames M, Hidestrand M, Simpson P, Goetsch M, Thilly W G, Struble C A, Tomita-Mitchell A. Non-invasive prenatal detection of trisomy 21 using tandem single nucleotide polymorphisms. *PLoS One.* 2010; 5

18. Sparks A B, Wang E T, Struble C A, Barrett W, Stokowski R, McBride C, Zahn J, Lee K, Shen N, Doshi J, Sun M, Garrison J, Sandler J, Hollemon D, Pattee P, Tomita-Mitchell A, Mitchell M, Stuelpnagel J, Song K, Oliphant A. Selective analysis of cell-free DNA in maternal blood for evaluation of fetal trisomy. *Prenat Diagn.* 2012:1-7
19. Harris P A, Taylor R, Thielke R, Payne J, Gonzalez N, Conde J G. Research electronic data capture (redcap)—a metadata-driven methodology and workflow process for providing translational research informatics support. *Journal of biomedical informatics.* 2009; 42:377-381
20. Hidestrand M, Stokowski R, Song K, Oliphant A, Deavers J, Goetsch M, Simpson P, Kuhlman R, Ames M, Mitchell M, Tomita-Mitchell A. Influence of temperature during transportation on cellfree DNA analysis. *Fetal Diagn Ther.* 2012; 31:122-128
21. Lo Y M, Tein M S, Lau T K, Haines C I, Leung T N, Poon P M, Wainscoat J S, Johnson P J, Chang A M, Hjelm N M. Quantitative analysis of fetal DNA in maternal plasma and serum: Implications for noninvasive prenatal diagnosis. *American journal of human genetics.* 1998; 62:768-775
22. Sparks A B, Struble C A, Wang E T, Song K, Oliphant A. Noninvasive prenatal detection and selective analysis of cell-free DNA obtained from maternal blood: Evaluation for trisomy 21 and trisomy 18. *American journal of obstetrics and gynecology.* 2012; 206:319 e311-319
23. Chu T, Bunce K, Hogge W A, Peters D G. A novel approach toward the challenge of accurately quantifying fetal DNA in maternal plasma. *Prenat Diagn.* 2010; 30:1226-1229
24. Dempster A P, Laird N M, Rubin D B. Maximum likelihood from incomplete data via the em algorithm. *Journal of the Royal Statistical Society. Series B (Methodological).* 1977; 39:1-38
25. Mehra M R, Crespo-Leiro M G, Dipchand A, Ensminger S M, Hiemann N E, Kobashigawa J A, Madsen J, Parameshwar J, Starling R C, Uber P A. International society for heart and lung transplantation working formulation of a standardized nomenclature for cardiac allograft vasculopathy-2010. *J Heart Lung Transplant.* 2010; 29:717-727
26. Beiter T, Fragasso A, Hudemann J, Niess A M, Simon P. Short-term treadmill running as a model for studying cell-free DNA kinetics in vivo. *Clin Chem.* 2011; 57:633-636
27. Lo Y M, Zhang J, Leung T N, Lau T K, Chang A M, Hjelm N M. Rapid clearance of fetal DNA from maternal plasma. *American journal of human genetics.* 1999; 64:218-224
28. Kubo S H, Naftel D C, Mills R M, Jr., O'Donnell J, Rodeheffer R J, Cintron G B, Kenzora J L, Bourge R C, Kirklin J K. Risk factors for late recurrent rejection after heart transplantation: A multiinstitutional, multivariable analysis. Cardiac transplant research database group. *J Heart Lung Transplant.* 1995; 14:409-418
29. Marboe C C, Billingham M, Eisen H, Deng M C, Baron H, Mehra M, Hunt S, Wohlgemuth J, Mahmood I, Prentice J, Berry G. Nodular endocardial infiltrates (guilty lesions) cause significant variability in diagnosis of ishlt grade 2 and 3a rejection in cardiac allograft recipients. *J Heart Lung Transplant.* 2005; 24:S219-226
30. Pajaro O E, Jaroszewski D E, Scott R L, Kalya A V, Tazelaar H D, Arabia F A. Antibody-mediated rejection in heart transplantation: Case presentation with a review of current international guidelines. *Journal of transplantation.* 2011; 2011:351950
31. Fernando M R, Chen K, Norton S, Krzyzanowski G, Bourne D, Hunsley B, Ryan W L, Bassett C. A new methodology to preserve the original proportion and integrity of cell-free fetal DNA in maternal plasma during sample processing and storage. *Prenat Diagn.* 2010; 30:418-424
32. Ashoor G, Syngelaki A, Wagner M, Birdir C, Nicolaides K H. Chromosome-selective sequencing of maternal plasma cell-free DNA for first-trimester detection of trisomy 21 and trisomy 18. *American journal of obstetrics and gynecology.* 2012; 206:322 e321-325
33. Bianchi D W, Platt L D, Goldberg J D, Abuhamad A Z, Sehnert A J, Rava R P. Genome-wide fetal aneuploidy detection by maternal plasma DNA sequencing. *Obstetrics and gynecology.* 2012; 119:890-901
34. Chiu R W, Akolekar R, Zheng Y W, Leung T Y, Sun H, Chan K C, Lun F M, Go A T, Lau E T, To W W, Leung W C, Tang R Y, Au-Yeung S K, Lam H, Kung Y Y, Zhang X, van Vugt J M, Minekawa R, Tang M H, Wang J, Oudejans C B, Lau T K, Nicolaides K H, Lo Y M. Non-invasive prenatal assessment of trisomy 21 by multiplexed maternal plasma DNA sequencing: Large scale validity study. *BMJ.* 2011; 342:c7401
35. Chiu R W, Chan K C, Gao Y, Lau V Y, Zheng W, Leung T Y, Foo C H, Xie B, Tsui N B, Lun F M, Zee B C, Lau T K, Cantor C R, Lo Y M. Noninvasive prenatal diagnosis of fetal chromosomal aneuploidy by massively parallel genomic sequencing of DNA in maternal plasma. *Proceedings of the National Academy of Sciences of the United States of America.* 2008; 105:20458-20463
36. Fan H C, Blumenfeld Y J, Chitkara U, Hudgins L, Quake S R. Noninvasive diagnosis of fetal aneuploidy by shotgun sequencing DNA from maternal blood. *Proceedings of the National Academy of Sciences of the United States of America.* 2008; 105:16266-16271
37. Zerbe T R, Arena V. Diagnostic reliability of endomyocardial biopsy for assessment of cardiac allograft rejection. *Human pathology.* 1988; 19:1307-1314
38. Puleo J A, Aranda J M, Weston M W, Cintron G, French M, Clark L, Fontanet H L. Noninvasive detection of allograft rejection in heart transplant recipients by use of doppler tissue imaging. *J Heart Lung Transplant.* 1998; 17:176-184

The invention claimed is:
1. A method of treatment of a subject, wherein the subject is a recipient of a transplant, the method comprising:
  (a) determining an amount of cell-free DNA not native to the subject based on a method comprising:
    (i) analyzing nucleic acids from cell-free DNA extracted from a biological sample obtained from the subject to identify a plurality of loci, the nucleic acids comprising first nucleic acids of the subject and second nucleic acids not native to the subject;
    (ii) determining an allele of each of the plurality of loci;
    (iii) selecting at least one informative locus from the plurality of loci based on the determining of the allele; and
    (iv) calculating an estimated allele frequency of a first allele at the at least one informative locus using a statistical distribution; and
  (b) comparing the determined amount of the cell-free DNA not native to the subject to a threshold value of cell-free DNA; and

(c) administering an anti-rejection therapy or a therapeutic agent that treats a systemic disease to the subject when the determined amount of the cell-free DNA not native to the subject is greater than the threshold value of cell-free DNA.

2. The method of claim 1, wherein the at least one informative locus is selected by:
   detecting the first allele and a second allele at a locus; and
   determining that the first nucleic acids are homozygous for the second allele at the at least one informative locus and the second nucleic acids are heterozygous or homozygous for the first allele at the at least one informative locus.

3. The method of claim 1, wherein:
   the first allele comprises a minor allele; and
   the estimated allele frequency of the minor allele is calculated using a statistical distribution.

4. The method of claim 1, wherein:
   the first allele comprises a minor allele; and
   the estimated allele frequency of the minor allele is calculated using an expectation-maximization algorithm.

5. The method of claim 1, wherein the nucleic acids are analyzed using sequencing.

6. The method of claim 1, further comprising, based on the determined amount of the cell-free DNA not native to the subject, evaluating an effect of a therapy administered to the subject.

7. The method of claim 6, wherein the amount of the therapy administered to the subject is increased or decreased based on the evaluation.

8. The method of claim 6, wherein a different therapy is administered to the subject based on the evaluation.

9. The method of claim 1 wherein the subject is a recipient of a heart transplant.

10. The method of claim 9, wherein the subject is a pediatric patient.

11. The method of claim 1, wherein the biological sample comprises, blood, plasma, serum or urine.

12. The method of claim 1, wherein the threshold value of cell-free DNA is 1%.

* * * * *